United States Patent [19]
Guerry et al.

[11] Patent Number: 6,114,330
[45] Date of Patent: *Sep. 5, 2000

[54] SUBSTITUTED 2,4-DIAMINOPYRIMIDINES

[75] Inventors: Philippe Guerry, Binningen, Switzerland; Christian Hubschwerlen, Durmenach, France; Synèse Jolidon, Blauen, Switzerland; Jean-Luc Specklin, Kembs-Schaferhof, France; Pierre-Charles Wyss, Muttenz, Switzerland

[73] Assignee: Hoffmann-La Roche Inc., Nutley, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 09/028,980

[22] Filed: Feb. 25, 1998

[30] Foreign Application Priority Data

Mar. 3, 1997 [EP] European Pat. Off. ............... 97103436

[51] Int. Cl.[7] ...................... C07D 247/02; C07D 405/14; A61P 31/04; A61K 31/506

[52] U.S. Cl. ...................... 514/248; 514/234.5; 544/119; 544/237

[58] Field of Search ................................. 514/234.5, 248; 544/119, 237

[56] References Cited

U.S. PATENT DOCUMENTS 5,866,583  2/1999  Guerry .................................... 514/275

FOREIGN PATENT DOCUMENTS

96/16046  5/1996  European Pat. Off. .
97/43277  11/1997  European Pat. Off. .

OTHER PUBLICATIONS

Roth, et al.; *2,4–Diamino–5–benzylpyrimidines as Antibacterial Agents; J. Med. Chem.*; 32; (8), 1949 (1989).
Baccanari, D.P. and S.S. Joyner, *Biochemistry*, 20:1710–1716 (1981).
Hartman, P.G., et al., *FEBS Letters*, 242:175–160 (1988).
"Academic Press Dictionary of Science and Technology" p. 93, 1992.

*Primary Examiner*—Mark L. Berch
*Attorney, Agent, or Firm*—George W. Johnston; Patricia S. Rocha-Tramaloni; Eileen M. Ebel

[57] ABSTRACT

The invention is concerned with compounds of formula

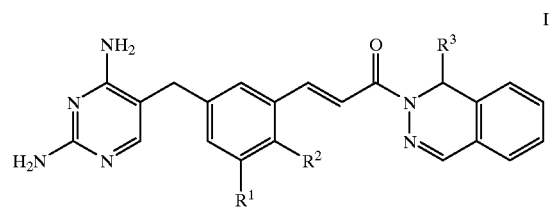

wherein $R^1$ is lower-alkoxy, $R^2$ is hydroxy or lower-alkoxy, $R^3$ is hydrogen, cyano, alkyl, alkenyl, cycloalkyl, aryl, heterocycyl, aryl-Q-alkyl, or a group of the formula $-CR^4R^{4'}COR^5-$, Q is $-SO-$ or $-SO_2-$; $R^4$, $R^{4'}$ are each independently hydrogen, alkyl, aryl or heterocyclyl, $R^5$ is hydrogen, alkyl, alkoxy, hydroxy, aryl or heterocycyl, or $R^4$ and $R^5$ together form $-(CH_2)_n-$, and n is a whole number between 2 to 5 inclusive and the enantiomers, epimers, and diastereomers thereof, as well as pharmaceutically acceptable salts thereof. These compounds have valuable antibacterial activity.

210 Claims, No Drawings

SUBSTITUTED 2,4-DIAMINOPYRIMIDINES

The present invention is concerned with compounds of the formula

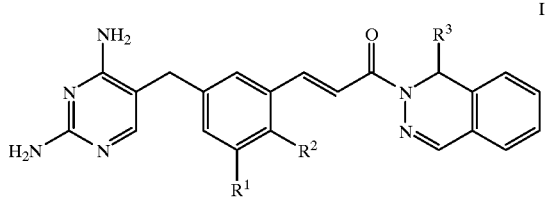

wherein
$R^1$ is lower alkoxy;
$R^2$ is hydroxy or lower alkoxy;
$R^3$ is hydrogen, cyano, lower alkyl, alkenyl, cycloalkyl, bicyclyl, aryl, heterocyclyl, heteroaryl, aryl-Q-alkyl, or a group of the formula —$CR^4R^{4"}COR^5$;
Q is —SO— or $SO_2$;
$R^4$, $R^{4"}$ are each independently hydrogen, alkyl, aryl or heterocyclyl;
$R^5$ is hydrogen, alkyl, alkoxy, aryl or heterocyclyl or hydroxy, or
$R^4$ and $R^5$ together form —$(CH_2)_n$—, and
n is a whole number between 2 to 5 inclusive,
wherein
lower alkoxy, lower alkyl, alkyl, and cycloalkyl are unsubstituted or substituted by one or more groups selected from amino, dialkylamino, morpholino, piperidino, piperazino, hydroxy which is optionally esterified by an amino acid or sulfuric acid, halide, nitrile, thiocyanato, sulfato, lower-alkylsulphanoyl, oxo, carboxy, carbamino, carbalkoxy, carbamoyloxy, alkoxy, morpholinoalkoxy, piperidinoalkoxy, and cycloalkyl which is unsubstituted or substituted by one or more groups as defined above;
aryl, heterocyclyl and heteroaryl are unsubstituted or substituted by one or more groups selected from phenyl, lower alkyl which is unsubstituted or substituted by one or more groups as defined above, cycloalkyl which is unsubstituted or substituted by one or more groups as defined above, hydroxy, cyano, thiocyanato, amino, halide, oxo, lower alkoxy which is unsubstituted or substituted by one or more groups as defined above, lower alkoxycarbonyl, di(lower alkyl) amino, carbamoyl, mono- or di-lower alkylcarbamoyl, lower alkylsulfanoyl, lower alkylsulfonyl, sulfamoyl, N-mono- or di-lower alkylsulfamoyl, heterocyclyl which is unsubstituted or substituted by one or more groups as defined above, or heterocyclyl-lower alkyl, the heterocyclyl and lower alkyl each of which is unsubstituted or substituted by one or more groups as defined above;
alkenyl is unsubstituted or substituted by one or more substituents selected from the group cyano, acryloyl, and heteroaryl which is unsubstituted or substituted by one or more groups as defined above;
and the epimers, enantiomers and diastereomers thereof as well as the pharmaceutically acceptable salts thereof.

The compounds of formula I are novel and possess valuable antibiotic properties. They can be used for the control or prevention of infectious diseases. In particular, they exhibit a pronounced antibacterial activity even against multiresistant, gram-positive strains and against resistant pneumococci and opportunistic pathogens such e.g. *Pneumocystis carinii*. The compounds of formula I can also be administered in combination with known antibacterially-active substances and then exhibit synergistic effects. Typical combination partners are e.g. sulfonamides, with which the compounds of formula I or their salts can be admixed in various ratios.

Examples of sulfonamides which can be combined with the compounds of the present invention can be selected from the group sulfadiazine, sulfamethoxazole, sulfatroxazole, sulfamerazine, sulfadoxine, sulfadimethoxine, sulfamethazine, sulfapyrazole, sulfaquinoxaline, sulfachloropyridazine, sulfaguanidine, sulfalene, sulfametin, sulfamethoxine, sulfamethoxy-pyridazine, sulfamethylphenazole, sulfaphenazole, sulfamoxole, sulfapyrazine, sulfapyridazine, sulfapyridine, sulfasymazine, sulfathiozole, sulfametrole, and sulfamethizole.

Objects of the present invention are compounds of formula I and their pharmaceutically acceptable salts per se and for use as therapeutically active substances, medicaments based on these substances, optionally in combination with sulphonamides, and their production; the use of these substances as medicaments and for the production of antibacterially-active medicaments; as well as making the compounds of formula I and their pharmaceutically acceptable salts and intermediates for their making the compounds.

The terms "lower alkyl" and "lower alkoxy" embrace-chain or branched alkyl and, respectively, alkoxy groups which have from 1 to 8 and preferably 1–4 carbon atoms and which are optionally substituted by one or more substituents, such as, for example, methyl, ethyl, n-propyl, isopropyl, n-butyl, isobutyl, tert.butyl, n-pentyl and n-hexyl; and, respectively, methoxy, ethoxy, n-propoxy, isopropoxy, n-butyloxy, isobutyloxy, and tert.butoxy. Suitable substituents for these alkyl and alkoxy groups are functional groups such as, for example, amino, dialkylamino, morpholino, piperidino, piperazino, hydroxy, halide, nitrile, thiocyanato, sulfato, lower alkyl sulphanoyl (e.g., methylsulfanyl), oxo, carbamoyloxy, carboxy, carbamino or carbalkoxy groups or substituents such as alkoxy, morpholinoalkoxy, piperidinoalkoxy and cycloalkyl. Methoxymethyl, hydroxymethyl, hydroxybutyl, dihydroxybutyl, 2-oxo-propyl, 3-propionaldehyde, perfluorohexyl and the like are examples of such substituted alkyl and alkoxy groups.

The term "alkenyl" embraces unsaturated hydrocarbon residues from 2 to 6 carbon atoms inclusive containing a double bond such as vinyl, allyl, butenyl and the like. The alkenyl chain is optionally substituted by one or more substituents, such as, for example, cyano acryloyl, and heterocyclyl, as defined below.

The term "cycloalkyl" embraces cyclic alkyl groups with preferably 3–6 carbon atoms, which can be substituted with functional groups and substituents as mentioned under alkyl and alkoxy.

Examples for bicyclyl groups are adamantyl or bicyclo [2.2.1]hept-2endo- and/or 2exo-yl.

The term "aryl" denotes 6-membered mono- or poly-nuclear aromatic groups with preferably 6–14 carbon atoms. Examples of such groups are phenyl, naphthyl, anthryl and phenanthryl, which can be substituted by one or more substituents. Suitable substituents for ether mentioned aryl groups are e.g. phenyl; lower alkyl (e.g. methyl); substituted lower alkyl as provided for above (e.g. trifluoromethyl, pentafluoro ethyl); $C_{3-6}$ cycloalkyl (e.g. cyclopropyl); hydroxy; cyano; thiocyanato; amino; hydroxyalkyl, optionally esterified with amino acids or sulphuric acid (such as, for example, 2-amino-propionic acid ester or 2-amino-5-guanidino-pentanoic acid ester); halogen (e.g. chlorine); lower alkoxy (e.g. methoxy, n-butoxy); substituted lower alkoxy as described above; lower alkoxycarbonyl (e.g. methoxycarbonyl); di(lower alkyl)amino (e.g. dimethylamino, diethylamino); carbamoyl, mono- or di-lower-alkylcarbamoyl; lower-alkylsulphanoyl, (e.g. methylsulphanyl); lower-alkylsulphonyl, (e.g. methanesulphonyl); sulphamoyl, N-mono- or di-lower alkylsulphamoyl; heterocyclyl, or with heterocyclyl-lower-alkyl. Additionally, aryl can be substituted by two vicinal alkoxy groups which form a fused ring, such as, for example, 2,3-dihydro-benzo[1,4]dioxin-6-yl and benzo[1,3]dioxin-5-yl.

The term "heterocyclyl" embraces in the scope of the present invention 4 to 6 membered rings with 1 to 3 N, O and/or S atoms such as, for example, cyclic lactones, cyclic lactames, ketals (such as, for example, 2-dimethyl-1,3-dioxolan-yl), acetals (e.g. 1,3, dioxolan-2-yl or 1,3,-dioxan-2-yl); examples of such rings are morpholin-4-yl, 4-methyl-piperazin-1-yl, imidazol-1-yl, thiazolyl and [1,2,4] triazol-1-yl, dithianyl, tetrahydropyranyl; the heterocyclic rings can be substituted with substituents described above for the aryl and lower alkyl groups. Such substituents are especially lower alkyl, lower alkoxy, hydroxy, amino, hydroxyalkyl, aminoalkyl or oxo. Pyrrolidinone, methylpyrrolidinone and the like are examples of preferred substituted heterocyclic rings.

The term "heterocyclyl-lower alkyl" embraces in the scope of the present invention heterocyclic rings which are linked via an alkyl residue. Preferred heterocyclyl-lower-alkyl units are e.g morpholin-4-ylmethyl, 4-methyl-piperazin-1-ylmethyl, imidazol-1-ylmethyl and [1,2,4] triazol-1-ylmethyl, dioxolan-4yl-ethyl, prrolidinylamethyl, pyperidinylmethyl and the like. The heterocyclyl and lower alkyl groups can each be unsubstituted or substituted as provided for above.

The term "heteroaryl" denotes in the scope of the present invention 5- or 6-membered, mono- or poly-nuclear heteroaromatic groups with preferably 5–13 carbon atoms and 1–4 hetero atoms, preferably nitrogen, oxygen and/or sulphur atoms. Furyl, pyranyl, thienyl, pyrrolyl, pyrazolyl, imidazolyl, triazolyl, tetrazolyl, oxazolyl, oxadiazolyl, isoxazolyl, thiazolyl, isothiazolyl, pyridyl, pyridazinyl, pyrimidinyl, pyrazinyl, triazinyl are examples. These groups can also be linked with a fused ring, preferably a phenyl ring. Examples of such linked rings are, for example, benzopyranyl, benzofuranyl, indolyl and quinolinyl. The heteroaryl groups can be substituted, for example with substituents as described above for the aryl and lower alkyl groups. Additionally, heteroaryl can be substituted by two vicinal alkoxy groups which form a fused ring, such as, for example, [1,3]dioxolo[4,5-b]pyridin-6-yl.

As used herein, halide or halogen refer to chloride or chlorine, fluoride or fluorine, bromide or bromine, and iodide or iodine.

In formula I the group $R^1$ is preferably methoxy; $R^2$ is preferably hydroxy, lower alkoxy such as e.g. methoxy or ethoxy; or lower alkoxy substituted by lower alkoxy such as e.g. methoxymethoxy, lower alkoxy substituted by heterocyclyl such as e.g. morpholin-4-yl-ethoxy or lower alkoxy substituted by lower alkoxycarbonyl-lower alkyl, preferably methoxycarbonylmethyl.

Preferred lower alkyl groups $R^3$ include the following groups: methyl (Ex. 1.32, 1.33, 2.11); ethyl (Ex. 2.13); propyl (Ex. 1.30, 1.31, 2.15, 2.16); 3-methyl-butyl (Ex. 2.17); tert.butyl (Ex. 1.23).

Preferred substituents for the lower alkyl residue $R^3$ include the following substituents:
hydroxy such as e.g. hydroxypropyl (Ex. 2.18), hydroxybutyl (Ex. 2.20), 3,4-dihydroxybutyl (Ex. 16);
methylsulfanyl such as e.g. methylsulfanylmethyl (Ex. 1.17); fluoro such as e.g. tridecafluorhexyl (Ex. 2.3);
carbamoyloxy such as e.g. carbamoyloxy-butyl (Ex. 2.21), carbamoyloxy-propyl (Ex. 2.22);
thiocyanato such as e.g. thiocyanatobutyl (Ex. 11);
—$SO_4H$ such as e.g. sulfatobutyl (Ex. 10.2) or
heterocyclyl such as e.g. [1.3]dioxolan-2-yl-ethyl (Ex. 2.23), [1.3]dioxolan-4yl-ethyl (Ex. 4).
heterocyclylcarboyloxy such as e.g. morpholinylcarbonyloxybutyl (Ex. 2.19).

Preferred substituents for the alkenyl-residue $R^3$ include the following substituents:
cyano such as e.g. cyanobutenyl (Ex. 13.1);
acryloyl such as e.g. acryloylbutenyl (Ex. 13.2).

Preferred lower cycloalkyl groups $R^3$ include the following groups: cyclopropyl (Ex 1.46 1.52, 1.53), cyclobutyl (Ex. 1.56), cyclopentyl (Ex. 1.57), cyclohexyl (Ex. 1.60).

A preferred substituent for the cycloalkyl residue $R^3$ is the oxo-group such as e.g. cyclopentanone (Ex. 1.9), cyclohexanone (Ex. 1.10).

Preferred heterocyclyl- or substituted heterocyclyl-residues $R^3$ include: dithian-2-yl (Ex. 1.49) or tetrahydropyran-2-on 1 (Ex. 1.14).

Examples for the group "aryl-Q-alkyl" include: phenylsulfonylmethyl (Ex. 1.69) or Phenylsulfinylmethyl (Ex. 2.5).

Examples for the group "$CR^4R^{4'}COR^5$" include:
methylcarbonylmethyl (Ex. 1.11), methoxycarbonyl (dimethyl)methano $CH_3$—CO—$C(CH_3)_2$— (Ex. 1.12), hydroxycarbonyldimethylmethano (—$C(CH_3)_2$—CO—OH (Ex. 7),
phenylcarbonyl-methyl (Ex. 1.13), phenylcarbonyl(methyl) methyl (Ex. 1.15) or
furanylcarbonyl-methyl (Ex. 1.16).

Preferred aryl groups $R^3$ include phenyl or biphenyl, most preferred phenyl.

The phenyl residue can be mono, di-or tri substituted by the following groups:
lower alkyl such as e.g. methyl (Ex. 1.19, 1.22, 1.25, 1.40, 1.41), ethyl (Ex. 1.20), butyl (Ex. 1.3), tert.butyl (Ex. 1.18);
substituted lower alkyl such as e.g. hydroxymethyl (Ex. 2.6, 2.8, 2.9, 3.3, 8.3), hydroxy-ethyl (Ex. 1.68, 2.12), methoxymethyl (Ex. 1.71), trifluormethyl (Ex. 1.58), dimethylaminomethyl (Ex. 1.7), diisopropylamino-methyl (Ex. 1.72), 2-aminopropionylmethyl (Ex. 9.1), carbamoyloxymethyl (Ex. 2.14);
lower alkoxy, preferably methoxy (Ex. 1.62, 32.6);
halogen, preferably fluoro (Ex. 2.1, 2.2), chloro (Ex. 1.73);
methylsulfanyl (Ex. 1.47, 1.54, 1.55);
dimethylamino (Ex. 1.38);
dimethylamino sulfonyl (Ex. 1.6, 1.70) cyano (Ex. 1.64);
hydroxy (Ex. 2.7, 2.10);
lower alkoxy such as e.g. methoxy (Ex. 1.61, 32.3);
substituted lower alkoxy such as e.g. hydroxyethoxy (Ex. 32.11), trifluormethoxy (Ex. 1.21), 1-ethoxy-ethoxy (Ex. 1.35), 2-ethoxy-ethoxy (Ex. 1.39);
lower alkoxy-carbonyl such as e.g. tert.butoxy carbonyl (Ex. 1.65); heteroaryl such as e.g. prrrol-1-yl (Ex. 1.42);
heterocyclyl-lower alkyl such as e.g. 4-methyl-piperazin-1-ylmethyl (Ex. 1.75), 4-morpholin-4-yl-methyl (Ex. 1.76).

Preferred heteroaryl groups $R^3$ include pyridyl (Ex. 1.51, 1.2, 32.8) pyrimidinyl, thiophen-2-yl (Ex. 1.66), 5,6-dihydro-4H-pyran-2-yl (Ex. 1.24), furan-2-yl (Ex. 1.28, 1.29, 1.4, 3.2, 8.2), thiazol-2-yl (ex. 1.5), [1,3]dioxolo[4,5-b]pyridin-6-yl (Ex. 32.13).

The heteroaryl groups $R^3$ can be mono, di-or tri substituted by the following groups:

lower alkyl such as e.g. methyl (Ex. 1.37, 1.43, 1.44, 1.48, 1.67, 1.8, 32.1, 32.2, 32.4, 32.5), ethyl (Ex. 34.1);

substituted lower alkyl such as e.g. hydroxymethyl (Ex. 32.7), hydroxy-1-methyl-ethyl (Ex. 1.78);

halogen, preferably chloro (Ex. 1.59), bromo (Ex. 32.9);

lower alkoxy such as e.g. methoxy (Ex. 1.74, 32.10, 32.12);

substituted lower alkoxy such as e.g. methoxy-ethoxy (Ex. 32.15), methoxy-ethoxy-ethoxy (Ex. 32.16), hydroxy-ethoxy (Ex. 32.14), hydroxypropoxy (Ex. 32.17), 2-morpholin-4-yl-ethoxy (Ex. 32.19), dimethylamino-ethoxy (Ex. 32.20);

benzyloxy (Ex. 32.18);

dimethylamino (Ex. 1.50);

amino-carbonyl (Ex. 34);

tert.butyl amino carbonyl (Ex. 1.80);

heterocyclyl such as e.g. morpholin-4-yl (Ex. 1.79) Preferred compounds of formula I are those in which $R^1$ and $R^2$ signify lower-alkoxy, especially methoxy; $R^3$ signifies phenyl, or substituted phenyl or furyl, or lower-alkoxy. The compounds of formula I in which $R^3$ is different from hydrogen can be present in racemic form or as the R- or S-enantiomer. Examples of preferred compounds of formula I are:

A: (E)-(RS)-3-[5-(2,4-Diamino-pyrimidin-5-ylmethyl)-2,3-dimethoxy-phenyl]-1-(1-phenyl-1H-phthalazin-2-yl)-propenone; (Example 1.1), B: (E)-(RS)-3-[5-(2,4-Diamino-pyrimidin-5-ylmethyl)-2,3-dimethoxy-phenyl]-1-(1-furan-2-yl-1H-phthalazin-2-yl)-propenone; Example 1.4), C: (E)-(RS)-3-[5-(2,4-Diamino-pyrimidin-5-ylmethyl)-2,3-dimethoxy-phenyl]-1-[1-(4-hydroxymethyl-phenyl)-1H-phthalazin-2-yl]-propenone (Example 2.6), D: (E)-(RS)-3-[5-(2,4-Diamino-pyrimidin-5-ylmethyl)-2,3-dimethoxy-phenyl]-1-[1-(4-hydroxy-phenyl)-1H-phthalazin-2-yl]-propenone (Example 2.7), E: (E)-(RS)-3-[5-(2,4-Diamino-pyrimidin-5-ylmethyl)-2,3-dimethoxy-phenyl]-1-(1-ethyl-1H-phthalazin-2-yl)-propenone (Example 2.13), F: (E)-(RS)-3-[5-(2,4-Diamino-pyrimidin-5-ylmethyl)-2,3-dimethoxy-phenyl]-1-[1-(4-hydroxy-butyl)-1H-phthalazin-2-yl]-propenone (Example 2.20), and G: (E)-(RS)-3-{5-(2,4-Diamino-pyrimidin-5-ylmethyl)-2,3-dimethoxy-phennyl}-1-(1-propyl-1H-phthalazin-2-yl)-propenone; (Example 2.15), as well as the pharmaceutically acceptable salts of these compounds.

Furthermore, compounds of formula I are preferred wherein $R^3$ is pyridin-yl or pyrimidinyl which is substituted by lower alkyl such as e.g.

H: (E)-(R)-3-[5-(2,4-Diamino-pyrimidin-5-ylmethyl)-2,3-dimethoxy-phenyl]-1-[1-(6-methyl-pyridin-3-yl)-1H-phthalazin-2-yl]-propenone (Example 1.43), I: (E)-(RS)-3-[5-(2,4-Diamino-pyrimidin-5-ylmethyl)-2,3-dimethoxy-phenyl]-1-[1-(6-methyl-pyridin-3-yl)-1H-phthalazin-2-yl]-propenone (Example 1.48), J: (E)-(RS)-3-[5-(2,4-Diamino-pyrimidin-5-ylmethyl)-2,3-dimethoxy-phenyl]-1-[1-(6-ethyl-pyridin-3-yl)-1H-phthalazin-2-yl]-propenone (Example 34.1), and K: (E)-(RS)-3-[5-(2,4-Diamino-pyrimidin-5-ylmethyl)-2,3-dimethoxy-phenyl]-1-[1-(2-methyl-pyrimidin-5-yl)-1H-phthalazin-2-yl]-propenone (Example 32.5), as well as the pharmaceutically acceptable salts of these compounds.

The compounds of formula I form pharmaceutically acceptable acid addition salts with organic and inorganic acids. Examples of acid addition salts of compounds of formula I are salts with mineral acids, for example hydrohalic acids, such as hydrochloric acid, hydrogen bromide and hydrogen iodide, sulphuric acid, nitric acid, phosphoric acid and the like, salts with organic sulphonic acids, for example with alkyl- and aryl-sulphonic acids such as methanesulphonic, p-toluenesulphonic, benzen-sulphonic acid and the like, as well as salts with organic carboxylic acids, for example with acetic acid, tartaric acid, maleic acid, citric acid, benzoic acid, salicylic acid, ascorbic acid and the like.

The compounds of formula I and their pharmaceutically acceptable salts can be made in accordance with the invention by (a) reacting a compound of formula

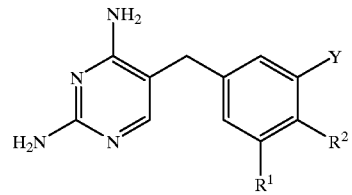

II wherein $R^1$ and $R^2$ are defined as above and Y is a leaving group, with a compound of formula

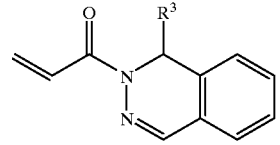

III wherein $R^3$ is as defined above, or (b) if desired, functionally modifying reactive groups present in the reaction product, or c) converting a compound of formula I into a pharmaceutically acceptable salt.

In order to make end products of formula I in accordance with process variant a) of the process in accordance with the invention, a so-called "Heck reaction" is carried out by e.g. reacting a starting compound of formula II in which the leaving group Y represents, for example, bromine, iodine, methanesulphonyloxy, trifluoromethanesulphonyloxy, benzenesulphonyloxy or p-toluenesulphonyloxy with a compound of general formula III. Preferably, an inert organic solvent, e.g. dioxan, tetrahydrofuran, N,N-dimethylacetamide or N,N-dimethylformamide, is used. The reaction is preferably effected in the presence of a base such as alkali metal carbonate or hydrogen carbonate, e.g. potassium carbonate or sodium hydrogen carbonate, and/or a tertiary amine, e.g. in a tri(lower alkyl)amine such as triethylamine, tri-n-butylamine or N-ethylpiperidine, and together with a catalyst, preferably a palladium complex, such as palladium(II) acetate, bis(triphenyl-phosphine) palladium(II) dichloride, bis(triphenyl-phosphine)palladium (TT) di acetate, tetrakis-triphenylphosphine palladium, or copper(I) iodide and triphenylphosphine or tri-o-tolylphosphine, optionally with the addition of a phase transfer catalyst such as a tetraalkylammonium salt, e.g. tetrabutylammonium bromide. The temperature of the "Heck reaction" preferably lies in the region between about 40° C. and the boiling point of the reaction mixture.

If desired, reactive groups present in the reaction product can be functionally modified in accordance with variant b) of the process in accordance with the invention. For example, in reaction products of formula I groups $R^3$ which contain alcohol functions can be transformed into an ester.

Making the salts of the compounds of formula I in accordance with variant c) can be effected in a manner known per se, e.g. by reacting a compound of formula I with an organic or inorganic acid, conveniently in a solvent such as acetone, ethanol, methanol or water.

The compounds of formula III can be obtained in accordance with the invention by a) reacting a compound of formula

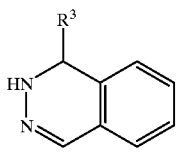

IV in which $R^3$ is as defined above with a reactive acrylic acid derivative.

Examples of reactive acrylic acid derivatives are the acid halides, especially the acid chloride, reactive amides, such as, for example, the imidazolide, and mixed anhydrides. The acylation in accordance with the invention can be carried out in an inert solvent, e.g. a hydrocarbon such as benzene or toluene, a chlorinated hydrocarbon such as chloroform or methylene chloride, or an ether such as dioxan or tetrahydrofuran, in the presence of a base, e.g. an amine such as pyridine or triethylamine (which can simultaneously serve as the solvent). The reaction temperature is not critical. The reaction is conveniently performed at temperatures between 0° C. and 50° C., especially at 0° C. to 30° C.;

or, especially in the case of compounds of formula III in which $R^3$ [is] a group of the formula —$CR^4R^{4'}COR^5$, by b) reacting a phthalazine in accordance with the following Reaction Scheme with a silyl enol ether of formula V of an enamine of formula VI in the presence of a reactive acrylic acid derivative such as, for example, the acid halide:

Reaction A

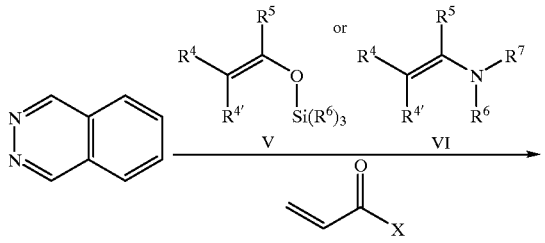

-continued

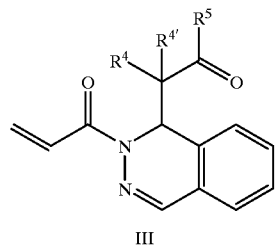

III wherein $R^4$ and $R^{4'}$ are each independently hydrogen, alkyl, aryl or heterocyclyl, $R^5$ is hydrogen, alkyl, alkoxy, aryl or hetrocyclyl, or $R^4$ and $R^5$ together form —$(CH_2)_n$—, n is a whole number between 2 to 5 inclusive, $R^6$ and $R^7$ are each lower alkyl, and $R^6$ and $R^7$ in the case of enamines of formula VI can also together form a ring, X is a halogen such as e.g. chlorine or bromine.

This reaction is preferably effected in inert solvents such as ether or in chlorinated hydrocarbons at temperatures of −20° C. to +20° C. with subsequent hydrolysis of the reaction product at 0 to 50° C.

The compounds of formula IV can be prepared in accordance with the following Reaction Scheme Reaction B

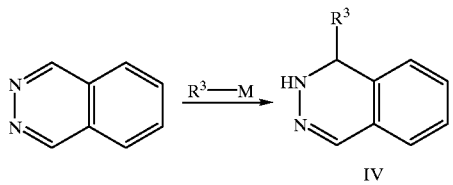

wherein $R^3$ is as defined above and

M is Li, Na, MgBr, MgCl or MgI.

This reaction is preferably effected in a temperature range of −80° C. to 20° C. An open-chain or cyclic ether such as diethyl ether or tetrahydrofuran is preferably used as the solvent.

As mentioned earlier, the compounds of formula I and their pharmaceutically acceptable salts possess valuable antibacterial properties. They are active against a large number of pathogenic microorganisms such as e.g. *Staphylococcus aureus, Pneumocystis carinii, Strepococcus pneumoniae* etc. by virtue of their activity in inhibiting bacterial dihydrofolate reductase (DHFR). The inhibition of this enzyme was taken as a measurement of the antibacterial activity. It is determined by the method of D. P. Baccanari and S. S. Joyner (Biochemistry 20, 1710 (1981)); see also P. G. Hartman et al., FEBS Letters 242, 157 (1988).

The $IC_{50}$-values (concentration at which the enzyme is inhibited by 50%) are determined by means of a graph.

The following Table contains inhibitory concentrations determined for representative members of the class of compound defined by formula I and determined in the above test. The $IC_{50}$ values (μM) against the purified DHFR of the reference strain *S. aureus* ATCC 25923, as well as against the purified DHFR of the multiresistant strain *S. aureus* 157/4696 are given. The third column shows $IC_{50}$ values (μM) against the purified DHFR of the multiresistant strain Streptococcus pneumoniae 1/1. The inhibition constants of trimethoprim are also given as a comparison.

| Example | S. aureus ATCC 25923 | S. aureus 157/4696 | S. pneumoniae 1/1 |
|---|---|---|---|
| Trimethoprim | 0.034 | 16.000 | 3.000 |
| A | 0.002 | 0.002 | 0.012 |
| B | 0.002 | 0.008 | 0.022 |
| C | 0.001 | 0.001 | 0.002 |
| D | 0.002 | 0.003 | 0.009 |
| E | 0.002 | 0.012 | 0.018 |
| F | 0.001 | 0.003 | 0.009 |
| G | 0.002 | 0.006 | 0.005 |
| H | 0.0003 | 0.0004 | 0.0012 |
| I | 0.0004 | 0.0004 | 0.0004 |
| J | 0.0003 | 0.0002 | 0.0015 |
| K | 0.0006 | 0.0006 | 0.0025 |

The products in accordance with the invention can be used as medicaments, e.g. in the form of pharmaceutical preparations for enteral or parenteral administration in a variety of unit dosage forms. For example, the products in accordance with the invention can be administered perorally, e.g. in the form of tablets, coated tablets, dragees, hard and soft gelatin capsules, solutions, emulsions or suspensions, rectally, e.g. in the form of suppositories, or parentally, e.g. in the form of injection solutions.

Making the pharmaceutical preparations can be affected in a manner which will be familiar to any person skilled in the art by bringing the substances in accordance with the invention, optionally in combination with other therapeutically valuable substances, into a galenical administration form together with suitable, non-toxic, inert therapeutically compatible solid or liquid carrier materials and, if desired, the usual pharmaceutical adjuvants.

Both inorganic and organic carrier materials are suitable as such carrier materials. Thus, for example, lactose, corn starch or derivatives thereof, talc, stearic acid or its salts can be used as carriers for tablets, coated tablets, dragees and hard gelatin capsules. Suitable carriers for soft gelatin capsules are, for example, vegetable oils, waxes, fats and semi-solid and liquid polyols (depending on the nature of the active ingredient no carriers are, however, required in the case of soft gelatin capsules). Suitable carrier materials for the production of solutions and syrups are, for example, water, polyols, sucrose, invert sugar and glucose. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols.

The usual preservatives, solubilizers, stabilizers, wetting agents, emulsifiers, sweeteners, colorants, flavorants, salts for varying the osmotic pressure, buffers, masking agents and antioxidants come into consideration as pharmaceutical adjuvants. For parenteral administration the compounds of formula I and, respectively, their salts are preferably provided as lyophilizates or dry powders for dilution with usual carriers such as water or isotonic saline.

As mentioned earlier, the compounds of formula I and their salts have antibacterial activity. They inhibit bacterial dihydrofolate reductase and potentiate the antibacterial activity of sulphonamides, such as e.g. sulfisoxazole, sulfadimethoxine, sulfamethoxazole, 4-sulphanilamido-5,6-dimethoxypyrimidine, 2-sulphanilamido-4,5-dimethylpyrimidine or sulfaquinoxaline, sulfadiazine, sulfamonomethoxine, 2-sulphanilamido-4,5-dimetlylisoxazole and other inhibitors of enzymes which are involved in folic acid biosynthesis, such as e.g. pteridine derivatives.

Oral, rectal and parenteral administration come into consideration in human medicine for such combinations of one or more compounds I in accordance with the invention with sulfonamides. The ratio of compound I to sulfonamide can vary within a broad range; it amounts to e.g. between 1:40 (parts by weight) and 1:1 (parts by weight); preferred ratios are 1:10 to 1:2.

Thus, e.g., a tablet can contain 80 mg of a compound I in accordance with the invention and 400 mg of sulfamethoxazole, a paediatric tablet can contain 20 mg of a compound I in accordance with the invention and 100 mg of sulfamethoxazole; syrup per 5 ml can contain 40 mg of compound I and 200 mg of sulfamethoxazole.

A daily dosage of about 0.2 g to about 2 g of a compound of formula I in accordance with the invention comes into consideration for adults.

The compounds of formula I are characterized by a high antibacterial activity and a pronounced synergetic affect in combination with sulfonamides and are well tolerated.

The following Examples illustrate the invention in more detail.

EXAMPLE 1

1.1. Preparation of (E)-(RS)-3-[5-(2,4-diamino-pyrimidin-5-ylmethyl)-2,3-dimethoxy-phenyl]-1-(1-phenyl-1H-phthalazin-2-yl)-propenone

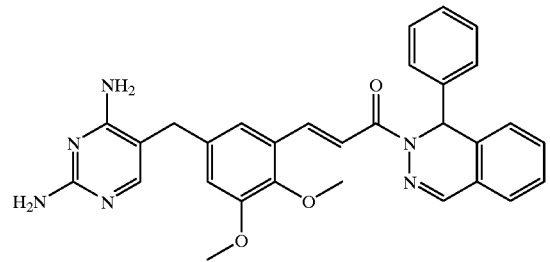

A solution 1.25 g of 5-(3-iodo-4,5-dimethoxy-benzyl)-pyrimidine-2,4-diamine and 45 mg of bis-(triphenylphosphine)-palladium(II) dichloride in 18 ml of N,N-dimethylformamide is heated to 120° C. and treated dropwise at this temperature with a solution of 850 mg of (RS)-1-(1-phenyl-1H-phthalazin-2-yl)-propenone in 7 ml of N,N-dimethylformamide and 4.5 ml of triethylamine. After a reaction period of 30 min. at 120° C. the dark mixture is concentrated on a rotary evaporator and the residue is chromatographed on 130 g of silica gel (eluent: methylene chloride/methanol/25% ammonia 95:5:0.5 v/v). The pure fractions are combined, concentrated and re-precipitated from ethyl acetate/hexane. 316 mg (19%) of (E)-(RS)-3-[5-(2,4-diamino-pyrimidin-5-ylmethyl)-2,3-dimethoxy-phenyl]-1-(1-phenyl-1H-phthalazin-2-yl)-propenone were isolated as a beige product, m.p. 130° C. The following compounds were prepared in analogy to Example 1.1.:

1.2. (E)-(RS)-3-[5-(2,4-Diamino-pyrimidin-5-ylmethyl)-2,3-dimethoxy-phenyl]1-(1-pyridin-2-yl-1H-phthalazin-2-yl)-propenone, m.p. 146° C.

1.3. (E)-(RS)-1-(1-Butyl-1H-phthalazin-2-yl)-3-[5-(2,4-diamino-pyrimidin-5-ylmethyl)-2,3-dimethoxy-phenyl]-propenone, m.p. 110° C., dec.

1.4. (E)-(RS)-3-[5-(2,4-Diamino-pyrimidin-5-ylmethyl)-2,3-dimethoxy-phenyl]-1-(1-furan-2-yl-1H-phthalazin-2-yl)-propenone, m.p. 140° C.

1.5. (E)-(RS)-3-[5-(2,4-Diamino-pyrimidin-5-ylmethyl)-2,3-dimethoxy-phenyl]-1-(1-thiazol-2-yl-1H-phthalazin-2-yl)-propenone, m.p. 145° C.

1.6. (E)-(RS)-2-(2-{3-[5-(2,4-Diamino-pyrimidin-5-ylmethyl)-2,3-dimethoxy-phenyl]-acryloyl}-1,2-dihydro-phthalazin-1-yl)-N,N-dimethyl-benzene-sulphonamide, m.p. 160° C.

1.7. (E)-(RS)-3-[5-(2,4-Diamino-pyrimidin-5-ylmethyl)-2,3-dimethoxy-phenyl]-1-[1-(2-dimethylaminomethyl-phenyl)-1H-phthalazin-2-yl]-propenone, m.p. 106° C., dec.

1.8. (E)-(RS)-3-[5-(2,4-Diamino-pyrimidin-5-ylmethyl)-2,3-dimethoxy-phenyl]-1-[1-(5-methyl-pyridin-2-yl)-1H-phthalazin-2-yl]-propenone, MS (ISP): 536 (M+H)$^+$.

1.9. (E)-(RS)-2-(2-{3-[5-(2,4-Diamino-pyrimidin-5-ylmethyl)-2,3-dimethoxy-phenyl]-acryloyl}-1,2-dihydro-phthalazin-1-yl)-cyclopentanone (mixture of diastereomers), MS (ISP): 527 (M+H)$^+$.

1.10. (E)-(RS)-2-(2-{3-[5-(2,4-Diamino-pyrimidin-5-ylmethyl)-2,3-dimethoxy-phenyl]-acryloyl}-1,2-dihydro-phthalazin-1-yl)-cyclohexanone (mixture of diastereomers), MS (ISP): 541 (M+H)$^+$.

1.11. (E)-(RS)-3-[5-(2,4-Diamino-pyrimidin-5-ylmethyl)-2,3-dimethoxy-phenyl]-1-[1-(2-oxo-propyl)-1H-phthalazin-2-yl]-propenone, MS (ISP): 501 (M+H)$^+$.

1.12. Methyl (E)-(RS)-2-(2-{3-[5-(2,4-Diamino-pyrimidin-5-ylmethyl)-2,3-dimethoxy-phenyl]-acryloyl}-1,2-dihydro-phthalazin-1-yl)-2-methyl-propionate, MS (ISP): 545 (M+H)$^+$.

1.13. (E)-(RS)-3-[5-(2,4-Diamino-pyrimidin-5-ylmethyl)-2,3-dimethoxy-phenyl]-1-[1-(2-oxo-2-phenyl-ethyl)-1H-phthalazin-2-yl]-propenone, MS (ISP): 563 (M+H)$^+$.

1.14. (E)-(RS)-3-(2-{3-[5-(2,4-Diamino-pyrimidin-5-ylmethyl)-2,3-dimethoxy-phenyl]-acryloyl}-1,2-dihydro-phthalazin-1-yl)-tetrahydro-pyran-2-one (mixture of diastereomers), MS (ISP): 543 (M+H)$^+$.

1.15. (E)-(RS)-3-[5-(2,4-dDiamino-pyrimidin-5-ylmethyl)-2,3-dimethoxy-phenyl]-1-[1-(1-methyl-2-oxo-2-phenyl-ethyl)-1H-phthalazin-2-yl]-propenone (mixture of diastereomers), MS (ISP): 577 (M+H)$^+$.

1.16. (E)-(RS)-3-[5-(2,4-Diamino-pyrimidin-5-ylmethyl)-2,3-dimethoxy-phenyl]-1-[1-(2-furan-2-yl-2-oxo-ethyl)-1H-phthalazin-2-yl]-propenone, MS (ISP): 553 (M+H)$^+$.

1.17. (E)-(RS)-3-[5-(2,4-Diamino-pyrimidin-5-ylmethyl)-2,3-dimethoxy-phenyl]-1-(1-methylsulfanylmethyl-1H-phthalazin-2-yl)-propenone, m.p.=205°.

1.18. (E)-(RS)-1-[1-(4-tert-Butyl-phenyl)-1H-phthalazin-2-yl]-3-[5-(2,4-diamino-pyrimidin-5-ylmethyl)-2,3-dimethoxy-phenyl]-propenone, m.p.=123°.

1.19. (E)-(RS)-3-[5-(2,4-Diamino-pyrimidin-5-ylmethyl)-2,3-dimethoxy-phenyl]-1-(1-p-tolyl-1H-phthalazin-2-yl)-propenone, m.p.=145°.

1.20. (E)-(RS)-3-[5-(2,4-Diamino-pyrimidin-5-ylmethyl)-2,3-dimethoxy-phenyl]-1-[1-(4-ethyl-phenyl)-1H-phthalazin-2-yl]-propenone, m.p.=107°.

1.21. (E)-(RS)-3-[5-(2,4-Diamino-pyrimidin-5-ylmethyl)-2,3-dimethoxy-phenyl]-1-[1-(4-trifluoromethoxy-phenyl)-1H-phthalazin-2-yl]-propenone, m.p.=127°.

1.22. (E)-(RS)-3-[5-(2,4-Diamino-pyrimidin-5-ylmethyl)-2,3-dimethoxy-phenyl]-1-[1-(3,4-dimethyl-phenyl)-1H-phthalazin-2-yl]-propenone, m.p.=1390.

1.23. (E)-(RS)-1-(1-tert-Butyl-1H-phthalazin-2-yl)-3-[5-(2,4-diamino-pyrimidin-5-ylmethyl)-2,3-dimethoxy-phenyl]-propenone, m.p.=90°.

1.24. (E)-(RS)-3-[5-(2,4-Diamino-pyrimidin-5-ylmethyl)-2,3-dimethoxy-phenyl]-1-[1-(5,6-dihydro-4H-pyran-2-yl)-1H-phthalazin-2-yl]-propenone, MS (ISP): 527.3 (M+H)$^+$.

1.25. (E)-(RS)-3-[5-(2,4-Diamino-pyrimidin-5-ylmethyl)-2,3-dimethoxy-phenyl]-1-[1-(2,4,6-trimethyl-phenyl)-1H-phthalazin-2-yl]-propenone, MS (ISP): 563.5 (M+H)$^+$.

1.26. (E)-R-(−)-3-[5-(2,4-Diamino-pyrimidin-5-ylmethyl)-2,3-dimethoxy-phenyl]-1-(1-phenyl-1H-phthalazin-2-yl)-propenone; $[\alpha]_D$=−661° (c=1; methanol).

1.27. (E)-S-(+)-3-[5-(2,4-Diamino-pyrimidin-5-ylmethyl)-2,3-dimethoxy-phenyl]-1-(1-phenyl-1H-phthalazin-2-yl)-propenone; $[\alpha]_D$=+664° (c=1 methanol).

1.28. (E)-S-(−)-3-[5-(2,4-Diamino-pyrimidin-5-ylmethyl)-2,3-dimethoxy-phenyl]-1-(1-furan-2yl-1H-phthalazin-2-yl)-propenone; $[\alpha]_D$=−543° (c=1 methanol).

1.29. (E)-R-(+)-3-[5-(2,4-Diamino-pyrimidin-5-ylmethyl)-2,3-dimethoxy-phenyl]-1-(1-furan-2yl-1H-phthalazin-2-yl)-propenone; $[\alpha]_D$=+580° (c=1; methanol).

1.30. (E)-R-(−)-3-[5-(2,4-Diamino-pyrimidin-5-ylmethyl)-2,3-dimethoxy-phenyl]-1-(1-propyl-1H-phthalazin-2-yl)-propenone; $[\alpha]_D$=−739° (c=1 methanol).

1.31. (E)-S-(+)-3-[5-(2,4-Diamino-pyrimidin-5-ylmethyl)-2,3-dimethoxy-phenyl]-1-(1-propyl-1H-phthalazin-2-yl)-propenone; $[\alpha]_D$=+790° (c=1 methanol).

1.32. (E)-R-(−)-3-[5-(2,4-Diamino-pyrimidin-5-ylmethyl)-2,3-dimethoxy-phenyl]-1-(1-methyl-1H-phthalazin-2-yl)-propenone; $[\alpha]_D$=−724° (c=1 methanol).

1.33. (E)-S-(+)-3-[5-(2,4-Diamino-pyrimidin-5-ylmethyl)-2,3-dimethoxy-phenyl]-1-(1-methyl-1H-phthalazin-2-yl)-propenone; $[\alpha]_D$=+689° (c=1 methanol).

1.34 (E)-(RS)-1-(1-Biphenyl-4-yl-1H-phthalazin-2-yl)-3-[5-(2,4-diamino-pyrimidin-5-ylmethyl)-2,3-dimethoxy-phenyl]-propenone, m.p. 147° C. (acetonitrile). MS (ISP): 597.3 (M+H)$^+$.

1.35 Mixture of (E)-3-[5-(2,4-Diamino-pyrimidin-5-ylmethyl)-2,3-dimethoxy-phenyl]-1-[(RS)- and -[(SR)-1-[4-[(RS)-1-ethoxy-ethoxy]-phenyl]-1H-phthalazin-2-yl]-propenone, m.p. 130° C. (ethanol). MS (ISP): 609.3 (M+H)$^+$.

1.36 (E)-1-[(RS)-1-Bicyclo[2.2.1]hept-2endo- and/or 2exo-yl-1H-phthalazin-2-yl]-3-[5-(2,4-diamino-pyrimidin-5-ylmethyl)-2,3-dimethoxy-phenyl]-propenone, m.p. 113–116° C. (methanol). MS (ISP): 539.4 (M+H)$^+$.

1.37 (E)-(RS)-3-[5-(2,4-Diamino-pyrimidin-5-ylmethyl)-2,3-dimethoxy-phenyl]-1-[1-(6-methyl-pyridin-2-yl)-1H-phthalazin-2-yl]-propenone, m.p. 134–138° C. (ethanol). MS (ISP): 536.3 (M+H)$^+$.

1.38 (E)-(RS)-3-[5-(2,4-Diamino-pyrimidin-5-ylmethyl)-2,3-dimethoxy-phenyl]-1-[1-(4-dimethylamino-phenyl)-1H-phthalazin-2-yl]-propenone, m.p. 270–275° C. (acetonitrile/methanol). MS (ISP): 564.4 (M+H)$^+$.

1.39 (E)-(RS)-3-[5-(2,4-Diamino-pyrimidin-5-ylmethyl)-2,3-dimethoxy-phenyl]-1-[1-[4-(2-ethoxy-ethoxy)-phenyl]-1H-phthalazin-2-yl]-propenone, m.p. 111–115° C. (ethanol). MS (ISP): 609.3 (M+H)$^+$.

1.40 (E)-(RS)-3-[5-(2,4-Diamino-pyrimidin-5-ylmethyl)-2,3-dimethoxy-phenyl]-1-(1-m-tolyl-1H-phthalazin-2-yl)-propenone, m.p. 134–139° C. (methanol). MS (ISP): 535.4 (M+H)$^+$.

1.41 (E)-(RS)-3-[5-(2,4-Diamino-pyrimidin-5-ylmethyl)-2,3-dimethoxy-phenyl]-1-[1-(3,5-dimethyl-phenyl)-1H-phthalazin-2-yl]-propenone, m.p. 134–137° C. (methanol). MS (ISP): 549.3 (M+H)$^+$.

1.42. (E)-(RS)-3-[5-(2,4-Diamino-pyrimidin-5-ylmethyl)-2,3-dimethoxy-phenyl]-1-[1-(4-pyrrol-1-yl-phenyl)-1H-phthalazin-2-yl]-propenone, m.p. 137–143° C. (ethanol). MS (ISP): 586.4 (M+H)$^+$.

1.43. (E)-(R)-3-[5-(2,4-Diamino-pyrimidin-5-ylmethyl)-2,3-dimethoxy-phenyl]-1-[1-(6-methyl-pyridin-3-yl)-1H-phthalazin-2-yl]-propenone, m.p. 140–143° C.

(acetonitrile), $[α]_D$=+6140 (c=1, chloroform). MS (ISP): 536.4 (M+H)⁺.

1.44 (E)-(S)-3-[5-(2,4-Diamino-pyrimidin-5-ylmethyl)-2,3-dimethoxy-phenyl]-1-[1-(6-methyl-pyridin-3-yl)-1H-phthalazin-2-yl]-propenone, m.p. 139–142° C. (acetonitrile/ethanol), $[α]_D$=−626° (c=1, chloroform). MS (ISP): 536.4 (M+H)⁺.

1.45 (E)-(RS)-3-[5-(2,4-Diamino-pyrimidin-5-ylmethyl)-2,3-dimethoxy-phenyl]-1-[1-(2,3-dihydro-benzo[1,4]dioxin-6-yl)-1H-phthalazin-2-yl]-propenone, m.p. 212–215° C. (methanol). MS (ISP): 579.2 (M+H)⁺.

1.46 (E)-(RS)-1-(1-Cyclopropyl-1H-phthalazin-2-yl)-3-[5-(2,4-diamino-pyrimidin-5-ylmethyl)-2,3-dimethoxy-phenyl]-propenone, m.p. 230–236° C. (acetonitrile/ethanol). MS (ISP): 485.4 (M+H)⁺.

1.47 (E)-(RS)-3-[5-(2,4-Diamino-pyrimidin-5-ylmethyl)-2,3-dimethoxy-phenyl]-1-[1-(4-methylsulfanyl-phenyl)-1H-phthalazin-2-yl]-propenone, m.p. 168–172° C. (acetonitrile). MS (ISP): 567.6 (M+H)⁺.

1.48 (E)-(RS)-3-[5-(2,4-Diamino-pyrimidin-5-ylmethyl)-2,3-dimethoxy-phenyl]-1-[1-(6-methyl-pyridin-3-yl)-1H-phthalazin-2-yl]-propenone, m.p. 153–156° C. (ethanol). MS (ISP): 536.4 (M+H)⁺.

1.49 (E)-(RS)-3-[5-(2,4-Diamino-pyrimidin-5-ylmethyl)-2,3-dimethoxy-phenyl]-1-(1-[1,3]dithian-2-yl-1H-phthalazin-2-yl)-propenone, m.p. 235–240° C. (acetonitrile). MS (ISP): 563.4 (M+H)⁺.

1.50 (E)-(RS)-3-[5-(2,4-Diamino-pyrimidin-5-ylmethyl)-2,3-dimethoxy-phenyl]-1-[1-(6-dimethylamino-pyridin-3-yl)-1H-phthalazin-2-yl]-propenone, m.p. 128–132° C. (methanol). MS (ISP): 565.4 (M+H)⁺.

1.51 (E)-(RS)-3-[5-(2,4-Diamino-pyrimidin-5-ylmethyl)-2,3-dimethoxy-phenyl]-1-(1-pyridin-3-yl-1H-phthalazin-2-yl)-propenone, mp. 138–142° C. (methanol), MS (ISP): 522.2 (M+H)⁺.

1.52 (E)-(R)-1-(1-Cyclopropyl-1H-phthalazin-2-yl)-3-[5-(2,4-diamino-pyrimidin-5-ylmethyl)-2,3-dimethoxy-phenyl]-propenone, m.p. 125–128° C. (methanol), $[α]_D$=+845° (c=1, chloroform). MS (ISP): 485.3 (M+H)⁺.

1.53 (E)-(S)-1-(1-Cyclopropyl-1H-phthalazin-2-yl)-3-[5-(2,4-diamino-pyrimidin-5-ylmethyl)-2,3-dimethoxy-phenyl]-propenone, m.p. 123–130° C. (methanol), $[α]_D$=−824° (c=0.1, chloroform). MS (ISP): 485.3 (M+H)⁺.

1.54 (E)-(R)-3-[5-(2,4-Diamino-pyrimidin-5-ylmethyl)-2,3-dimethoxy-phenyl]-1-[1-(4-methylsulfanyl-phenyl)-1H-phthalazin-2-yl]-propenone, m.p. 139–143° C. (acetonitril), $[α]_D$=+581° (c=1, chloroform). MS (ISP): 567.3 (M+H)⁺.

1.55 (E)-(S)-3-[5-(2,4-Diamino-pyrimidin-5-ylmethyl)-2,3-dimethoxy-phenyl]-1-[1-(4-methylsulfanyl-phenyl)-1H-phthalazin-2-yl]-propenone, m.p. 137–142° C. (acetonitrile), $[α]_D$=−590° (c=1, chloroform). MS (ISP): 567.4 (M+H)⁺.

1.56 (E)-(RS)-1-(1-Cyclobutyl-1H-phthalazin-2-yl)-3-[5-(2,4-diamino-pyrimidin-5-ylmethyl)-2,3-dimethoxy-phenyl]-propenone, m.p. 122–129° C. (methanol), MS (ISP): 499.3 (M+H)⁺.

1.57 (E)-(RS)-1-(1-Cyclopentyl-1H-phthalazin-2-yl)-3-[5-(2,4-diamino-pyrimidin-5-ylmethyl)-2,3-dimethoxy-phenyl]-propenone, m.p. 118–123° C. (methanol). MS (ISP): 513.4 (M+H)⁺.

1.58 (E)-(RS)-3-[5-(2,4-Diamino-pyrimidin-5-ylmethyl)-2,3-dimethoxy-phenyl]-1-[1-(4-trifluoromethyl-phenyl)-1H-phthalazin-2-yl]-propenone, m.p. 189–192° C. (methanol). MS (ISP): 589.3 (M+H)⁺.

1.59 (E)-(RS)-1-[1-(5-Chloro-pyridin-2-yl)-1H-phthalazin-2-yl]-3-[5-(2,4-diamino-pyrimidin-5-ylmethyl)-2,3-dimethoxy-phenyl]-propenone, m.p. 133° C. (methanol). MS (ISP): 556.2 (M+H)⁺.

1.60 (E)-(RS)-1-(1-Cyclohexyl-1H-phthalazin-2-yl)-3-[5-(2,4-diamino-pyrimidin-5-ylmethyl)-2,3-dimethoxy-phenyl]-propenone, m.p. 120° C. (methanol). MS (ISP): 527.3 (M+H)⁺.

1.61 (E)-(RS)-3-[5-(2,4-Diamino-pyrimidin-5-ylmethyl)-2,3-dimethoxy-phenyl]-1-[1-(4-methoxy-phenyl)-1H-phthalazin-2-yl]-propenone, m.p. 199–201° C. (methanol). MS (ISP): 551.2 (M+H)⁺.

1.62 (E)-(RS)-3-[5-(2,4-Diamino-pyrimidin-5-ylmethyl)-2,3-dimethoxy-phenyl]-1-[1-(3,4-dimethoxy-phenyl)-1H-phthalazin-2-yl]-propenone, m.p. 155° C. (methanol). MS (ISP): 581.3 (M+H)⁺.

1.63 (E)-(RS)-1-(1-Benzo[1,3]dioxol-5-yl-1H-phthalazin-2-yl)-3-[5-(2,4-diamino-pyrimidin-5-ylmethyl)-2,3-dimethoxy-phenyl]-propenone, m.p. 131–136° C. (methanol). MS (ISP): 565.3 (M+H)⁺.

1.64 (E)-(RS)-4-[2-[3-[5-(2,4-Diamino-pyrimidin-5-ylmethyl)-2,3-dimethoxy-phenyl]-acryloyl]-1,2-dihydro-phthalazin-1-yl]-benzonitril, m.p. 138–146° C. (methanol). MS (ISP): 546.2 (M+H)⁺.

1.65 (E)-(RS)-4-[2-[3-[5-(2,4-Diamino-pyrimidin-5-ylmethyl)-2,3-dimethoxy-phenyl]-acryloyl]-1,2-dihydro-phthalazin-1-yl]-benzoic acid tert-butyl ester, m.p. 165–169° C. (methanol). MS (ISP): 621.5 (M+H)⁺.

1.66 (E)-(RS)-3-[5-(2,4-Diamino-pyrimidin-5-ylmethyl)-2,3-dimethoxy-phenyl]-1-(1-thiophen-2-yl-1H-phthalazin-2-yl)-propenone, m.p. 150-155° C. (ethanol). MS (ISP): 527.3 (M+H)⁺.

1.67 (E)-(RS)-1-[1-(5-Butyl-thiophen-2-yl)-1H-phthalazin-2-yl]-3-[5-(2,4-diamino-pyrimidin-5-ylmethyl)-2,3-dimethoxy-phenyl]-propenone, m.p. 107–111° C. (methanol). MS (ISP): 583.3 (M+H)⁺.

1.68 mixture of (E)-3-[5-(2,4-diamino-pyrimidin-5-ylmethyl)-2,3-dimethoxy-phenyl]-1-[(RS)- and -[(SR)-1-[4-[(RS)-1-hydroxy-ethyl]-phenyl]-1H-phthalazin-2-yl]-propenone, m.p. 225–230° C. (methanol). MS (ISP): 565.4 (M+H)⁺.

1.69 (E)-(RS)-1-(1-Benzenesulfonylmethyl-1H-phthalazin-2-yl)-3-[5-(2,4-diamino-pyrimidin-5-ylmethyl)-2,3-dimethoxy-phenyl]-propenone, m.p. 128–133° C. (methanol). MS (ISP): 599.2 (M+H)⁺.

1.70 (E)-(RS)-4-[2-[3-[5-(2,4-Diamino-pyrimidin-5-ylmethyl)-2,3-dimethoxy-phenyl]-acryloyl]-1,2-dihydro-phthalazin-1-yl]-N,N-dimethyl-benzenesulfonamid, m.p. 133–135° C. (methylenchloride/methanol). MS (ISP): 628.3 (M+H)⁺.

1.71 (E)-(RS)-3-[5-(2,4-Diamino-pyrimidin-5-ylmethyl)-2,3-dimethoxy-phenyl]-1-[1-(4-methoxymethyl-phenyl)-1H-phthalazin-2-yl]-propenone, m.p. 165–167° C. (methanol). MS (ISP): 565.4 (M+H)⁺.

1.72 (E)-(RS)-3-[5-(2,4-Diamino-pyrimidin-5-ylmethyl)-2,3-dimethoxy-phenyl]-1-[1-[4-[(diisopropylamino)-methyl]-phenyl]-1H-phthalazin-2-yl]-propenone, m.p. 139–144° C. (methanol). MS (ISP): 634.4 (M+H)⁺.

1.73 (E)-(RS)-1-[1-(4-Chloro-phenyl)-1H-phthalazin-2-yl]-3-[5-(2,4-diamino-pyrimidin-5-ylmethyl)-2,3-dimethoxy-phenyl]-propenone, m.p. 158–160° C. (acetonitrile). MS (ISP): 555.2 (M+H)⁺.

1.74 (E)-(RS)-3-[5-(2,4-Diamino-pyrimidin-5-ylmethyl)-2,3-dimethoxy-phenyl]-1-[1-(6-methoxy-pyridin-3-yl)-1H-phthalazin-2-yl]-propenone, m.p. 124–130° C. (methanol). MS (ISP): 552.3 (M+H)⁺.

1.75 (E)-(RS)-3-[5-(2,4-Diamino-pyrimidin-5-ylmethyl)-2,3-dimethoxy-phenyl]-1-[1-[4-(4-methyl-piperazin-1-ylmethyl)-phenyl]-1H-phthalazin-2-yl]-propenone, m.p. 145° C. MS (ISP): 633.4 (M+H)⁺.

1.76 (E)-(RS)-3-[5-(2,4-Diamino-pyrimidin-5-ylmethyl)-2,3-dimethoxy-phenyl]-1-[1-(4-morpholin-4-ylmethyl-phenyl)-1H-phthalazin-2-yl]-propenone, m.p. 85–88° C. (ethanol). MS (ISP): 620.4 (M+H)⁺.

1.77 (E)-(RS)-1-(1-Adamantan-2-yl-1H-phthalazin-2-yl)-3-[5-(2,4-diamino-pyrimidin-5-ylmethyl)-2,3-dimethoxy-phenyl]-propenone, m.p. 185–188° C. (methylenchloride/methanol). MS (ISP): 579.3 (M+H)⁺.

1.78 (E)-(RS)-3-[5-(2,4-Diamino-pyrimidin-5-ylmethyl)-2,3-dimethoxy-phenyl]-1-{1-[6-(1-hydroxy-1-methyl-ethyl)-pyridin-3-yl]-1H-phthalazin-2-yl}-propenone, m.p. 147–152° C. (ethanol). MS (ISP): 580.2 (M+H)⁺.

1.79 (E)-(RS)-3-[5-(2,4-Diamino-pyrimidin-5-ylmethyl)-2,3-dimethoxy-phenyl]-1-[1-(6-morpholin-4-yl-pyridin-3-yl)-1H-phthalazin-2-yl]-propenone, m.p. 142–148° C. (ethanol). MS (ISP): 607.2 (M+H)⁺.

1.80 (E)-(RS)-5-(2-{3-[5-(2,4-Diamino-pyrimidin-5-ylmethyl)-2,3-dimethoxy-phenyl]-acryloyl}-1,2-dihydro-phthalazin-1-yl)-pyridin-2-carbonic acid tert-butylamide, m.p. 140–148° C. (methylenchlorid/methanol). MS (ISP): 621.2 (M+H)⁺.

Example 2

2.1. Preparation of (E)-(RS)-3-[5-(2,4-diamino-pyrimidin-5-ylmethyl)-2,3-dimethoxy-phenyl]-1-[1-(4-fluoro-phenyl)-1H-phthalazin-2-yl]-propenone

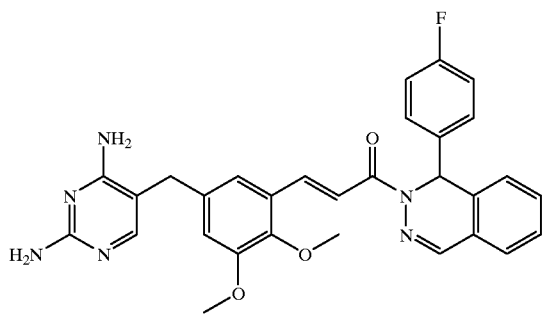

A solution of 0.819 g of 5-(3-iodo-4,5-dimethoxy-benzyl)-pyrimidin-2,4-diamine and 0.89 g of (RS)-1-[1-(4-fluoro-phenyl)-1H-phthalazin-2-yl]-propenone in 15 ml of N,N-dimethylacetamide and 1.9 ml of triethylamine is treated with 22 mg of palladium-(II) acetate and 127 mg of tri-o-tolylphosphine and heated to 120° C. for 2.5 hrs. Subsequently, the hot orange solution is poured into 50 ml of aqueous saturated sodium hydrogen carbonate solution and stirred at room temperature for 15 min. The resulting precipitate is filtered off under suction dried and chromatographed over silica gel with dichloromethane/methanol 95:5. The pure fractions are combined, concentrated and crystallized from dichloromethane/tert.butyl methyl ether. 603 mg (53%) of E)-(RS)-3-[5-(2,4-diamino-pyrimidin-5-ylmethyl)-2,3-dimethoxy-phenyl]-1-[1-(4-fluoro-phenyl)-1H-phthalazin-2-yl]-propenone are isolated as a colorless product, m.p. 114° C., dec.

The following compounds were prepared in analogy to Example 2.1.:

2.2. (E)-(RS)-3-[5-(2,4-Diamino-pyrimidin-5-ylmethyl)-2,3-dimethoxy-phenyl]-1-[1-(2,4-difluoro-phenyl)-1H-phthalazin-2-yl]-propenone, m.p. 121° C., dec.

2.3. (E)-(RS)-3-[5-(2,4-Diamino-pyrimidin-5-ylmethyl)-2,3-dimethoxy-phenyl]-1-(1-tridecafluorohexyl-1H-phthalazin-2-yl)-propenone, m.p. 143° C., dec.

2.4. (E)-3-[5-(2,4-Diamino-pyrimidin-5-ylmethyl)-2,3-dimethoxy-phenyl]-1-(1H-phthalazin-2-yl)-propenone, m.p. 164° C., dec.

2.5. (E)-(RS)-1-(1-Phenylsulphinylmethyl-1H-phthalazin-2-yl)-3-[5-(2,4-diamino-pyrimidin-5-ylmethyl)-2,3-dimethoxy-phenyl]-propenone, m.p. 135–138° C.

2.6. (E)-(RS)-3-{5-(2,4-Diamino-pyrimidin-5-ylmethyl)-2,3-dimethoxy-phenyl}-1-{1-(4-hydroxymethyl-phenyl)-1H-phthalazin-2-yl}-propenone, m.p 265° C.

2.7. (E)-(RS)-3-{5-(2,4-Diamino-pyrimidin-5-ylmethyl)-2,3-dimethoxy-phenyl}-1-{1-(4-hydroxy-phenyl)-1H-phthalazin-2-yl}-propenone, MS (ISP): 537.3 (M+H)⁺

2.8. (E)-(RS)-3-(5-(2,4-Diamino-pyrimidin-5-ylmethyl)-2,3-dimethoxy-phenyl}-1-{1-(2-hydroxymethyl-phenyl)-1H-phthalazin-2-yl}-propenone. M.p. 259° C.

2.9. (E)-(RS)-3-{5-(2,4-Diamino-pyrimidin-5-ylmethyl)-2,3-dimethoxy-phenyl}-1-{1-(3-hydroxymethyl-phenyl)-1H-phthalazin-2-yl}-propenone. M.p. 178–79° C.

2.10. (E)-(RS)-3-{5-(2,4-Diamino-pyrimidin-5-ylmethyl)-2,3-dimethoxy-phenyl}-1-{1-(3-hydroxy-phenyl)-1H-phthalazin-2-yl}-propenone. M.p. 169–171° C.

2.11. (E)-(RS)-3-{5-(2,4-Diamino-pyrimidin-5-ylmethyl)-2,3-dimethoxy-phenyl}-1-(1-methyl-1H-phthalazin-2-yl)-propenone. M.p. 226° C.

2.12. (E)-(RS)-3-{5-(2,4-Diamino-pyrimidin-5-ylmethyl)-2,3-dimethoxy-phenyl}-1-{1(4-(2-hydroxyethyl)-phenyl)-1H-phthalazin-2-yl}-propenone. M.p. 260° C.

2.13. (E)-(RS)-3-{5-(2,4-Diamino-pyrimidin-5-ylmethyl)-2,3-dimethoxy-phenyl}-1-(1-ethyl-1H-phthalazin-2-yl)-propenone. MS (ISP): 473.4 (M+H)⁺

2.14. (E)-(RS)-3-{5-(2,4-Diamino-pyrimidin-5-ylmethyl)-2,3-dimethoxy-phenyl}-1-{1-(4-carbamoyloxymethyl-phenyl)-1H-phthalazin-2-yl}-propenone. MS (ISP): 594.4 (M+H)⁺

2.15. (E)-(RS)-3-{5-(2,4-Diamino-pyrimidin-5-ylmethyl)-2,3-dimethoxy-phenyl}-1-(1-propyl-1H-phthalazin-2-yl)-propenone. MS (ISP): 487.4 (M+H)⁺

2.16. (E)-(RS)-3-{5-(2,4-Diamino-pyrimidin-5-ylmethyl)-2,3-dimethoxy-phenyl}-1-(1-prop-2-yl-1H-phthalazin-2-yl)-propenone. MS (ISP): 487.4 (M+H)⁺

2.17. (E)-(RS)-3-{5-(2,4-Diamino-pyrimidin-5-ylmethyl)-2,3-dimethoxy-phenyl}-1-{1-(3-methyl-butyl)-1H-phthalazin-2-yl}-propenone. MS (ISP): 515.5 (M+H)⁺

2.18. (E)-(RS)-3-{5-(2,4-Diamino-pyrimidin-5-ylmethyl)-2,3-dimethoxy-phenyl}-1-(3-hydroxy-prop-1-yl-1H-phthalazin-2-yl)-propenone. MS (ISP): 503.3 (M+H)⁺

2.19. (E)-(RS)-Morpholine-4-carboxylic acid 4-(2-{3-[5-(2,4-diamino-pyrimidin-5-ylmethyl)-2,3-dimethoxy-phenyl]-acryloyl}-1,2-dihydro-phthalazin-1-yl)-butyl ester. MS (ISP): 630.4 (M+H)⁺

2.20. (E)-(RS)-3-{5-(2,4-Diamino-pyrimidin-5-ylmethyl)-2,3-dimethoxy-phenyl}-1-{(4-hydroxy-but-1-yl)-1H-phthalazin-2-yl}-propenone. MS (ISP): 517.3 (M+H)⁺

2.21. (E)-(RS)-Carbamic acid 4-(2-{3-[5-(2,4-diamino-pyrimidin-5-ylmethyl)-2,3-dimethoxy-phenyl]-acryloyl}-1,2-dihydro-phthalazin-1-yl)-butyl ester. MS(ISP): 560.3 (M+H)⁺

2.22. (E)-(RS)-Carbamic acid 4-(2-{3-[5-(2,4-diamino-pyrimidin-5-ylmethyl)-2,3-dimethoxy-phenyl]-acryloyl}-1,2-dihydro-phthalazin-1-yl)-propyl ester. MS (ISP): 546.3 (M+H)⁺

2.23. (E)-(RS)-3-[5-(2,4-Diamino-pyrimidin-5-ylmethyl)-2,3-dimethoxy-phenyl]-1-[1-(2-[1,3]dioxolan-2-yl-ethyl)-1H-phthalazin-2-yl)-propenone. MS (ISP): 545.3 (M+H)⁺

2.24. (E)-(RS)-1-Cyclohexylmethyl-1H-phthalazin-2-yl)-3-[5-(2,4-diamino-pyrimidin-5-ylmethyl)-2,3-dimethoxy-phenylpropenone. MS (ISP): 541.4 (M+H)⁺

Example 3

3.1. Preparation of (E)-(RS)-3-[5-(2,4-diamino-pyrimidin-5-ylmethyl)-3-methoxy-2-methoxymethoxy-phenyl]-1-(1-phenyl-1H-phthalazin-2-yl)-propenone

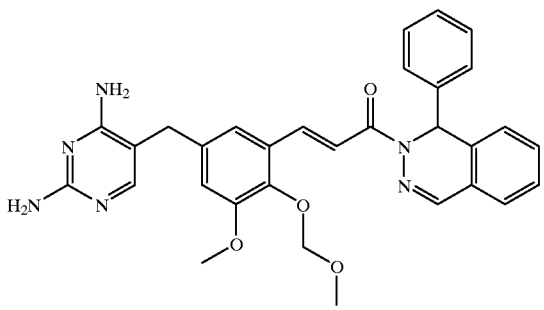

A solution of 806 mg of 5-(3-iodo-5-methoxy-4-methoxymethoxy-benzyl)-pyrimidine-2,4-diamine and 28 mg of bis-(triphenylphosphine)-palladium-(II) dichloride in 11 ml of N,N-dimethylformamide is heated to 120° C. and treated dropwise at this temperature with a solution of 524 mg of (RS)-1-(1-phenyl-1H-phthalazin-2-yl)-propenone in 4 ml of N,N-dimethylformamide and 2.8 ml of triethylamine. After a reaction period of 3 hrs. at 120° C. the dark mixture is concentrated and the residue is chromatographed on 330 g of silica gel (eluent: methylene chloride/methanol 1:1 v/v). The pure fractions are combined. After isolation by concentration there are obtained 500 mg of (E)-(RS)-3-[5-(2,4-diamino-pyrimidin-5-ylmethyl)-3-methoxy-2-methoxymethoxy-phenyl]-1-(1-phenyl-1H-phthalazin-2-yl)-propenone as a yellowish foam. MS (ISP): 551 (M+H)+.
The following compounds were prepared in analogy to example 3:

3.2. (E)-(RS)-3-[5-(2,4-Diamino-pyrimidin-5-ylmethyl)-3-methoxy-2-methoxymethoxy-phenyl]-1-(1-furan-2-yl-1H-phthalazin-2-yl)-propenone, MS (ISP): 541 (M+H)+.

3.3. (E)-(RS)-3-[5-(2,4-Diamino-pyrimidin-5-ylmethyl)-3-methoxy-2-methoxymethoxy-phenyl]-1-[1-(4-hydroxymethyl-phenyl)-1H-phthalazin-2-yl]-propenone, MS (ISP): 581 (M+H)+.

Example 4
Preparation of (E)-(RS)-3-{5-(2,4-diamino-pyrimidin-5-ylmethyl)-2,3-dimethoxy-phenyl}-1-{1[2-(2,2-dimethyl-[1,3]-dioxolan-4-yl)-ethyl]-1H-phthalazin-2-yl}-propenone

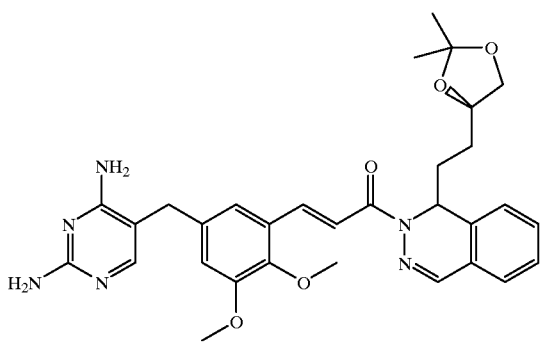

A solution of 1.3 g of 5-(3-iodo-4,5-dimethoxy-benzyl)-pyrimidin-2,4-diamine, 100 mg of bis-(triphenylphosphine)-palladium-(II) dichloride, 1.1 g of sodium bicarbonate, 4.7 ml of triethylamaine and 1.2 g of (E)-(RS)-1-{1[2,2-dimethyl-[1,3]-dioxolan-4-yl]-ethyl}-1H-phthalazin-2-yl}-propenone in 25 ml of dimethylformamide is heated to 120° C. After 5 hrs. the pale yellow mixture is concentrated on a rotary evaporator and the residue is chromatographed on silica gel (eluent: CH₂Cl₂/MeOH/NH₄OH: 95/5/0.5). The pure fractions are combined, concentrated and crystallized from CH₂Cl₂. 720 mg of (E)-(RS)-3-{5-(2,4-diamino-pyrimidin-5-ylmethyl)-2,3-dimethoxy-phenyl}-1-{1[2-(2,2-dimetlhyl-[1,3]-dioxolan-4-yl)-ethyl]-1H-phthalazin-2-yl}-propenone are isolated as a beige product. MS (ISP): 573.5 (M+H)+

Example 5
Preparation of (E)-(RS)-3-[5-(2,4-diamino-pyrimidin-5-ylmethyl)-3-methoxy-2-(2-morpholin-4-yl-ethoxy)-phenyl]-1-(1-phenyl-1H-phthalazin-2-yl)-propenone

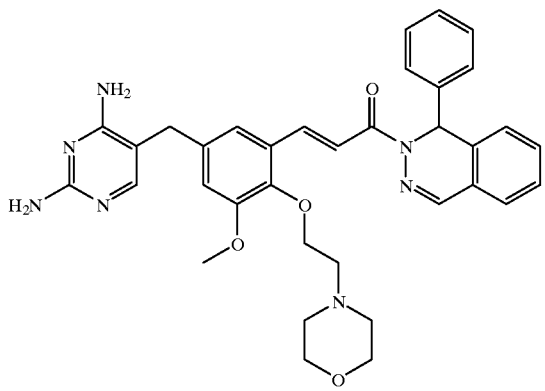

A solution of 120 mg of 5-{3-iodo-5-methoxy-4-(2-morpholin-4-yl-ethoxy)-benzyl}-pyrimidine-2,4-diamine and 28 mg of bis-(triphenylphosphine)-palladium-(II) dichloride in 1.5 ml of N,N-dimethylformamide is heated to 120° C. and treated dropwise at this temperature with a solution of 76 mg of (RS)-1-(1-phenyl-1H-phthalazin-2-yl)-propenone in 0.75 ml of N,N-dimethyl-formamide and 0.75 ml of triethylamine. After 2.5 hrs. at 120° C. the dark reaction mixture is concentrated and the residue is chromatographed on 50 g of silica gel (eluent, methylene chloride/methanol 1:1 v/v). The pure fractions are combined. 54 mg of (E)-(RS)-3-[5-(2,4-diamino-pyrimidin-5-ylmethyl)-3-methoxy-2-(2-morpholin-4-yl-ethoxy)-phenyl]-1-(1-phenyl-1H-phthalazin-2-yl)-propenone are isolated as a yellowish foam. MS (ISP): 620(M+H)+.

Example 6
Preparation of methyl (E)-(RS)-{4-(2,4-diamino-pyrimidin-5-ylmethyl)-2-methoxy-6-{3-oxo-3-(1-phenyl-1-H-phthalazin-2-yl)-propenyl}-phenoxy}-acetate

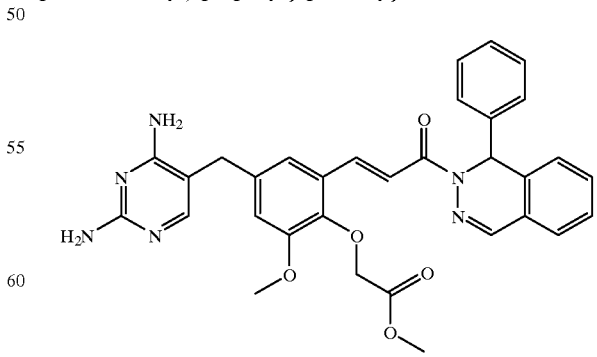

A solution of 380 mg of methyl {4-(2,4-diamino-pyrimidin-5-ylmethyl)-2-iodo-6- methoxy-phenoxy}-acetate and 96 mg of bis-(triphenylphosphine)-palladium-(II)dichloride in 5 ml of N,N-dimethylformamide is heated to 120° C. and treated dropwise at this temperature with a solution of 250 mg of (RS)-1-(1-phenyl-1H-phthalazin-2-yl)-propenone in 2.5 ml of N,N-dimethyl-formamide and 2.5 ml of triethylamine. After 2.5 hrs. at 120° C. the dark reaction mixture is concentrated and the residue is chromatographed on 100 g of silica gel (eluent: methylene chloride/methanol 1:1 v/v). The pure fractions are combined. 268 mg of methyl (E)-(RS)-{4-(2,4-diamino-pyrimidin-5-ylmethyl)-2-methoxy-6-{3-oxo-3-(1-phenyl-1-H-phthalazin-2-yl)-propenyl}-phenoxy}-acetate are isolated as a yellowish foam. MS (ISP): 579 (M+H)⁺.

Example 7

Preparation of (E)-(RS)-2-(2-{3-[5-(2,4-diamino-pyrimidin-5-ylmethyl)-2,3-dimethoxy-phenyl -acryloyl}-1,2-dihydro-phthalazin-1-yl)-2-methyl-propionic acid

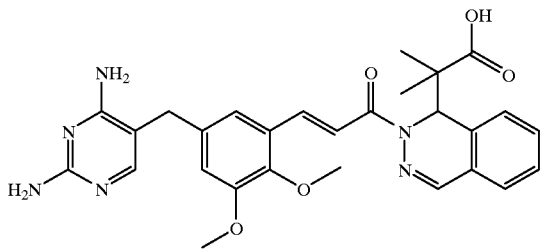

To the solution of 50 mg of methyl (E)-(RS)-2-(2-{3-[5-(2,4-diamino-pyrimidin-5-ylmethyl)-2,3-dimethoxy-phenyl -acryloyl}-1,2-dihydro-phthalazin-1-yl)-2-methyl-propionate (Example 1.12) in 5 ml of methanol are added 3 drops of 2N sodium hydroxide solution and the mixture is held at reflux for 45 min. Subsequently, the mixture is concentrated, the residue is treated with ice-water and neutralized with 2N hydrochloric acid. The insoluble material is recrystallized from methylene/methanol. 41 mg of (E)-(RS)-2-(2-{3-[5-(2,4-diamino-pyrimidin-5-ylmethyl)-2,3-dimethoxy-phenyl]-acryloyl}-1,2-dihydro-phthalazin-1-yl)-2-methyl-propionic acid are isolated as a colorless solid. M.p=245° C., dec.

Example 8

8.1. Preparation of (E)-(RS)-3-[5-(2,4-diamino-pyrimidin-5-ylmethyl)-2-hydroxy-3-methoxy-phenyl]-1-(1-phenyl-1H-phthalazin-2-yl)-propenone

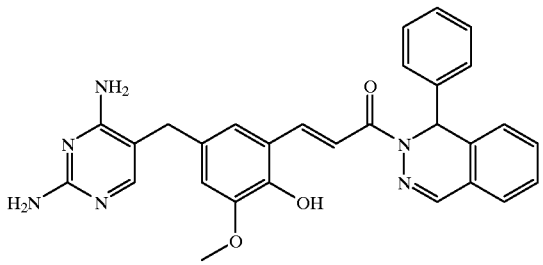

290 mg of (E)-(RS)-3-[5-(2,4-diamino-pyrimidin-5-ylmethyl)-3-methoxy-2-methoxymethoxy-phenyl]-1-(1-phenyl-1H-phthalazin-2-yl)-propenone; Example 3.1. are dissolved in 10 ml of methanol and treated with 10 drops of conc. hydrochloric acid. After one hour at 70° C. the mixture is concentrated and the residue is chromatographed on 250 g of silica gel (eluent: methylene chloride/methanol). 228 mg of (E)-(RS)-3-[5-(2,4-diamino-pyrimidin-5-ylmethyl)-2-hydroxy-3-methoxy-phenyl]-1-(1-phenyl-1H-phthalazin-2-yl)-propenone are isolated as an orange, hygroscopic solid. MS (ISP): (M+H)⁺

The following compounds were prepared in analogy to 8.1.:

8.2. (E)-(RS)-3-[5-(2,4-Diamino-pyrimidin-5-ylmethyl)-2-hydroxy-3-methoxy-phenyl]-1-(1-furan-2-yl-1H-phthalazin-2-yl)-propenone, m.p. 158° C., dec.

8.3. (E)-(RS)-3-[5-(2,4-Diamino-pyrimidin-5-ylmethyl)-2-hydroxy-3-methoxy-phenyl]-1-[1-(4-hydroxymethyl-phenyl)-1H-phthalazin-2-yl]-propenone, m.p.>250° C.

Example 9

9.1. Preparation of 2-amino-propionic acid 4-(2-{3-[5-(2,4-diamino-pyrimidin-5-ylmethyl)-2,3-dimethoxy-phenyl -acryloyl}-1,2-dihydro-phthalazin-1-yl)-benzyl ester

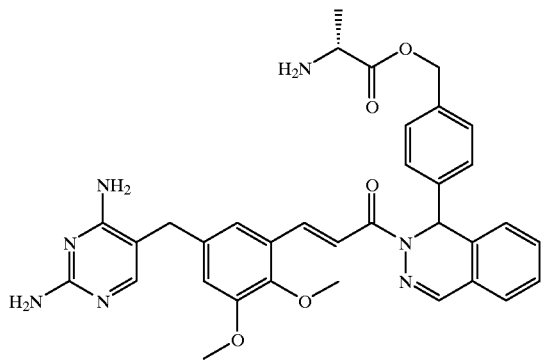

A solution of 130 mg of 2-tert-butoxycarbonylamino-propionic acid 4-(2-(3-[5-(2,4-diamino-pyrimidin-5-ylmethyl)-2,3-dimethoxy-phenyl]-acryloyl)-1,2-dihydro-phthalazin-1-yl)-benzyl ester in 20 ml of trifluoroethanol is treated with 18 μl of methanesulphonic acid at room temperature over one hour. The reaction solution is concentrated, the residue is taken up in ethyl acetate and filtered. The crystals are dissolved in 5 ml of water and treated with 20 ml of pH 7 buffer. The suspension obtained is suction filtered. There are obtained 65 mg of 2-amino-propionic acid 4-(2-{3-[5-(2,4-diamino-pyrimidin-5-ylmethyl)-2,3-dimethoxy-phenyl]-acryloyl)-1,2-dihydro-phthalazin-1-yl)-benzyl ester, MS (ISP): 622.3 (M+H)⁺

The educt used in Example 9.1. is prepared as follows:

a) A solution of 275 mg of (E)-(RS)-3-{5-(2,4-diamino-pyrimidin-5-ylmethyl)-2,3-dimethoxy-phenyl}-1-{1-(4-hydroxymethyl-phenyl)-1H-phthalazin-2-yl)-propenone in 10 ml of dimethylformamide is treated at room temperature with 105 mg of BOC-L-alanine, 95 mg of N-(3-dimethylaminopropyl-N'-ethylcarbodiimide hydrochloride and 30 mg of 4-dimethyl aminopyridine. After one hour the reaction solution is concentrated and the residue is chromatographed on silica gel (eluent: dichloromethane/ethanol 9/1). 220 mg (61%) of 2-tert-butoxycarbonylamino-propionic acid-4-(2-(3-[5-(2,4-diamino-pyrimidin-5-ylmethyl)-2,3-dimethoxy-phenyl]-acryloyl}-1,2-dihydro-phthalazin-1-yl)-benzyl ester are obtained as a pale yellow solid, MS (ISP) 722.5 (M+H)⁺

9.2. 2-Amino-5-guanidino-pentanoic acid 4-(2-{3-[5-(2,4-diamino-pyrimidin-5-ylmethyl)-2,3-dimethoxy-phenyl]-acryloyl}-1,2-dihydro-phthalazin-1-yl)-benzyl ester is prepared in analogy to Example 9.1. MS (ISP): 707.6 (M+H)⁺.

The educt used in Example 9.2 is prepared in analogy to Example 9.1.a) from a 1:1 mixture of (S)-5-(N,N'-bis-tert-butoxycarbonyl-guanidino)-2-tert-butoxycarbonylaminopentanoic acid (E)-(R)-and -(S)-4-[2-[3-[5-(2,4-diamino-pyrimidin-5-ylmethyl)-2,3-dimethoxy-phenyl]-acryloyl]-1,2-dihydro-phthalazin-1-yl]-benzyl ester. MS (ISP): 1007.9 (M+H)$^+$ Example 10

10.1. Preparation of sulphuric acid (E)-(RS)-mono-[4-[2-[3-[5-(2,4-diamino-pyrimidin-5-ylmethyl)-2,3-dimethoxy-phenyl]-acryloyl]-1,2-dihydro-phthalazin-1-yl]-benzyl ester] Na salt (1:1)

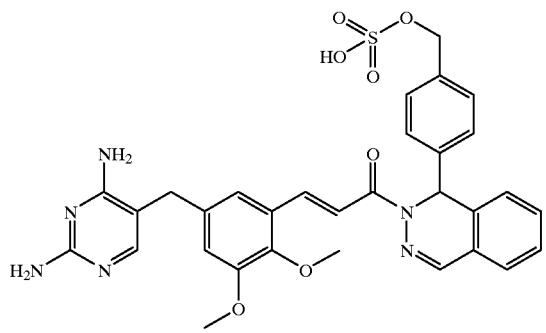

A solution 200 mg of (E)-(RS)-3-{5-(2,4-diamino-pyrimidin-5-ylmethyl)-2,3-dimethoxy-phenyl}-1-{1-(4-hydroxymethyl-phenyl)-1H-phthalazin-2-yl}-propenone in 5 ml of dimethylformamide is treated at room temperature with 67 mg of sulphur trioxide-dimethylformamide complex. After 1 hour 73 mg of sodium bicarbonate and 5 ml of water are added. The solution is stirred for a further hour, thereafter the solution is concentrated, the residue is taken up in 40 ml of methanol/dichloromethane and filtered. The mother liquor is concentrated and the residue is crystallized from methanol. There are obtained 90 mg of sulphuric acid (E)-(RS)-mono-[4-[2-[3-[5-(2,4-diamino-pyrimidin-5-ylmethyl)-2,3-dimethoxy-phenyl]-acryloyl]-1,2-dihydro-phthalazin-1-yl]-benzyl ester] Na salt (1:1), MS (ISP): 631.3 (M+H)$^+$ 10.2. Sulphuric acid (E)-(RS)-mono-[4-[2-[3-[5-(2,4-diamino-pyrimidin-5-ylmethyl)-2,3-dimethoxy-phenyl]-acryloyl]-1,2-dihydro-phthalazin-1-yl]-butyl ester] Na salt (1:1), MS (ISP): 597.3 (M+H)$^+$, is prepared in a analogous manner to Example 10.1.

Example 11

Preparation of (E)-(RS)-3-{5-(2,4-diamino-pyrimidin-5-ylmethyl)-2,3-dimethoxy-phenyl}-1-{1-(4-thiocyanato-butyl)-1H-phthalazin-2-yl}-propenone

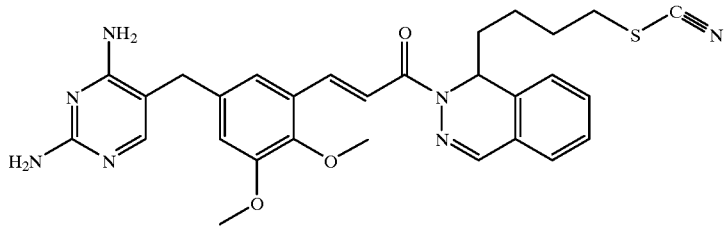

A solution of 206 mg of (E)-(RS)-3-{5-(2,4-diamino-pyrimidin-5-ylmethyl)-2,3-dimethoxy-phenyl)-1-{(4-hydroxy-but-1-yl)-1H-phthalazin-2-yl)-propenone in 2 ml of pyridine is treated with 37 µl of mesyl chloride at −20° C. After one hour the solution is concentrated and the residue, dissolved in 10 ml of dimethylformamide, is treated with 233 mg of potassium rhodanide at 80° C. for 24 hrs. The reaction solution is concentrated and the residue is chromatographed on silica gel (eluent: CH$_2$Cl$_2$/MeOH/NH$_4$OH: 95/5/0.5). The pure fractions are combined, concentrated and crystallized from methanol. 124 mg of (E)-(RS)-3-{5-(2,4-diamino-pyrimidin-5-ylmethyl)-2,3-dimethoxy-phennyl}-1–1-(4-thiocyanato-butyl)-1H-phthalazin-2-yl}-propenone are obtained as white cystals. MS (ISP): 558.3 (M+H)$^+$ Example 12

Preparation of (E)-(RS)-3-{5-(2,4-diamino-pyrimidin-5-ylmethyl)-2,3-dimethoxy-phenyl)-acryloyl-1,2-dihydrophthalazin-1-yl-propionaldehyde

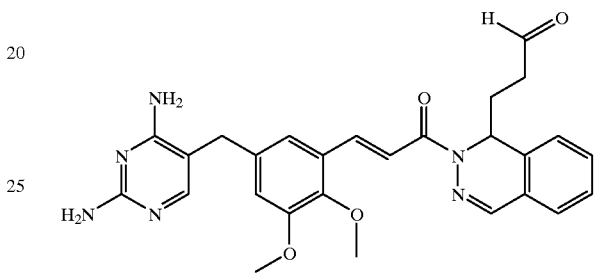

A solution of 764 mg of (E)-(RS)-3-[5-(2,4-diamino-pyrimidin-5-ylmethyl)-2,3-imethoxy-phenyl]-1-[1-(2-[1,3]dioxolan-2-yl-ethyl)-1H-phthalazin-2-yl)-propenone in 20 ml of acetone and 3 ml of water is treated with 3 ml of 2N hydrochloric acid over two days. The pH is adjusted to pH 7–8 using sodium bicarbonate solution and the aqueous phase is extracted three times with dichloromethane/methanol (9:1). The organic phase is back-washed with sodium chloride solution, dried over magnesium sulphate, filtered and the filtrate is concentrated. The residue is chromatographed on silica gel (eluent: CH$_2$Cl$_2$/MeOH/NH$_4$OH: 9/1/1). The pure fractions are combined, concentrated and crystallized from dichloromethane/hexane. The crystals are taken up in 150 ml of dichloromethane, stirred and suction filtered. The mother liquor is concentrated to about 25 ml and diluted with hexane. The crystals obtained are filtered off under suction. 388 mg of not quite pure (E)-(RS)-3-(5-(2,4-diamino-pyrimidin-5-ylmethyl)-2,3-dimethoxy-phenyl}-acryloyl-1,2-dihydrophthalazin-1-yl-propionaldehyde are obtained.

Example 13

13.1. Preparation of a mixture of (E) and (Z)-(RS)-5[2-[(E)-3-[5-(2,4-diamino-pyrimidin-5-ylmethyl)-2,3-dimethoxy-phenyl]-acryloyl]-1,2-dihydro-phthalazin-1-yl]-pent-2-enenitrile.

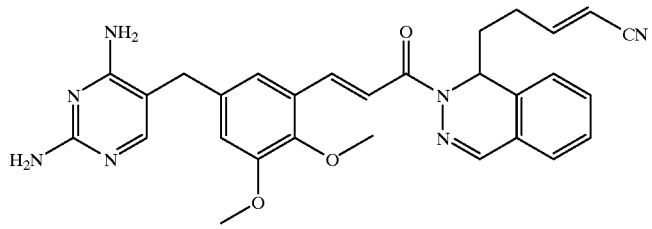

A suspension of 160 mg of (E)-(RS)-3-{5-(2,4-diamino-pyrimidin-5-ylmethyl)-2,3-dimethoxy-phenyl}-acryloyl-1,2-dihydrophthalazin-1-yl-propionaldehyde in 30 ml of tetrahydrofuran and 10 ml of dichloromethane is treated with 438 mg of cyanomethylene-triphenylphosphorane. After 12 hrs. the solution is concentrated and the residue is chromatographed on silica gel (eluent: $CH_2Cl_2$/MeOH/$NH_4OH$: 95/5/0.5). The pure fractions are combined, concentrated and cystallized from $CH_2Cl_2$/MeOH. There are obtained 150 mg of white crystals. MS (ISP): 524.4 (M+H)$^+$ The following compounds were prepared analogously to Example 13.1:

13.2. Allyl (E)-(RS)-5[2-[(E)-3-[5-(2,4-diamino-pyrimidin-5-ylmethyl)-2,3-dimethoxy-phenyl]-acryloyl]-1,2-dihydrophthalazin-1-yl]-pent-2-enoate. MS-(ISP): 583.4 (M+H)$^+$ 13.3. (EE)-(RS)-3-[3-(2-{3-[5-(2,4-Diamino-pyrimidin-5-ylmethyl)-2,3-dimethoxy-phenyl]-acryloyl}-1,2-dihydrophthalazin-1-yl]-propylidene]-1-hydroxy-pyrrolidin-2-one

Example 14

Preparation of 3-[3-(2-{3-[5-(2,4-diamino-pyrimidin-5-ylmethyl)-2,3-dimethoxy-phenyl]-acryloyl}-1,2-dihydrophthalazin-1-yl]-propylidene]-1-(2-trimethylsilanyl-ethoxy)-pyrrolidin-2-one.

A mixture of 230 mg of (E)-(RS)-3-{5-(2,4-diamino-pyrimidin-5-ylmethyl)-2,3-dimethoxy-phenyl}-acryloyl-1,2-dihydrophthalazin-1-yl-propionaldehyde, 498 mg of (RS)-[2-oxo-1-(2-trimethylsilanyl-ethoxy)-pyrrolidin-3-yl]-triphenylphosphonium, 5 ml of butylene oxide and 5 ml of dichloromethane is heated to 50° C. After 8 hrs. the reaction solution is concentrated and the residue is chromatographed on silica gel (eluent: $CH_2Cl_2$/MeOH/$NH_4OH$: 95/5/0.5). The pure fractions are combined, concentrated and cystallized from $CH_2Cl_2$/hexane. There are obtained 222 mg of white crystals, MS (ISP): 684.5 (M+H)$^+$.

The educt used in this reaction can be prepared as described in EP-A 0 620 225.

Example 15

Preparation of 3-[3-(2-{3-[5-(2,4-diamino-pyrimidin-5-ylmethyl)-2,3-dimethoxyphenyl]-acryloyl}-1,2-dihydrophthalazin-1-yl]-propylidene]-1-hydroxy-pyrrolidin-2-one.

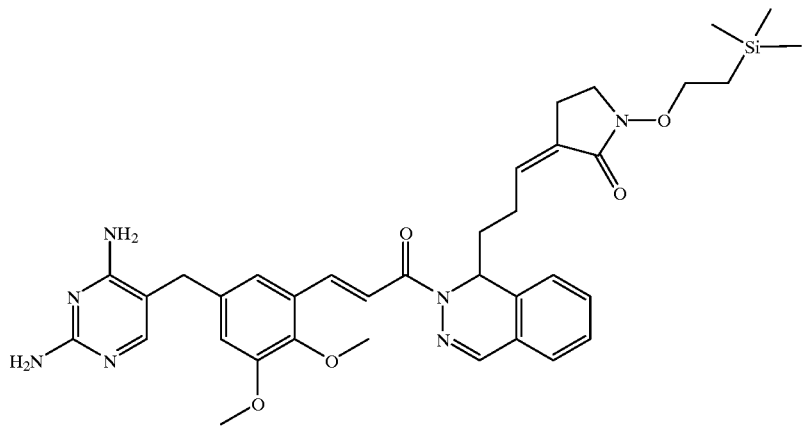

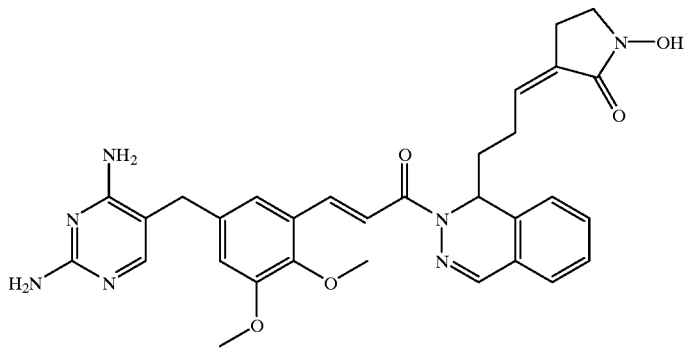

A solution of 220 mg of [3-(2-{3-[5-(2,4-diamino-pyrimidin-5-ylmethyl)-2,3-dimethoxy-phenyl]-acryloyl}-1,2-dihydrophthalazin-1-yl]-propylidene]-1-(2-trimethylsilanyl-ethoxy)-pyrrolidin-2-one in 2 ml of trifluoroacetic acid is stirred for 20 hrs. and then concentrated. The residue is dissolved in 5 ml of methanol and treated with 57 mg of sodium bicarbonate in 2 ml of water. The reaction solution is concentrated, the residue is dissolved in 5 ml of water and cooled to 0° C. The crystals obtained are filtered off under suction. There are obtained 117 mg of white crystals. MS (ISP): 584.4 (M+H)$^+$

Example 16
Preparation of (E)-(RS)-3-{5-(2,4-diamino-pyrimidin-5-ylmethyl)-2,3-dimethoxy-phenyl}-1-{1(3,4-dihydroxy-butyl)-1H-phthalazin-2-yl}-propenone.

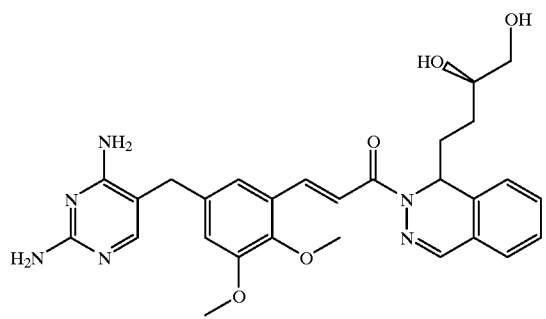

A mixture of 250 mg of (E)-(RS)-3-{5-(2,4-diamino-pyrimidin-5-ylmethyl)-2,3-dimethoxy-phenyl}-1-{1[2-(2,2-dimethyl-[1,3]-dioxolan-4-yl)-ethyl]-1H-phthalazin-2-yl}-propenone in 4 ml of methanol is treated with 0.65 ml of 2N HCl. The pH value is adjusted to 7–8 after one hour and the mixture is concentrated. The residue is taken up in methanol/dichloromethane, dried over magnesium sulphate and filtered. The filtrate is concentrated and the residue is crystallized from methanol. There are obtained 180 mg of substance. MS (ISP): 533.5 (M+H)$^+$ The educts of formula II which are used can be prepared as follows:

Example 17
17.1. Preparation of 3-iodo-5-methoxy-4-methoxymethoxy-benzaldehyde
14.8 g of potassium carbonate are added a solution of 20 g of 5-iodovanillin in 190 ml of N,N-dimethylformamide. The mixture is cooled to about 10° C. and then treated dropwise with 8.1 ml of chloromethyl added thereto within 40 min. The mixture is stirred at room temperature for 30 min., poured on to about 300 ml of ice-water and extracted 5 times with 150 ml of ethyl acetate each time. The organic phases are combined dried, concentrated and the residue is recrystallized from diethyl ether. 15.4 g of 3-iodo-5-methyl-4-methoxymethoxy-benzaldehyde are isolated as a colorless solid.

17.2 Preparation of (E/Z)-2-(3-iodo-5-methoxy-4-methoxymethoxy-benzyl)-3-phenylamino-acrylonitrile
5.0 g of 3-iodo-5-methyl-4-methoxymethoxy-benzaldehyde and 2.73 g of 3-anilinopropionitrile are dissolved in 90 ml of dimethyl sulphoxide and cooled to about 10° C. After the portionwise addition of 2.16 g of potassium tert.-butylate the mixture is stirred at room temperature for a further 2 hrs., then treated with 150 ml of water and 100 ml of diethyl ether. The organic phase is separated, dried and concentrated. After trituration of the residue in diethyl ether 5.65 g of (E/Z)-2-(3-iodo-5-methoxy-4-methoxymethoxy-benzyl)-3-phenyl-amino-acrylonitrile are obtained as a yellowish solid.

17.3. Preparation of 5-(3-iodo-5-methoxy-4-methoxymethoxy-benzyl)-pyrimidine-2,4-diamine
2.15 g of sodium methylate are dissolved in 190 ml of ethanol. 3.9 g of guanidine hydrochloride are added there to within 40 min. The mixture is stirred at room temperature for 1 hr. and subsequently treated portionwise with 5.0 g of (E/Z)-2-(3-iodo-5-methoxy-4-methoxymethoxy-benzyl)-3-phenyl-amino-acrylonitrile. The reaction mixture is held at reflux overnight. The mixture is suction filtered, the insoluble salts are washed with ethanol and the organic phase is dried and concentrated. After recrystallization of the residue from ethanol there are isolated 3.65 g of 5-(3-iodo-5-methoxy-4-methoxymethoxy-benzyl)-pyrimidine-2,4-diamine as a colorless solid, m.p. 180° C., dec.

The preparation of the compounds of formula III (educts of Examples 1–16) is effected as described hereinafter or in analogy thereto.

Example 18
18.1. Preparation of (RS)-1-(1-phenyl-1H-phthalazin-2-yl)-propenone
A solution of 1.11 g of 1-phenyl-1,2-dihydro-phthalazine and 0.67 g of triethylamine in 10 ml of methylene chloride is treated slowly while cooling with ice with a solution of 0.53 g of acryloyl chloride in 10 ml of methylene chloride. Subsequently, the mixture is stirred at room temperature for 20 min., poured on to ice-water and extracted with ethyl acetate. The organic phase is dried, concentrated and chromatographed on 50 g of silica gel; eluent: ethyl acetate/hexane 3:7 v/v. 1.30 g of (RS)-1-(1-phenyl-1H-phthalazin-2-yl)-propenone are obtained as a colorless oil. MS: 262 (M$^+$).

The following compounds of formula III were prepared in analogy to Example 18.1.:

18.2. (RS)-1-(1-(Pyridin-2-yl)-1H-phthalazin-2-yl)-propenone as a yellow resin. MS: 263 (M+).

18.3. (RS)-1-(1-Furan-2-yl-1H-phthalazin-2-yl)-propenone as a yellow oil. MS : 252 (M+).

18.4. (RS)-1-(1-Butyl-1H-phthalazin-2-yl)-propenone as a yellow oil. MS: 242 (M+).

18.5. (RS)-1-(1-Thiazol-2-yl-1H-phthalazin-2-yl)-propenone as a yellow solid.

18.6. (RS)-2-(2-Acryloyl-1,2-dihydro-phthalazin-1-yl)-N,N-dimethyl-benzenesulphonamide as a greenish, unstable oil. MS (ISP): 370 (M+H)+.

18.7. (RS)-1-[1-(2-Dimethylaminomethyl-phenyl)-1H-phthalazin-2-yl]-propenone as a yellowish unstable oil.

18.8. (RS)-1-[1-(5-Methyl-pyridin-2-yl)-1H-phthalazin-2-yl]-propenone as a brownish solid.

18.9. (RS)-1-[1-(4-Fluoro-phenyl)-1H-phthalazin-2-yl]-propenone as a yellow oil. MS (ISP): 281.1 (M+H)+.

18.10. (RS)-1-[1-(2,4-Difluoro-phenyl)-1H-phthalazin-2-yl]-propenone as a yellowish oil. MS: 298 (M+).

18.11. (RS)-1-(1-Tridecafluorohexyl-1H-phthalazin-2-yl)-propenone as a yellowish oil. MS (ISP): 505.2 (M+H)+.

18.12. (RS)-1-1-(1-Phenylsulphinylmethyl-1H-phthalazin-2-yl)-propenone as a yellowish oil. MS: 325 (M+H)+.

18.13. (E)-(RS)-1-{1-Methyl-1H-phthalazin-2-yl}-propenone. MS (EI): 200 (M)

18.14. (RS)-1-{1-Ethyl-1H-phthalazin-2-yl}-propenone. MS (EI): 214(M)

18.15. (E)-(RS)-1-{1-Propyl-1H-phthalazin-2-yl}-propenone. MS (EI): 228 (M)

18.16. (E)-(RS)-1-{1-(Isopropyl)-1H-phthalazin-2-yl}-propenone. MS (EI): 228 (M)

18.17. (E)-(RS)-1-{1-(3-Methyl-but-1-yl)-1H-phthalazin-2-yl)-propenone. MS (EI): 256 (M)

18.18. (E)-(RS)-1-{1[2,2-Dimethyl-[1,3]-dioxolan-4-yl]-ethyl)-1H-phthalazin-2-yl}-propenone. MS (ISP): 315.2 (M+H)+.

18.19. (E)-(RS)-1-[1-(2-[1,3]-Dioxolan-2-yl-ethyl)-1H-phthalazin-2-yl]-propenone. MS (ISP): 287.3 (M+H)+.

18.20. (RS)-1-(1-Cyclohexylmethyl-1H-phthalazin-2-yl)-propenone. MS (ISP): 283.4 (M+H)+.

18.21. (RS)-(1-Methylsulfanylmethyl-1H-phthalazin-2-yl)-propenone. MS: 247 (M+)

18.22. (RS)-[1-(4-tert-Butyl-phenyl)-1H-phthalazin-2-yl]-propenenone (yellow oil), 18.23. (RS)-(1-p-Tolyl-1H-phthalazin-2-yl)-propenone (yellow oil), 18.24. (RS)-[1-(4-Ethyl-phenyl)-1H-phthalazin-2-yl]-propenone (yellow oil), 18.25. (RS)-[1-(4-Trifluoromethoxy-phenyl)-1H-phthalazin-2-yl]-propenone (yellow oil), 18.26. (RS)-[1-(3,4-Dimethyl-phenyl)-1H-phthalazin-2-yl]-propenone (yellow oil), 18.27. (RS)-(1-tert-Butyl-1H-phthalazin-2-yl)-propenone MS: 242 (M+), 18.28. (RS)-[1-(5,6-Dihydro-4H-pyran-2-yl)-1H-phthalazin-2-yl]-propenone MS (ISP): 269.3 (M+H)+, 18.29. (RS)-[1-(2,4,6-Trimethyl-phenyl)-1H-phthalazin-2-yl]-propenone MS (ISP): 305.3 (M+H)+, 18.30 (RS)-1-(1-Biphenyl-4-yl-1H-phthalazin-2-yl)-propenone, m.p. 120° C. (diisopropylether). MS (ISP): 339.3 (M+H)+, 18.31 (RS)-1-[1-[4-[1-Ethoxy-ethoxy]-phenyl]-1H-phthalazin-2-yl]-propenone, (yellow oil) MS (ISP): 351.3 (M+H)+, 18.32 (RS)-1-(1-Bicyclo[2.2.1]hept-2endo- and/or 2exo-2-yl-1H-phthalazin-2-yl)-propenone, (yellow oil) MS (ISP): 281.2 (M+H)+.

18.33 (RS)-1-[1-(6-Methyl-pyridin-2-yl)-1H-phthalazin-2-yl]-propenone, m.p. 102° C. (diisopropylether). MS (ISP): 278.2 (M+H)+, 18.34 (RS)-1-[1-(4-Dimethylamino-phenyl)-1H-phthalazin-2-yl]-propenone, m.p. 118–122° C. (ethyl acetate/hexane). MS (ISP): 306.3 (M+H)+.

18.35 (RS)-1-{1-(4-(2-Ethoxy-ethoxy)-phenyl]-1H-phthalazin-2-yl)-propenone, b.p. 205° C./0.06 mbar MS (ISP): 351.3 (M+H)+.

18.36 (RS)-1-(1-m-Tolyl-1H-phthalazin-2-yl)-propenone, b.p. 170° C./0.1 mbar MS (EI): 276 (M).

18.37 (RS)-1-[1-(3,5-Dimethyl-phenyl)-1H-phthalazin-2-yl]-propenone m.p. 110° C. (hexane). MS (ISP): 291.2 (M+H)+.

18.38 (RS)-1-[1-(4-Pyrrol-1-yl-phenyl)-1H-phthalazin-2-yl]-propenone, (red oil), MS (ISP): 328.2 (M+H)+.

18.39 (RS)-1-[1-(2,3-Dihydro-benzo[1,4]dioxin-6-yl)-1H-phthalazin-2-yl]-propenone, (yellow oil), 18.40 (RS)-1-(1-Cyclopropyl-1H-phthalazin-2-yl)-propenone, b.p. 120–125° C./0.08 mbar MS (EI): 226 (M), 18.41 (RS)-1-[1-(4-Methylsulfanyl-phenyl)-1H-phthalazin-2-yl]-propenone, m.p. 95–98° C. (ethyl acetate/hexane). MS (EI): 308 (M), 18.42 (RS)-1-[1-(6-Methyl-pyridin-3-yl)-1H-phthalazin-2-yl]-propenone, m.p. 76–79° C. (ethyl acetate/hexane). MS (ISP): 278.2 (M+H)+, 18.43 (RS)-1-(1-[1,3]Dithian-2-yl-1H-phthalazin-2-yl)-propenone, m.p. 140–143° C. (ethyl acetate/hexane). MS (ISP): 305.2 (M+H)+.

18.44 (RS)-1-[1-(6-Dimethylamino-pyridin-3-yl)-1H-phthalazin-2-yl]-propenone, m.p. 125–127° C. (ethyl acetate/hexane), MS (ISP): 307.2 (M+H)+.

18.45 (RS)-1-(1-Pyridin-3-yl-1H-phthalazin-2-yl)-propenone, MS (ISP): 264.3 (M+H)+.

18.46 (RS)-1-(1-Cyclobutyl-1H-phthalazin-2-yl)-propenone, b.p. 120° C./0.05 mbar MS (ISP): 241.4 (M+H)+.

18.47 (RS)-1-(1-Cyclopentyl-1H-phthalazin-2-yl)-propenone, b.p. 150° C./0.12 mbar MS (EI): 254 (M).

18.48 (RS)-1-[1-(4-Trifluoromethyl-phenyl)-1H-phthalazin-2-yl]-propenone, m.p. 90–91° C. (hexane). MS (ISP): 331.2 (M+H)+.

18.49 (RS)-1-[1-(5-Chloro-pyridin-2-yl)-1H-phthalazin-2-yl]-propenone, m.p. 131–132° C. (ethyl acetate/hexane) MS (ISP): 298.2 (M+H)+.

8.50 (RS)-1-(1-Cyclohexyl-1H-phthalazin-2-yl)-propenone, b.p. 135° C./0.08 mbar MS (EI): 268 (M).

18.51 (RS)-1-[1-(4-Methoxy-phenyl)-1H-phthalazin-2-yl]-propenone, b.p. 165° C./0.1 mbar MS (ISP): 293.3 (M+H)+.

18.52 (RS)-1-[1-(3,4-Dimethoxy-phenyl)-1H-phthalazin-2-yl]-propenone, b.p. 124–125° C. (ethyl acetate/hexane) MS (ISP): 323.3 (M+H)+.

18.53 (RS)-1-(1-Benzo[1,3]dioxol-5-yl-1H-phthalazin-2-yl)-propenone, m.p. 98–101° C. (ethyl acetate/hexane) MS (EI): 306 (M).

18.54 (RS)-4-(2-Acryloyl-1,2-dihydro-phthalazin-1-yl)-benzonitrile.

18.55 (RS)-4-(2-Acryloyl-1,2-dihydro-phthalazin-1-yl)-benzoic acid tert-butyl ester, 18.56 (RS)-1-(1-Thiophen-2-yl-1H-phthalazin-2-yl)-propenone, (orange oil) MS (EI): 268 (M).

18.57 (RS)-1-[1-(5-Butyl-thiophen-2-yl)-1H-phthalazin-2-yl]-propenone, (yellow oil) MS (EI): 324 (M).

18.58 (RS)-1-{1-[4-(1-Hydroxy-ethyl)-phenyl]-1H-phthalazin-2-yl}-propenone, 18.59 (RS)-1-(1-Benzenesulfonylmethyl-1H-phthalazin-2-yl)-propenone, m.p. 113–116° C. (ethyl acetate/hexane) MS (ISP): 341.1 (M+H)$^+$.

18.60 (RS)-4-(2-Acryloyl-1,2-dihydro-phthalazin-1-yl)-N,N-dimethyl-benzenesulfonamide, MS (ISP): 370.2 (M+H)$^+$.

18.61 (RS)-1-[1-(4-Methoxymethyl-phenyl)-1H-phthalazin-2-yl]-propenone, b.p. 200° C./0.11 mbar MS (ISP): 307.2 (M+H)$^+$.

18.62 (RS)-1-(1-{4-[(Diisopropylamino)-methyl]-phenyl}-1H-phthalazin-2-yl)-propenone, m.p. 99–101° C. (hexane). MS (ISP): 376.4 (M+H)$^+$.

18.63 (RS)-1-[1-(4-Chloro-phenyl)-1H-phthalazin-2-yl]-propenone, m.p. 71–72° C. (ethyl acetate/hexane). MS (ISP): 297.2 (M+H)$^+$.

18.64 (RS)-1-[1-(6-Methoxy-pyridin-3-yl)-1H-phthalazin-2-yl]-propenone, m.p. 128–130° C. (ethyl acetate/hexane). MS (ISP): 294.3 (M+H)$^+$.

18.65 (RS)-1-{1-[4-(4-Methyl-piperazin-1-ylmethyl)-phenyl]-1H-phthalazin-2-yl}-propenone, (yellow oil) MS (ISP): 375.4 (M+H)$^+$.

18.66 (RS)-1-[1-(4-Morpholin-4-ylmethyl-phenyl)-1H-phthalazin-2-yl]-propenone, (yellow oil). MS (ISP): 362.2 (M+H)$^+$.

18.67 (RS)-1-(1-Adamantan-1-yl-1H-phthalazin-2-yl)-propenone, m.p. 157–158° C. (hexane). MS (ISP): 321.3 (M+H)$^+$.

18.68 RS)-1-1-[6-(1-Hydroxy-1-methyl-ethyl)-pyridin-3-yl]-1H-phthalazin-2-yl)-propenone, 18.69 (RS)-1-[1-(6-Morpholin-4-yl-pyridin-3-yl)-1H-phthalazin-2-yl]-propenone, (yellow oil) MS (ISP): 349.4 (M+H)$^+$.

18.70 (RS)-5-(2-Acryloyl-1,2-dihydro-phthalazin-1-yl)-pyridin-2-carbonic acid tert-butylamide, MS (EI): 362 (M).

The (+)-enantiomere compounds and (–)-enantiomere compounds respectively, can be prepared from the racemic [1H-Phthalazin-2-yl]-propenone by HPLC (e.g. ChiralCell OD). Thus are obtained:

18.71. S-(+)-(1-Phenyl-1H-phthalazin-2-yl)-propenone; $[\alpha]_D$=+724° (c=1; methanol).

18.72. R-(–)-(1-Phenyl-1H-phthalazin-2-yl)-propenone; $[\alpha]_D$=–720° (c=1; methanol).

18.73. R-(+)-(1-Furan-2-yl-1H-phthalazin-2-yl)-propenone; $[\alpha]_D$=+6380 (c=1; methanol).

18.74. S-(–)-(1-Furan-2-yl-1H-phthalazin-2-yl)-propenone; $[\alpha]_D$=–622° (c=1 methanol).

18.75. S-(+)-(1-Propyl-1H-phthalazin-2-yl)-propenone; $[\alpha]_D$=+8610 (c=1 methanol).

18.76. R-(–)-(1-Propyl-1H-phthalazin-2-yl)-propenone; $[\alpha]_D$=–902° (c=1 methanol).

18.77. S-(+)-(1-Methyl-1H-phthalazin-2-yl)-propenone; $[\alpha]_D$=+874° (c=1 methanol).

18.78. R-(–)-(1-Methyl-1H-phthalazin-2-yl)-propenone; $[\alpha]_D$=–903° (c=1; methanol).

8.79 (E)-(R)-1-[1-(6-Methyl-pyridin-3-yl)-1H-phthalazin-2-yl]-propenone, b.p. 45° C./0.08 mbar, $[\alpha]_D$=+571° (c=1, methanol). MS (ISP): 278.1 (M+H)$^+$.

8.80 (E)-(S)-1-[1-(6-Methyl-pyridin-3-yl)-1H-phthalazin-2-yl]-propenone, b.p. 150° C./0.1 mbar, $[\alpha]_D$=–536° (c=0.8, methanol). MS (ISP): 278.2 (M+H)$^+$.

18.81 (R)-1-(1-Cyclopropyl-1H-phthalazin-2-yl)-propenone, b.p. 120° C./0.1 mbar, $[\alpha]_D$=+9600 (c=1, methanol). MS (EI): 226 (M).

18.82 (S)-1-(1-Cyclopropyl-1H-phthalazin-2-yl)-propenone, b.p. 120° C./0.1 mbar, $[\alpha]_D$=–958° (c=1, methanol). MS (EI): 226 (M).

18.83 (R)-1-[1-(4-Methylsulfanyl-phenyl)-1H-phthalazin-2-yl]-propenone, m.p. 98–104° C., $[\alpha]_D$=+623° (c=1, chloroform). MS (ISP): 309.1 (M+H)$^+$.

18.84 (S)-1-[1-(4-Methylsulfanyl-phenyl)-1H-phthalazin-2-yl]-propenone, m.p. 98–104° C., $[\alpha]_D$=–635° (c=1, chloroform). MS (EI): 308 (M).

The compounds of formula III in which $R^3$ is cyclopentanone are prepared as follows:

Example 19

Preparation[of (RS)-2-(2-acryloyl-1,2-dihydro-phthalazin-1-yl)-cyclopentanone

A solution of 317 mg of acryloyl chloride in 1.5 ml of methylene chloride is slowly added dropwise at 0° C. to a solution of 390 mg of phthalazine and 536 mg of 1-morpholinocyclopentene in 10 ml of methylene chloride. The mixture is stirred at 0° C. for 2 hrs., then concentrated, treated with ice-water and made basic by the addition of sodium carbonate. The mixture is extracted 3 times with ethyl acetate. The organic phases are combined, dried, filtered, the filtrate is concentrated and the residue is chromatographed on 65 g of silica gel; eluent: cyclohexane/ethyl acetate 4:1. 136 mg of (RS)-2-(2-acryloyl-1,2-dihydro-phthalazin-1-yl)-cyclopentanone (mixture of diastereomers) are isolated as a yellowish oil. MS: 268 (M$^+$).

The compounds of formula III in which $R^3$ is cyclohexanone are prepared as follows:

Example 20

Preparation of (RS)-2-(2-acryloyl-1,2-dihydro-phthalazin-1-yl)-cyclohexanone

A solution of 0.53 ml of acryloyl chloride in 3 ml of methylene chloride is slowly added dropwise at 0° C. to a solution of 0.78 g of phthalazine and 1.2 ml of 1-trimethylsiloxy-cyclohexene. After the addition the mixture is stirred at 0° C. for a further 30 min., then concentrated, treated with ice-water and made basic by the addition of sodium carbonate. The mixture is extracted 3 times with 100 ml of ethyl acetate each time. The organic phases are combined, dried over magnesium sulphate, filtered and the filtrate is concentrated. 1.63 g of (RS)-2-(2-acryloyl-1,2-dihydro-phthalazin-1-yl)-cyclohexanone (mixture of diastereomers) are isolated as a brownish oil. MS: 282 (M$^+$).

The following compounds of formula III are prepared in analogy to Example 20.1.

20.2. (RS)-1-[1-(2-Oxo-propyl)-1H-phthalazin-2-yl]-propenone as a brownish oil. MS: 242 (M$^+$).

20.3. Methyl (RS)-2-(2-acryloyl-1,2-dihydro-phthalazin-1-yl)-2-methyl-propionate as a brownish oil. MS: 286 (M$^+$).

20.4. (RS)-1-[1-(1-Methyl-2-oxo-2-phenyl-ethyl)-1H-phthalazin-2-yl]-propenone (mixture of diastereomers) as a brownish oil. MS: 318 (M$^+$).

20.5. (RS)-1-[1-(2-Oxo-2-phenyl-ethyl)-1H-phthalazin-2-yl]-propenone as a yellow oil. MS: 304 (M$^+$).

20.6. (RS)-3-(2-Acryloyl-1,2-dihydro-phthalazin-1-yl)-tetrahydro-pyran-2-one (mixture of diastereomers) as a yellow foam. MS: 284 (M$^+$).

20.7. (RS)-1-[1-(2-Furan-2-yl-2-oxo-ethyl)-1H-phthalazin-2-yl]-propenone as a brownish oil. MS: 294 (M$^+$).

The compounds of formula III in which $R^3$ is hydrogen are prepared as follows:

Example 21
Preparation (sic) of 1-(1H-phathalazin-2-yl)-propenone

A solution of 1 g of phthalazine in 10 ml of methanol is treated at −78° C. with 290 mg of sodium borohydride and stirred for a further 10 min. A solution of 0.75 g of acryloyl chloride in 5 ml of diethyl ether is added dropwise at −78° C. during 45 min. and the pale yellow suspension is stirred at −78° C. for a further 1 hr. The mixture is poured on to 50 ml of ice-water, treated with 50 ml of a 10% aqueous sodium carbonate solution and extracted with 3×50 ml of methylene chloride. The organic phases are combined and washed with 100 ml of water and 50 ml of a saturated aqueous sodium chloride solution. The organic phase is dried over magnesium sulphate, filtered, the filtrate is concentrated and the residue is chromatographed on 80 g of silica gel; eluent: ethyl acetate. 1.22 g of 1-(1H-phthalazin-2-yl)-propenone are isolated as a pale yellow oil. MS: 186 (M$^+$).

Compounds of formula III in which R$^3$ carries a hydroxyalkyl group are prepared as follows:

Example 22

22.1. Preparation of (E)-(RS)-1-{1-(4-hydroxymethyl-phenyl)-1H-phthalazin-2-yl}-propenone. solution of 730 mg of E)-(RS)-1-{1-(4-tetrahydro-pyran-2-yloxymethyl)-phenyl]-1H-phthalazin-2-yl}-propenone in 20 ml of methanol is treated with a spatula tip of para-toluenesulphonic acid. After two hours the reaction mixture is concentrated and the residue is chromatographed on silica gel. 320 mg of CH$_2$Cl$_2$/MeOH/NH$_4$OH: 95/5/0.5) are obtained as a colorless oil. MS (EI): 292 (M).

The educt (E)-(RS)-1-(1-(4-tetrahydro-pyran-2-yloxymethyl)-phenyl]-1H-phthalazin-2-yl}-propenone, MS (ISP): 377.3 (M+H)$^+$, used in Reaction 22 is prepared by reacting the corresponding 4-tetrahydro-pyran-2-yloxymethyl)-phenyl bromide with phthalazine in the presence of butyllithium.

The following compounds of formula III in which R$^3$ carries a hydroxyalkyl group were prepared in analogy to Example 22.1.

22.2. (E)-(RS)-1-{1-(2-Hydroxymethyl-phenyl)-1H-phthalazin-2-yl)-propenone. MS (ISP): 293.2 (M+H)$^+$ The educt (E)-(RS)-1-{1-(2-tetrahydro-pyran-2-yloxymethyl)-phenyl]-1H-phthalazin-2-yl)-propenone, MS (ISP): 377.4 (M+H)$^+$, is [prepared] from the corresponding 2-tetrahydro-pyran-2-yloxymethyl-phenyl bromide by reaction with butyllithium.

22.3. (E)-(RS)-1-{1-(3-Hydroxymethyl-phenyl)-1H-phthalazin-2-yl}-propenone. MS (ISP): 293.2 (M+H)$^+$ The educt (E)-(RS)-1-{1-(3-tetrahydro-pyran-2-yloxymethyl)-phenyl]-1H-phthalazin-2-yl}-propenone, MS (ISP): 377.2 (M+H)$^+$, is prepared from the corresponding 1-(3-tetrahydro-pyran-2-yloxymethyl)-phenyl] bromide by reaction with butyllithium.

22.4. (E)-(RS)-1-1-(4-(2-Hydroxyethyl)-phenyl)-1H-phthalazin-2-yl}-propenone. MS(ISP): 307.3 (M+H)$^+$ The educt (E)-(RS)-1-(1-[4-(2-tetrahydro-pyran-2-yloxy)-ethyl]-phenyl}-1H-phthalazin-2-yl)-propenone MS (EI): 390 (M), is prepared from the corresponding 1-[4-(2-tetrahydro-pyran-2-yloxy) ethyl]-phenyl} bromide by reaction with butyllithium.

22.5. (E)-(RS)-1-{1-(4-Hydroxybutyl)-1H-phthalazin-2-yl}-propenone, colourless oil, MS (EI): 258 (M).

The educt (E)-(RS)-1-(1-[4-[2-tetrahydro-pyran-2-yloxy]-butyl]-1H-phthalazin-2-yl}-propenone, MS (ISP): 343.3 (M+H)$^+$, is prepared from the corresponding Grignard reagent (from 1-[4-(2-tetrahydro-pyran-2-yloxy)-ethyl]-phenyl bromide.

Compounds of formula III in which R$^3$ carries a hydroxy group are prepared as follows:

Example 23

23.1. Preparation of (E)-(RS)-1-{1-(4-hydroxy-phenyl)-1H-phthalazin-2-yl}-propenone.

A solution [of] 740 mg of 1-{1-[4-(tert-butyl-dimethylsilanyloxy)-phenyl]-1H-phthalazin-2-yl}-propenone in 20 ml of tetrahydrofuran is treated at about 0° C. with 1 ml of 1M tetrabutylammonium fluoride solution. After two hours the solvent is evaporated and the residue, dissolved in ethyl acetate, is washed with water and saturated sodium chloride solution. The organic phase is dried over magnesium sulphate, filtered, the filtrate is concentrated and the residue is chromatographed on silica gel (eluent: ethyl acetate/hexane: 1/1).

The pure fractions are combined, concentrated and triturated in hexane. 404 mg of (E)-(RS)-1-{1-(4-hydroxyphenyl)-1H-phthalazin-2-yl}-propenone are obtained as a white solid. MS (ISP): 279.2 (M+H)$^+$ The educt 1-{1-[4-(tert-butyl-dimethylsilanyloxy)-phenyl]-1H-phthalazin-2-yl}-propenone, MS (ISP): 393.4 (M+H)$^+$, is prepared from the corresponding 4-tert-butyl-dimethylsilanyloxy)-phenyl] bromide by reaction with butyllithium.

The following compound was prepared in analogy to Example 23.1.:

23.2. bb) (E)-(RS)-1-{1-(3-Hydroxy-phenyl)-1H-phthalazin-2-yl}-propenone. MS (ISP): 279.2 (M+H)$^+$ The educt 1-(1-[3-(tert-butyl-dimethylsilanyloxy)-phenyl]-1H-phthalazin-2-yl)-propenone, MS (EI): 392 (M), was prepared from the corresponding 3-(tert-butyl-dimethylsilanyloxy)-phenyl] bromide by reaction with butyllithium Compounds of formula III in which R$^3$ carries a carbamoyl group are prepared as follows:

Example 24

24.1 Preparation of (E)-(RS)-carbamic acid 4-(2-acryloyl-1,2-dihydro-phthalazin-1-yl)-benzyl ester.

A solution of 292 mg of E)-(RS)-1-{1-(4-hydroxymethyl-phenyl)-1H-phthalazin-2-yl}-propenone in 20 ml of dichloromethane is treated with 282 mg of disuccinyl carbonate and 61 mg of 4-dimethylaminopyridine. After 2 hrs. the solution is diluted with 20 ml of tetrahydrofuran and treated with 0.5 ml of triethylamine sic and 2 ml of saturated sodium chloride solution. After 12 hrs. the solvents are evaporated. The residue is dissolved in dichloromethane and washed with water. The organic phase is dried over magnesium sulphate, filtered, the filtrate is concentrated and the residue is chromatographed on silica gel (eluent: ethyl acetate/hexane: 2/1). The pure fractions are combined, concentrated. 210 mg of white product are obtained. MS (ISP): 336.2 (M+H)+353.3 (M+NH$_4$)$^+$ The following compounds were prepared in analogy to Example 23.1.:

24.2. (E)-(RS)-Morpholine-1-carbamic acid 4-[4-(2-acryloyl-1,2-dihydro-phthalazin-1-yl)-phenyl]-butyl ester. MS (ISP): 372.3 (M+H)$^+$ 24.3. (E)-(RS)-Carbamic acid 4-(2-acryloyl-1,2-dihydrophthalazin-1-yl)-butyl ester MS (ISP): 302.2 (M+H)$^+$ 24.4. (E)-(RS)-Carbamic acid 4-(2-acryloyl-1,2-dihydrophthalazin-1-yl)-propyl ester MS (ISP): 288.3 (M+H)$^+$ Compounds of formula III in which the $R^3$ carries an aldehyde group are prepared as follows:

Example 25
Preparation of (E)-(RS)-3-(2-acryloyl-1,2-dihydro-phthalazin-1-yl)-propionaldehyde A solution of 500 mg of (E)-(RS)-1-[1-(2-[1,3]-dioxolan-2-yl-ethyl)-1H-phthalazin-2-yl]-propenone in 15 ml of ethanol is treated with 3 ml of 2N HCl. After twenty hours at 60C the reaction mixture is concentrated and the residue is diluted in ethyl acetate, washed with saturated sodium bicarbonate and saturated sodium chloride solution then dried over magnesium sulphate filtered, the filtrate is concentrated and the residue is chromatographed on silica gel (eluent $CH_2Cl_2$/ether 95:). 50 mg of material [as a] colorless oil are obtained. MS (EI): 242 (M)

Compounds of formula III in which the $R^3$ carries an alkylhydroxy group can be prepared from the corresponding aldehyde as follows:

Example 26
Preparation [of] (E)-(RS)-1-[1-(3-hydroxy-propyl))-1H-phthalazin-2-yl]-propenone A solution of 220 mg in 3 ml of ethanol is treated at about 0° C. with 13 mg of sodium borohydride. After one hour the solution is concentrated, the residue is diluted with ethyl acetate, washed with saturated sodium bicarbonate and saturated sodium chloride solution then dried over magnesium sulphate, filtered, the filtrate is concentrated and the residue is chromatographed on silica gel (eluent hexane/ether 6:4). 176 mg of material are obtained. MS (EI): 244 (M)

The dihydro-phthalazines of formula IV used for the preparation of compounds III are generally relatively unstable, oxidation-sensitive compounds, which are often reacted directly in the crude state with acryloyl halides. They can be prepared as described hereinafter or in analogy thereto:

Example 27
27.1 Preparation of 1-phenyl-1,2-dihydro-phthalazine

A solution of 4 g of phthalazine in 50 ml of tetrahydrofuran is added dropwise at room temperature to a solution of phenyl-magnesium bromide (prepared from 6 g of bromobenzene and 1 g of magnesium in 30 ml of tetrahydrofuran). The reaction mixture is held at reflux for 6 hrs. After cooling the mixture is treated with a saturated aqueous solution of ammonium chloride and extracted 3 times with diethyl ether. The organic phases are combined, dried and subsequently triturated with pentane. 2.32 g of not quite pure 1-phenyl-1,2-dihydro-phthalazine are isolated as a yellowish solid, m.p. 79° C.

The following compounds of formula IV are prepared in analogy to Example 27.1.
27.2. 1-Pyridin-2-yl-1,2-dihydro-phthalazine as a brownish oil MS: 208 (M+).
27.3. 1-Thiazol-2-yl-1,2-dihydro-phthalazine as a brownish oil.
27.4. 1-Butyl-1,2-dihydro-phthalazine as a brownish oil.
27.5 1-(5-Methyl-pyridin-2-ylI-1,2-dihydro-phthalazine as a dark impure oil.
27.6. (RS)1-(2,4-Difluoro-phenyl)-1,2-dihydro-phthalazine as a reddish oil. MS: 245 (M+H)+.
27.7. (RS)-1-Cyclobutyl-1,2-dihydro-phthalazine m.p. 64–68° C. (hexane). MS ISP): 187.3 (M+H)+.
27.8. (RS)-1-Cyclopentyl-1,2-dihydro-phthalazine, brown solid
27.9. (RS)-1-Cyclohexyl-1,2-dihydro-phthalazine, m.p. 122–124° C. (hexane), MS (ISP): 215.4 (M+H)+.

Example 28
28.1. Preparation of 1-furan-2-yl-1,2-dihydrophthalazine 22.5 ml of an about 1.6M solution of butyllithium are slowly added dropwise at –78° C. to a solution of 2.46 g of furan in 30 ml of tetrahydrofuran. The mixture is stirred at –78° C. for 20 min., then at –20° C. for 2 hrs. The solution is again cooled to –78° C. and treated slowly with a solution of 4.68 g of phthalazine in 36 ml of tetrahydrofuran. The mixture is stirred at –78° C. for 2 hrs., then poured on to about 500 ml of ice-water and extracted 4 times with 150 ml of ethyl acetate each time. The organic phases are dried, concentrated and the residue is chromatographed immediately on 120 g of silica gel; eluent: hexane/ethyl acetate 3:7. 4.08 g of dark, impure 1-furan-2-yl-1,2-dihydrophthalazine are isolated.

The following compounds of formula IV are prepared in analogy to Example 28.1.:
28.2. 2-(1,2-Dihydro-phthalazin-1-yl)-N,N-dimethyl-benzenesulphonamide as an impure, dark oil, MS: 315 (M+).
28.3. [2-(1,2-Dihydro-phthalazin-1-yl)-benzyl]-dimethyl-amine as a dark, very unstable oil.
28.4. (RS)-1-Methylsulfanylmethyl-1H-phthalazine as an impure, yellow oil,
28.5. (RS)-1-(4-tert-Butyl-phenyl)-1H-phthalazine as an impure, yellow oil,
28.6. (RS)-1-p-Tolyl-1H-phthalazine as an impure, yellow oil,
28.7. (RS)-1-(4-Ethyl-phenyl)-1H-phthalazine as an impure, yellow oil,
28.8. (RS)-1-(4-Trifluoromethoxy-phenyl)-1H-phthalazine as an impure, yellow oil,
28.9. (RS)-1-(3,4-Dimethyl-phenyl)-1H-phthalazine as an impure, yellow oil,
28.10. (RS)-1-tert-Butyl-1H-phthalazine as an impure, yellow oil,
28.11. (RS)-1-(5,6-Dihydro-4H-pyran-2-yl)-1H-phthalazine MS (ISP): 213.3 (M+H)+.
28.12. (RS)-1-(2,4,6-Trimethyl-phenyl)-1H-phthalazine as an impure, yellow oil,
28.13 (RS)-1-Biphenyl-4-yl-1,2-dihydro-phthalazine, yellow oil,
28.14 (RS)-1-[1-[4-[1-Ethoxy-ethoxy]-phenyl]-1H-phthalazine, yellow oil,
28.15 (RS)-1-Bicyclo[2.2.1]hept-2endo- and/or 2exo 2-yl-1,2-dihydro-phthalazine, brown oil,
28.16 (RS)-1-(6-Methyl-pyridin-2-yl)-1,2-dihydro-phthalazine, yellow oil,
28.17 (RS)-[4-(1,2-Dihydro-phthalazin-1-yl)-phenyl]-dimethyl-amine, yellow oil,
28.18 (RS)-1-[4-(2-Ethoxy-ethoxy)-phenyl]-1,2-dihydro-phthalazine, m.p. 129–131° C. (acetylacetate/hexane). MS (EI): 296 (M).
28.19 (RS)-1-m-Tolyl-1,2-dihydro-phthalazine, brown oil
28.20 (RS)-1-(3,5-Dimethyl-phenyl)-1,2-dihydro-phthalazine, m.p. 102–107° C. (hexane). MS (ISP): 237.3 (M+H)+.
28.21 (RS)-1-(4-Pyrrol-1-yl-phenyl)-1,2-dihydro-phthalazine, m.p. 129–130° C. (toluol/hexane). MS (ISP): 274.3 (M+H)+.
28.22 (RS)-1-(2,3-Dihydro-benzo[1,4]dioxin-6-yl)-1,2-dihydro-phthalazine, yellow oil,
28.23 (RS)-1-Cyclopropyl-1,2-dihydro-phthalazine, yellow oil,
28.24 (RS)-1-(4-Methylsulfanyl-phenyl)-1,2-dihydro-phthalazine, m.p. 120–123° C. (acetylacetate/hexane), MS (ISP): 255.2 (M+H)+.

28.25 (RS)-1-(6-Methyl-pyridin-3-yl)-1,2-dihydro-phthalazine, yellow oil.

28.26 (RS)-1-[1,3]Dithian-2-yl-1,2-dihydro-phthalazine, m.p. 134–136° C. (diisopropylether). MS (ISP): 251.1 (M+H)$^+$.

28.27 (RS)-[5-(1,2-Dihydro-phthalazin-1-yl)-pyridin-2-yl]-dimethyl-amine, m.p. 124–127° C. (acetylacetate/hexane). MS (ISP): 253.2 (M+H)$^+$.

28.28 (RS)-1-Pyridin-3-yl-1,2-dihydro-phthalazine, 28.29 (RS)-1-(4-Trifluoromethyl-phenyl)-1,2-dihydro-phthalazine, 28.30 (RS)-1-(5-Chloro-pyridin-2-yl)-1,2-dihydro-phthalazine, 28.31 (RS)-1-(4-Methoxy-phenyl)-1,2-dihydro-phthalazine, m.p. 121–125° C. (acetylacetate/hexane). MS (EI): 238 (M).

28.32 (RS)-1-(3,4-Dimethoxy-phenyl)-1,2-dihydro-phthalazine, brown oil, 28.33 (RS)-1-Benzo[1,3]dioxol-5-yl-1,2-dihydro-phthalazine, m.p. 102–104° C. (acetylacetate/hexane). MS (ISP): 253.2 (M+H)$^+$.

28.34 (RS)-4-(1,2-Dihydro-phthalazin-1-yl)-benzonitrile, red oil, 28.35 (RS)-4-(1,2-Dihydro-phthalazin-1-yl)-benzoic acid tert-butyl ester, 28.36 (RS)-1-Thiophen-2-yl-1,2-dihydro-phthalazine, 28.37 1-[4-(1,2-Dihydro-phthalazin-1-yl)-phenyl]-ethanol, m.p. 133–134° C. (acetylacetate/hexane). MS (ISP): 253.2 (M+H)$^+$.

28.38 (RS)-1-Benzenesulfonylmethyl-1,2-dihydro-phthalazine, orange oil.

28.39 (RS)-4-(1,2-Dihydro-phthalazin-1-yl)-N,N-dimethyl-benzene-sulfonamide, 28.40 (RS)-1-(4-Methoxymethyl-phenyl)-1,2-dihydro-phthalazine, brown oil, 28.41 (RS)-[4-(1,2-Dihydro-phthalazin-1-yl)-benzyl]-diisopropyl-amine, brown oil, 28.42 (RS)-1-(4-Chloro-phenyl)-1,2-dihydro-phthalazine, m.p. 97–98° C. (hexane), MS (EI): 242 (M).

28.43 (RS)-1-(6-Methoxy-pyridin-3-yl)-1,2-dihydro-phthalazine, 28.44 (RS)-1-[4-(4-Methyl-piperazin-1-ylmethyl)-phenyl]-1,2-dihydro-phthalazine, yellow oil, 28.45 (RS)-1-(4-Morpholin-4-ylmethyl-phenyl)-1,2-dihydro-phthalazine, brown oil, 28.46 (RS)-1-Adamantan-1-yl-1,2-dihydro-phthalazine, m.p. 170–172° C., dec. (hexane). MS (ISP): 267.4 (M+H)$^+$.

28.47 (RS)-1-(6-Morpholin-4-yl-pyridin-3-yl)-1,2-dihydro-phthalazine, m.p. 167° C. (acetylacetate). MS (ISP): 295.3 (M+H)$^+$.

Example 29

Preparation of (RS)-1-(4-fluoro-phenyl)-1,2-dihydro-phthalazine 5.53 ml of a 1.6 M solution of butyllithium in hexane are added dropwise at −78° C. within 20 min. to a solution of 1.48 g of 1-bromo-4-fluoro-benzene in 5 ml of tetrahydrofuran. The resulting white suspension is stirred for a further hour. A solution of 1 g of phthalazine in 5 ml of tetrahydrofuran is added dropwise at −78° C. within 10 min. The reaction mixture is left to warm to room temperature, treated with 50 ml of water and extracted 3 times with 50 ml of dichloromethane each time. The organic phases are combined washed with 50 ml of water and 50 ml of a saturated sodium chloride solution, dried over magnesium sulphate, filtered, the filtrate is concentrated and the residue is chromatographed on 100 g of silica gel with the eluent hexane/ethyl acetate 1:1. 1.49 g (86%) of (RS)-1-(4-fluoro-phenyl)-1,2-dihydro-phthalazine are obtained as a yellow oil. MS: 227 (M+H)$^+$.

Example 30

Preparation of (RS)-1-benzenesulphinylmethyl-1,2-dihydro-phthalazine

A solution of 1 g of methyl phenyl sulphoxide in 14 ml of tetrahydrofuran is added dropwise at 78° C. within 10 min. to 3.93 ml of 2M solution of lithium diisopropylamide in tetrahydrofuran/heptane/ethylbenzene in 20 ml of tetrahydrofuran. The reaction mixture is stirred for a further 30 min. A solution of 0.928 g of phthalazine in 14 ml of tetrahydrofuran is added dropwise within 10 min. The mixture is stirred at −78° C. for 1 hr., treated with 100 ml of water and extracted 3 times with 50 ml of chloroform. The organic phases are combined, dried over magnesium sulphate, filtered and the filtrate is concentrated. 1.9 g of crude (RS)-1-benzenesulphinylmethyl-1,2-dihydro-phthalazine are isolated as a yellowish oil, MS(ISP): 271.2 (M+H)$^+$.

Example 31

Preparation of (RS)-1-(6-Methyl-pyridin-3-yl)-1,2-dihydro-phthalazine 15.3 ml of a 1.6 M solution of butyllithium in hexane are added dropwise at −78° C. within 20 min. to a solution of 5.68 g 2,5-dibromo-pyridine in 200 ml diethylether. Under stirring at −78° C. the following solutions are added dropwise: a solution of 2.6 g phthalazine in 100 ml tetrahydrofuran within 15 min., 16.9 ml of a 1.6 M solution of butyllithium in hexane within 5 min. and 2.24 ml methyliodide.

The reaction mixture is stirred for a further 30 min and treated with 100 ml water and 100 ml of a saturated sodium chloride solution. The organic phases are combined, dried over sodium sulphate and concentrated. 5.4 g (RS)-1-(6-methyl-pyridin-3-yl)-1,2-dihydro-phthalazine are obtained as yellow oil.

The following compounds are prepared in analogy to the preparation of (RS)-1-(6-Methyl-pyridin-3-yl)-1,2-dihydro-phthalazine, as described above.

31.1 (RS)-2-[5-(1,2-Dihydro-phthalazin-1-yl)-pyridin-2-yl]-propan-2-ol, brown solid.

31.2. (RS)-5-(1,2-Dihydro-phthalazin-1-yl)-pyridin-2-carbonic acid tert-butylamide, brown solid. .

Example 32

Preparation of (E)-(RS)-3-[5-(2,4-Diamino-pyrimidin-5-ylmethyl)-2,3-dimethoxy-phenyl]-1-[1-(6-methylsulfanyl-pyridin-3-yl)-1H-phthalazin-2-yl]-propenone 8.93 ml of a 1.6 M solution of butyllithium in hexane are added dropwise at −78° C. within 20 min. to a solution of 2.86 g 5-bromo-2-methyl-sulfanyl-pyridine in 50 ml diethylether. Under stirring at −78° C. are a solution of 1.56 g phthalazine in 50 ml tetrahydrofuran is added dropwise within 15 min. (solution A).

15.75 ml of a 1.6 M solution of butyllithium in hexane are added dropwise at −78° C. within 10 min. to a solution of 4.3 g (E)-3-[5-(2,4-diamino-pyrimidin-5-ylmethyl)-2,3-dimethoxy-phenyl]-acrylacid ethyl ester in 430 ml tetrahydrofuran. Solution A is added. The reaction mixture is stirred for a further 3 h. The termperature raises up to −10° C. 150 ml water and 100 ml of a saturated sodium chloride solution are added. The organic phases are combined, dried over sodium sulphate and concentrated and the residue is chromatographed on silica gel; eluent: methylenchlorid/methanol/25% ammoniak 95:5:0.5). The pure fractions are combined, concentrated and crystallized from ethanol. 2.9 g (E)-(RS)-3-[5-(2,4-diamino-pyrimidin-5-ylmethyl)-2,3-dimethoxy-phenyl]-1-[1-(6-methylsulfanyl-pyridin-3-yl)-1H-phthalazin-2-yl]-propenone are isolated, m.p. 142–145° C. MS (ISP): 568.3 (M+H)$^+$.

The following compounds are prepared in analogy to the preparation of (E)-(RS)-3-[5-(2,4-Diamino-pyrimidin-5-ylmethyl)-2,3-dimethoxy-phenyl]-1-[1-(6-methylsulfanyl-pyridin-3-yl)-1H-phthalazin-2-yl]-propenone.

32.1 (E)-(RS)-3-[5-(2,4-Diamino-pyrimidin-5-ylmethyl)-2,3-dimethoxy-phenyl]-1-[1-(4-methyl-pyridin-2-yl)-1H-phthalazin-2-yl]-propenone, m.p. 149–154° C. (methanol). MS (ISP): 536.4 (M+H)$^+$.

32.2 (E)-(RS)-3-[5-(2,4-Diamino-pyrimidin-5-ylmethyl)-2,3-dimethoxy-phenyl]-1-[1-(2-methyl-pyridin-3-yl)-1H-phthalazin-2-yl]-propenone, m.p. 150–155° C. (acetonitrile). MS (ISP): 536.3 (M+H)$^+$.

32.3 (E)-(RS)-3-[5-(2,4-Diamino-pyrimidin-5-ylmethyl)-2,3-dimethoxy-phenyl]-1-[1-(3-methoxy-phenyl)-1H-phthalazin-2-yl]-propenone, m.p. 114–118° C. (methanol). MS (ISP): 551.3 (M+H)$^+$.

32.4 (E)-(RS)-3-[5-(2,4-Diamino-pyrimidin-5-ylmethyl)-2,3-dimethoxy-phenyl]-1-[1-(2-methyl-pyridin-4-yl)-1H-phthalazin-2-yl]-propenone, m.p. 120° C. (ethanol). MS (ISP): 536.3 (M+H)$^+$.

32.5 (E)-(RS)-3-[5-(2,4-Diamino-pyrimidin-5-ylmethyl)-2,3-dimethoxy-phenyl]-1-[1-(2-methyl-pyrimidin-5-yl)-1H-phthalazin-2-yl]-propenone, m.p. 142–145° C. (methanol). MS (ISP): 537.4 (M+H)$^+$.

32.6 (E)-(RS)-3-[5-(2,4-Diamino-pyrimidin-5-ylmethyl)-2,3-dimethoxy-phenyl]-1-[1-(3,4,5-trimethoxy-phenyl)-1H-phthalazin-2-yl]-propenone, m.p. 190–196° C. (methanol). MS (ISP): 611.3 (M+H)$^+$.

32.7 (E)-(RS)-3-[5-(2,4-Diamino-pyrimidin-5-ylmethyl)-2,3-dimethoxy-phenyl]-1-[1-(6-hydroxymethyl-pyridin-3-yl)-1H-phthalazin-2-yl]-propenone, m.p. 133–136° C. (methanol). MS (EI): 551 (M).

32.8 (E)-(RS)-3-[5-(2,4-Diamino-pyrimidin-5-ylmethyl)-2,3-dimethoxy-phenyl]-1-(1-pyridin-4-yl-1H-phthalazin-2-yl)-propenone, m.p. 145-149° C. (acetonitrile). MS (ISP): 522.2 (M+H)$^+$.

32.9 (E)-(RS)-1-[1-(6-Bromo-pyridin-3-yl)-1H-phthalazin-2-yl]-3-[5-(2,4-diamino-pyrimidin-5-ylmethyl)-2,3-dimethoxy-phenyl]-propenone, m.p. 132–138° C. (methanol). MS (ISP): 602.1 (M+H)$^+$.

32.10 (E)-(RS)-3-[5-(2,4-Diamino-pyrimidin-5-ylmethyl)-2,3-dimethoxy-phenyl]-1-[1-(2,4-dimethoxy-pyrimidin-5-yl)-1H-phthalazin-2-yl]-propenone, 15 m.p. 160–165° C. (methanol). MS (ISP): 583.3 (M+H)$^+$.

32.11 (E)-(RS)-3-[5-(2,4-Diamino-pyrimidin-5-ylmethyl)-2,3-dimethoxy-phenyl]-1-[1-[4-(2-hydroxy-ethoxy)-phenyl]-1H-phthalazin-2-yl]-propenone, m.p. 169–172° C. (methanol). MS (ISP): 581.5 (M+H)$^+$.

32.12 (E)-(RS)-3-[5-(2,4-Diamino-pyrimidin-5-ylmethyl)-2,3-dimethoxy-phenyl]-1-[1-(4-methoxy-pyridin-2-yl)-1H-phthalazin-2-yl]-propenone, m.p. 125–133° C. (ethanol). MS (ISP): 552.2 (M+H)$^+$.

32.13 (E)-(RS)-3-[5-(2,4-Diamino-pyrimidin-5-ylmethyl)-2,3-dimethoxy-phenyl]-1-(1-[1,3]dioxolo[4,5-b]pyridin-6-yl-1H-phthalazin-2-yl)-propenone, m.p. 135–140° C. (ethanol). MS (ISP): 566.2 (M+H)$^+$.

32.14 (E)-(RS)-3-[5-(2,4-Diamino-pyrimidin-5-ylmethyl)-2,3-dimethoxy-phenyl]-1-[1-[6-(2-hydroxy-ethoxy)-pyridin-3-yl]-1H-phthalazin-2-yl]-propenone, m.p. 212–217° C. (methanol). MS (ISP): 582.1 (M+H)$^+$.

32.15 (E)-(RS)-3-[5-(2,4-Diamino-pyrimidin-5-ylmethyl)-2,3-dimethoxy-phenyl]-1-[1-[6-(2-methoxy-ethoxy)-pyridin-3-yl]-1H-phthalazin-2-yl]-propenone, m.p. 147–151° C. (methanol). MS (ISP): 596.2 (M+H)$^+$.

32.16 (E)-(RS)-3-[5-(2,4-Diamino-pyrimidin-5-ylmethyl)-2,3-dimethoxy-phenyl]-1-[1-[6-[2-(2-methoxy-ethoxy)-ethoxy]-pyridin-3-yl]-1H-phthalazin-2-yl]-propenone, m.p. 136–140° C. (ethanol). MS (ISP): 640.4 (M+H)$^+$.

32.17 (E)-(RS)-3-[5-(2,4-Diamino-pyrimidin-5-ylmethyl)-2,3-dimethoxy-phenyl]-1-[1-[6-(3-hydroxy-propoxy)-pyridin-3-yl]-1H-phthalazin-2-yl]-propenone, m.p. 173–178° C. (methanol). MS (ISP): 596.2 (M+H)$^+$.

32.18 1-[1-(6-Benzyloxy-pyridin-3-yl)-1H-phthalazin-2-yl]-3-[5-(2,4-diamino-pyrimidin-5-ylmethyl)-2,3-dimethoxy-phenyl]-propenone, m.p. 136–143° C. (ethanol). MS (ISP): 628.2 (M+H)$^+$.

32.19 3-[5-(2,4-Diamino-pyrimidin-5-ylmethyl)-2,3-dimethoxy-phenyl]-1-t-[6-(2-morpholin-4-yl-ethoxy)-pyridin-3-yl]-1H-phthalazin-2-yl}-propenone, m.p. 120–124° C. (ethanol). MS (ISP): 651.2 (M+H)$^+$.

32.20 3-[5-(2,4-Diamino-pyrimidin-5-ylmethyl)-2,3-dimethoxy-phenyl]-1-{1-[6-(2-dimethylamino-ethoxy)-pyridin-3-yl]-1H-phthalazin-2-yl}-propenone, m.p. 110–114° C. (ethanol/water). MS (ISP): 609.2 (M+H)$^+$.

32.21 (E)-(RS)-1-[1-(6-Chloro-pyridin-3-yl)-1H-phthalazin-2-yl]-3-[5-(2,4-diamino-pyrimidin-5-ylmethyl)-2,3-dimethoxy-phenyl]-propenone, m.p. 129–140° C. (methanol). MS (ISP): 556.1 (M+H)$^+$.

The starting material used above are prepared as follows:

Example 33

Preparation of 5-Bromo-2-(2-methoxy-ethoxy)-pyridine 1.1 g sodium and 2.5 g 2,5-dibromo-pyridine are added to 50 ml 2-methoxy-ethanol. The reaction mixture is heated to 90° C. and stirred for a further 2.5 hrs, then poured onto 75 ml of a saturated sodiumhydrogen carbonate solution and extracted three times with methylenchloride. The organic phases are combined, dried over sodium sulphate and concentrated and the residue is destilled. 2.2 g 5-Bromo-2-(2-methoxy-ethoxy)-pyridine are obtained., bp. 135° C./0.1 mbar MS (EI): 231 (M).

The following compounds are prepared in analogy to the preparation of 5-bromo-2-(2-methoxy-ethoxy)-pyridine.

33.1 2-(5-Bromo-pyridin-2-yloxy)-ethanol, m.p. 60° C. (hexane). MS (EI): 217 (M).

33.2 5-Bromo-2-[2-(2-methoxy-ethoxy)-ethoxy]-pyridine, b.p. 130° C./1 mbar MS (EI): 276 (M+H)$^+$.

33.3 3-(5-Bromo-pyridin-2-yloxy)-propan-1-ol, m.p. 58° C. (hexane). MS (EI): 231 (M).

33.4 4-[2-(5-Bromo-pyridin-2-yloxy)-ethyl]-morpholine, b.p. 130° C./0.2 mbar 33.5 [2-(5-Bromo-pyridin-2-yloxy)-ethyl]-dimethyl-amine, b.p. 100° C./0.16 mbar MS (ISP): 247.1 (M+H)$^+$.

Example 34

Preparation of (E)-(RS)-5-(2-{3-[5-(2,4-Diamino-pyrimidin-5-ylmethyl)-2,3-dimethoxy-phenyl]-acryloyl}-1,2-dihydro-phthalazin-1-yl)-pyridin-2-carbonic acid amide 15.3 ml of a 1.6 M solution of butyllithium in hexane are added dropwise at −78° C. within 15 min. to a solution of 5.68 g 2,5-dibromo-pyridine in 200 ml of diethylether. The reaction mixture is stirred at −78° C. for 10 min. Then a solution of 2.6 g phthalazine in 100 ml tetrahydrofuran is added. The reaction mixture is stirred at −78° C. for a further 10 min. Then 20.5 ml of a 1.6 M solution of butyllithium in hexane are added dropwise at −78° C. within 10 min. 5 ml trimethylsilylisocyanat are added. The reaction mixture is stirred for a further 20 min. The termperature raises up to −25° C. (solution A).

26.2 ml of a 1.6 M solution of butyllithium in hexane are added dropwise at −78° C. within 10 min to a solution of 7.16 g (E)-3-[5-(2,4-diamino-pyrimidin-5-ylmethyl)-2,3-dimethoxy-phenyl]-acrylacid ethyl ester in 750 ml tetrahydrofuran. Solution A is added. The reaction mixture is stirred for a further 5.5 h. The termperature raises up to −18° C. 200 ml water and 300 ml of a saturated sodium chloride solution are added. The organic phases are combined, dried over sodium sulphate and concentrated and the residue is chromatographed on silica gel; eluent: methylenchlorid/methanol/25% ammoniak 95:5:0.5). The pure fractions are combined, concentrated and crystallized from ethanol. After recrystallization from ethanol 0.84 g (E)-(RS)-5-(2-{3-[5-(2,4-Diamino-pyrimidin-5-ylmethyl)-2,3-dimethoxy-phenyl]-acryloyl)-1,2-dihydro-phthalazin-1-yl)-pyridin-2-carbonic acid amide are obtained; m.p. 204–209° C. (Ethanol). MS (ISP): 565.3 (M+H)+.

The following compounds are prepared in analogy to the preparation of (E)-(RS)-5-(2-13-[5-(2,4-Diamino-pyrimidin-5-ylmethyl)-2,3-dimethoxy-phenyl]-acryloyl)-1,2-dihydro-phthalazin-1-yl)-pyridin-2-carbonic acid amide.

34.1 (E)-(RS)-3-[5-(2,4-Diamino-pyrimidin-5-ylmethyl)-2,3-dimethoxy-phenyl]-1-[1-(6-ethyl-pyridin-3-yl)-1H-phthalazin-2-yl]-propenone, m.p. 124–130° C. (ethanol). MS (ISP): 550.2 (M+H)+.

Pharmaceutical preparations can be produced in a manner known per se according to the following formulations:

Example A

| Tablets: | |
|---|---|
| Sulfamethoxazole | 400 mg |
| Compound of formula I, e.g. (E)-(RS)-3-[5-(2,4-diamino-pyrimidin-5-ylmethyl)-2,3-dimethoxy-phenyl]-1-(1-phenyl-1H-phthalazin-2-yl)-propenone | 80 mg |
| PRIMOJEL (starch derivative) | 6 mg |
| POVIDONE K30 (polyvinylpyrrolidone) | 8 mg |
| Magnesium stearate | 6 mg |
| Total weight | 500 mg |

Example B

| Tablets: | |
|---|---|
| Compound of formula I, e.g. (E)-(RS)-3-[5-(2,4-diamino-pyrimidin-5-ylmethyl)-2,3-dimethoxy-phenyl]-1-(1-furan-2-yl-1H-phthalazin-2-yl)-propenone | 100 mg |
| Corn starch | 15 mg |
| Talc | 3 mg |
| Magnesium stearate | 2 mg |
| | 120 mg |

Example C

| Injection solutions: | |
|---|---|
| Compound of formula I, e.g. E)-(RS)-3-{5-(2,4-diamino-pyrimidin-5-ylmethyl)-2,3-dimethoxy-phenyl}-1-(1-propyl-1H-phthalazin-2-yl)-propenone | 5 mg |
| Glycofurol 75 | 0.2 ml |
| Aq. bidist. sterile | ad 1.0 ml |

Example D

| Injection solutions: | |
|---|---|
| Compound of formula I, e.g. E)-(RS)-3-{5-(2,4-diamino-pyrimidin-5-ylmethyl)-2,3-dimethoxy-phenyl}-1-(1-propyl-1H-phthalazin-2-yl)-propenone | 5 mg |
| Propylene glycol | 0.5 ml |
| Aq. bidist. sterile | ad 1.0 ml |

What is claimed is:

1. A compound of formula

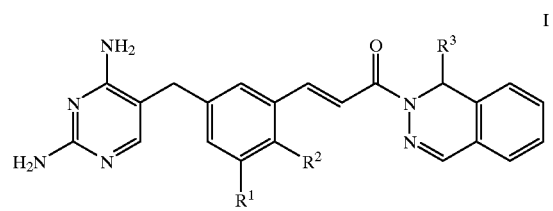

wherein
  $R^1$ is lower alkoxy;
  $R^2$ is hydroxy or lower alkoxy;
  $R^3$ is hydrogen, cyano, lower alkyl, alkenyl, cycloalkyl, bicyclyl selected from the group consisting of [bicyclo[2.2.1] hept-2endo-yl and bicyclo[2.2.1] hept-2exo-yl] 2-endo-bicyclo[2.2.1]heptyl and 2-exo-bicyclo[2.2.1] heptyl, aryl, a 4 to 6 membered heterocyclic ring having 1 to 3 hetero atoms taken from the group consisting of N, O and S, heteroaryl, aryl-Q-alkyl, or a group of the formula —$CR^4R^{4'}COR^5$;
  Q is —SO— or —$SO_2$—;
  $R^4$ and $R^{4'}$ are each independently hydrogen, alkyl, aryl or a 4 to 6 membered heterocyclic ring having 1 to 3 hetero atoms taken from the group consisting of N, O and S;
  $R^5$ is hydrogen, alkyl, alkoxy, hydroxy, aryl or a 4 to 6 membered heterocyclic ring having 1 to 3 hetero atoms taken from the group consisting of N, O and S; or
  $R^4$ and $R^5$ together form —$(CH_2)_n$—, and
  n is a whole number between 2 to 5 inclusive,
wherein
  lower alkoxy, lower alkyl, alkyl, and cycloalkyl are unsubstituted or substituted by one or more groups R, wherein R is selected from the group consisting of amino, dialkylamino, morpholino, piperidino, piperazino, hydroxy, hydroxy which is esterified by a naturally occurring amino acid, hydroxy which is esterified by sulfuric acid, halide, nitrile, thiocyanato, sulfato, lower-alkylsulphanoyl, oxo, carboxy, alkoxycarbonyl, carbamoyloxy, alkoxy, morpholinoalkoxy, piperidinoalkoxy, and cycloalkyl;
  aryl, heterocyclyl and heteroaryl are unsubstituted or substituted by one or more groups selected from phenyl, lower alkyl, lower alkyl which is substituted by one or more groups R, cycloalkyl, cycloalkyl which is substituted by one or more groups R, hydroxy, cyano, thiocyanato, amino, halide, oxo, lower alkoxy, lower alkoxy which is substituted by one or more groups R, lower alkoxycarbonyl, di(lower alkyl)amino, carbamoyl, mono- or di-lower alkylcarbamoyl, lower alkylsulfamoyl, lower alkylsulfonyl, sulfamoyl, N-mono- or di-lower alkylsulfamoyl, a 4 to 6 membered heterocyclic ring having 1 to 3 hetero atoms taken from the group consisting of N, O and S, a 4 to 6 membered heterocyclic ring having 1 to 3 hetero atoms taken from the group consisting of N, O and S and which is substituted by one or more groups R, lower alkyl substituted by a 4 to 6 membered heterocyclic ring having 1 to 3 hetero atoms taken from the group consisting of N, O and S, lower alkyl substituted by a 4 to 6 membered heterocyclic ring having 1 to 3 hetero atoms taken from the group consisting of N, O and S and which is substituted by one or more groups R, a lower alkyl substituted by one or more groups R and substituted by a 4 to 6 membered heterocyclic ring having 1 to 3 hetero atoms taken from the group consisting of N, O and S, and a lower alkyl substituted by one or more groups R and substituted by a 4 to 6 membered heterocyclic ring having 1 to 3 hetero atoms taken from the group consisting of N, O and S and substituted by one or more groups R;

alkenyl is unsubstituted or substituted by one or more substitutents selected from the group consisting of cyano, acryloyl, heteroaryl and heteroaryl which is substituted by one or more groups R;

and the enantiomers and diastereomers thereof, as well as the pharmaceutically acceptable salts thereof.

2. The compound of claim 1, wherein $R^2$ is hydroxy.

3. The compound of claim 2, wherein $R^3$ is aryl or heteroaryl.

4. The compound of claim 3, wherein $R^3$ is aryl which is unsubstituted or substituted by hydroxyalkyl.

5. The compound of claim 4, wherein $R^3$ is aryl which is unsubstituted.

6. The compound of claim 5, (E)-(RS)-3-[5-(2,4-diamino-pyrimidin-5-ylmethyl)-2-hydroxy-3-methoxy-phenyl]-1-(1-phenyl-1H-phthalazin-2-yl)-propenone.

7. The compound of claim 4, wherein $R^3$ is aryl which is substituted by hydroxyalkyl.

8. The compound of claim 7, (E)-(RS)-3-[5-(2,4-Diamino-pyrimidin-5-ylmethyl)-2-hydroxy-3-methoxy-phenyl]-1-[1-(4-hydroxymethyl-phenyl)-1H-phthalazin-2-yl]-propenone.

9. The compound of claim 3, wherein $R^3$ is heteroaryl.

10. The compound of claim 9, (E)-(RS)-3-[5-(2,4-Diamino-pyrimidin-5-ylmethyl)-2-hydroxy-3-methoxy-phenyl]-1-(1-furan-2-yl-1H-phthalazin-2-yl)-propenone.

11. The compound of claim 1, wherein $R^2$ is lower alkoxy which is substituted by one or more groups selected from carbalkoxy and alkoxy.

12. The compound of claim 11, wherein $R^2$ is lower alkoxy which is substituted by alkoxy.

13. The compound of claim 12, wherein $R^3$ is aryl or heteroaryl.

14. The compound of claim 13, wherein $R^3$ is aryl which is unsubstituted or substituted by lower alkyl which is unsubstituted or substituted with hydroxy.

15. The compound of claim 14, wherein $R^3$ is aryl which is unsubstituted.

16. The compound of claim 15, (E)-(RS)-3-[5-(2,4-diamino-pyrimidin-5-ylmethyl)-3-methoxy-2-methoxymethoxy-phenyl]-1-(1-phenyl-1H-phthalazin-2-yl)-propenone.

17. The compound of claim 14, wherein $R^3$ is aryl which is substituted by lower alkyl which is substituted with hydroxy.

18. The compound of claim 17, (E)-(RS)-3-[5-(2,4-Diamino-pyrimidin-5-ylmethyl)-3-methoxy-2-methoxymethoxy-phenyl]-1-[1-(4-hydroxymethyl-phenyl)-1H-phthalazin-2-yl]-propenone.

19. The compound of claim 12, wherein $R^3$ is heteroaryl.

20. The compound of claim 19, (E)-(RS)-3-[5-(2,4-Diamino-pyrimidin-5-ylmethyl)-3-methoxy-2-methoxymethoxy-phenyl]-1-(1-furan-2-yl-1H-phthalazin-2-yl)-propenone.

21. The compound of claim 11, wherein $R^2$ is lower alkoxy which is substituted by carbalkoxy.

22. The compound of claim 21, methyl (E)-(RS)-{4-(2,4-diamino-pyrimidin-5-ylmethyl)-2-methoxy-6-(3-oxo-3-(1-phenyl-1-H-phthalazin-2-yl)-propenyl}-phenoxy}-acetate.

23. (E)-(RS)-3-[5-(2,4-Diamino-pyrimidin-5-ylmethyl)-2,3-dimethoxy- phenyl]-1-[1-(2,3-dihydro-benzo[1,4]dioxin-6-yl)-1H-phthalazin-2-yl]-propenone.

24. (E)-(RS)-3-[5-(2,4-diamino-pyrimidin-5-ylmethyl)-3-methoxy-2-(2-morpholin-4-yl-ethoxy)-phenyl]-1-(1-phenyl-1H-phthalazin-2-yl)-propenone.

25. The compound of claim 1, wherein $R^2$ is lower alkoxy which is unsubstituted.

26. The compound of claim 25, wherein $R^3$ is aryl which is unsubstituted or substituted by one or more groups selected from lower alkyl which is unsubstituted or substituted, lower alkoxy which is unsubstituted or substituted, halide, hydroxy, cyano, heteroaryl which is unsubstituted, lower alkylsulphanoyl, lower alkoxy carbonyl, di(lower alkyl) amino, hydroxy optionally esterified with an amino acid or sulphuric acid, N-di-lower alkylsulphamoyl, aryl, and heterocyclyl-lower alkyl.

27. The compound of claim 26, wherein $R^3$ is aryl which is unsubstituted.

28. The compound of claim 27, (E)-(RS)-3-[5-(2,4-Diamino-pyrimidin-5-ylmethyl)-2,3-dimethoxy-phenyl]-1-(1-phenyl-1H-phthalazin-2-yl)-propenone.

29. The compound of claim 27, (E)-R-(−)-3-[5-(2,4-Diamino-pyrimidin-5-ylmethyl)-2,3-dimethoxy-phenyl]-1-(1-phenyl-1H-phthalazin-2-yl)-propenone.

30. The compound of claim 27, (E)-S-(+)-3-[5-(2,4-Diamino-pyrimidin-5-ylmethyl)-2,3-dimethoxy-phenyl]-1-(1-phenyl-1H-phthalazin-2-yl)-propenone.

31. The compound of claim 26, wherein $R^3$ is aryl which is substituted by lower alkyl which is unsubstituted or substituted.

32. The compound of claim 31, wherein $R^3$ is aryl which is substituted by lower alkyl which is unsubstituted.

33. The compound of claim 32, (E)-(RS)-1-[1-(4-tert-Butyl-phenyl)-1H-phthalazin-2-yl]-3-[5-(2,4-diamino-pyrimidin-5-ylmethyl)-2,3-dimethoxy-phenyl]-propenone.

34. The compound of claim 32, (E)-(RS)-3-[5-(2,4-Diamino-pyrimidin-5-ylmethyl)-2,3-dimethoxy-phenyl]-1-(1-p-tolyl-1H-phthalazin-2-yl)-propenone.

35. The compound of claim 32, (E)-(RS)-3-[5-(2,4-Diamino-pyrimidin-5-ylmethyl)-2,3-dimethoxy-phenyl]-1-[1-(4-ethyl-phenyl)-1H-phthalazin-2-yl]-propenone.

36. The compound of claim 32, (E)-(RS)-3-[5-(2,4-Diamino-pyrimidin-5-ylmethyl)-2,3-dimethoxy-phenyl]-1-[1-(3,4-dimethyl-phenyl)-1H-phthalazin-2-yl]-propenone.

37. The compound of claim 32, (E)-(RS)-3-[5-(2,4-Diamino-pyrimidin-5-ylmethyl)-2,3-dimethoxy-phenyl]-1-[1-(2,4,6-trimethyl-phenyl)-1H-phthalazin-2-yl]-propenone.

38. The compound of claim 32, (E)-(RS)-3-[5-(2,4-Diamino-pyrimidin-5-ylmethyl)-2,3-dimethoxy-phenyl]-1-(1-m-tolyl-1H-phthalazin-2-yl)-propenone.

39. The compound of claim 32, (E)-(RS)-3-[5-(2,4-Diamino-pyrimidin-5-ylmethyl)-2,3-dimethoxy-phenyl]-1-[1-(3,5-dimethyl-phenyl)-1H-phthalazin-2-yl]-propenone.

40. The compound of claim 31, wherein $R^3$ is aryl which is substituted by lower alkyl which is substituted.

41. The compound of claim 40, wherein lower alkyl is substituted by one or more groups selected from hydroxy which is optionally esterified with an amino acid or sulphuric acid, dialkylamino, lower alkoxy, halide, and carbamoyl.

42. The compound of claim 41, which is present as a mixture of (E)-3-[5-(2,4-diamino-pyrimidin-5-ylmethyl)-2,3-dimethoxy-phenyl]-1-[(RS)- and -[[(SR)-1-[4-[(RS)-1-hydroxy-ethyl]-phenyl]-1H-phthalazin-2-yl]-propenone] (SR)-1-[4-[(RS)-1-hydroxy-ethyl)-phenyl]-1H-phthalazin-2-yl]-propenone.

43. The compound of claim 41, (E)-(RS)-3-{5-(2,4-Diamino-pyrimidin-5-ylmethyl)-2,3-dimethoxy-phenyl}-1-{1-(4-(2-hydroxyethyl)-phenyl-1H-phthalazin-2-yl}-propenone.

44. The compound of claim 41, (E)-(RS)-3-{5-(2,4-Diamino-pyrimidin-5-ylmethyl)-2,3-dimethoxy-phenyl}-1-{1-(4-hydroxymethyl-phenyl)-1H-phthalazin-2-yl}-propenone.

45. The compound of claim 41, (E)-(RS)-3-{5-(2,4-Diamino-pyrimidin-5-ylmethyl)-2,3-dimethoxy-phenyl}-1-{1-(2-hydroxymethyl-phenyl)-1H-phthalazin-2-yl}-propenone.

46. The compound of claim 41, (E)-(RS)-3-{5-(2,4-Diamino-pyrimidin-5-ylmethyl)-2,3-dimethoxy-phenyl}-1-{1-(3-hydroxymethyl-phenyl)-1H-phthalazin-2-yl}-propenone.

47. The compound of claim 41, (E)-(RS)-3-[5-(2,4-Diamino-pyrimidin-5-ylmethyl)-2,3-dimethoxy-phenyl]-1-[1-(2-dimethylaminomethyl-phenyl)-1H-phthalazin-2-yl]-propenone.

48. The compound of claim 41, (E)-(RS)-3-[5-(2,4-Diamino-pyrimidin-5-ylmethyl)-2,3-dimethoxy-phenyl]-1-[1-(4-trifluoromethyl-phenyl)-1H-phthalazin-2-yl]-propenone.

49. The compound of claim 41, (E)-(RS)-3-[5-(2,4-Diamino-pyrimidin-5-ylmethyl)-2,3-dimethoxy-phenyl]-1-[1-(4-methoxymethyl-phenyl)-1H-phthalazin-2-yl]-propenone.

50. The compound of claim 41, (E)-(RS)-3-[5-(2,4-Diamino-pyrimidin-5-ylmethyl)-2,3-dimethoxy-phenyl]-1-[1-[4-[(diisopropylamino)-methyl]-phenyl]-1H-phthalazin-2-yl]-propenone.

51. (E)-(RS)-3-{5-(2,4-Diamino-pyrimidin-5-ylmethyl)-2,3-dimethoxy-phenyl}-1-{1-(4-carbamoyloxymethyl-phenyl)-1H-phthalazin-2-yl }-propenone.

52. The compound of claim 41, 2-amino-propionic acid 4-(2-{3-[5-(2,4-diamino-pyrimidin-5-ylmethyl)-2,3-dimethoxy-phenyl]-acryloyl}-1,2-dihydro-phthalazin-1-yl)-benzyl ester.

53. The compound of claim 41, 2-Amino-5-guanidino-pentanoic acid 4-(2-{3-[5-(2,4-diamino-pyrimidin-5-ylmethyl)-2,3-dimethoxy-phenyl]-acryloyl}-1,2-dihydro-phthalazin-1-yl)-benzyl ester.

54. The compound of claim 41, Sulphuric acid (E)-(RS)-mono-[4-[2-[3-[5-(2,4-diamino-pyrimidin-5-ylmethyl)-2,3-dimethoxy-phenyl]-acryloyl]-1,2-dihydro-phthalazin-1-yl]-benzyl ester].

55. The compound of claim 26, wherein $R^3$ is aryl which is substituted by lower alkoxy which is unsubstituted or substituted.

56. The compound of claim 55, wherein $R^3$ is aryl which is substituted by lower alkoxy which is unsubstituted.

57. The compound of claim 56, (E)-(RS)-3-[5-(2,4-Diamino-pyrimidin-5-ylmethyl)-2,3-dimethoxy-phenyl]-1-[1-(4-methoxy-phenyl)-1H-phthalazin-2-yl]-propenone.

58. The compound of claim 56, (E)-(RS)-3-[5-(2,4-Diamino-pyrimidin-5-ylmethyl)-2,3-dimethoxy-phenyl]-1-[1-(3,4-dimethoxy-phenyl)-1H-phthalazin-2-yl]-propenone.

59. The compound of claim 56, (E)-(RS)-3-[5-(2,4-Diamino-pyrimidin-5-ylmethyl)-2,3-dimethoxy-phenyl]-1-[1-(3-methoxy-phenyl)-1H-phthalazin-2-yl]-propenone.

60. The compound of claim 56, (E)-(RS)-3-[5-(2,4-Diamino-pyrimidin-5-ylmethyl)-2,3-dimethoxy-phenyl]-1-[1-(3,4,5-trimethoxy-phenyl)-1H-phthalazin-2-yl]-propenone.

61. The compound of claim 55, wherein $R^3$ is aryl which is substituted by lower alkoxy which is substituted.

62. The compound of claim 61, wherein the lower alkoxy is substituted by one or more groups selected from the group consisting of halide, alkoxy, and hydroxy.

63. The compound of claim 62, (E)-(RS)-3-[5-(2,4-Diamino-pyrimidin-5-ylmethyl)-2,3-dimethoxy-phenyl]-1-[1-(4-trifluoromethoxy-phenyl)-1H-phthalazin-2-yl]-propenone.

64. The compound of claim 62, which is present as a mixture of (E)-3-[5-(2,4-Diamino-pyrimidin-5-ylmethyl)-2,3-dimethoxy-phenyl]-1-[(RS)-and -[(SR)-1-[4-[(RS)-1-ethoxy-ethoxy]-phenyl]-1H-phthalazin-2-yl]-propenone.

65. The compound of claim 62, (E)-(RS)-3-[5-(2,4-Diamino-pyrimidin-5-ylmethyl)-2,3-dimethoxy-phenyl]-1-[1-[4-(2-ethoxy-ethoxy)-phenyl]-1H-phthalazin-2-yl]-propenone.

66. The compound of claim 62, (E)-(RS)-3-[5-(2,4-Diamino-pyrimidin-5-ylmethyl)-2,3-dimethoxy-phenyl]-1-[1-[4-(2-hydroxy-ethoxy)-phenyl]-1H-phthalazin-2-yl]-propenone.

67. The compound of claim 62, (E)-(RS)-3-[5-(2,4-Diamino-pyrimidin-5-ylmethyl)-2,3-dimethoxy-phenyl]-1-[1-(2,3-dihydro-benzo[1,4]dioxin-6-yl)-1H-phthalazin-2-yl]-propenone.

68. The compound of claim 62, (E)-(RS)-1-(1-Benzo[1,3]dioxol-6-yl-1H-phthalazin-2-yl)-3-[5-(2,4-diamino-pyrimidin-5-ylmethyl)-2,3-dimethoxy-phenyl]-propenone.

69. The compound of claim 26, (E)-(RS)-1-[1-(4-Chloro-phenyl)-1H-phthalazin-2-yl]-3-[5-(2,4-diamino-pyrimidin-5-ylmethyl)-2,3-dimethoxy-phenyl]-propenone.

70. The compound of claim 26, (E)-(RS)-3-[5-(2,4-diamino-pyrimidin-5-ylmethyl)-2,3-dimethoxy-phenyl]-1-[1-(4-fluoro-phenyl)-1H-phthalazin-2-yl]-propenone.

71. The compound of claim 26, (E)-(RS)-3-[5-(2,4-Diamino-pyrimidin-5-ylmethyl)-2,3-dimethoxy-phenyl]-1-[1-(2,4-difluoro-phenyl)-1H-phthalazin-2-yl]-propenone.

72. The compound of claim 26, (E)-(RS)-3-{5-(2,4-Diamino-pyrimidin-5-ylmethyl)-2,3-dimethoxy-phenyl}-1-{1-(4-hydroxy-phenyl)-1H-phthalazin-2-yl}-propenone.

73. The compound of claim 26, (E)-(RS)-3-{5-(2,4-Diamino-pyrimidin-5-ylmethyl)-2,3-dimethoxy-phenyl}-1-{1-(3-hydroxy-phenyl)-1H-phthalazin-2-yl}-propenone.

74. The compound of claim 26, (E)-(RS)-4-[2-[3-[5-(2,4-Diamino-pyrimidin-5-ylmethyl)-2,3-dimethoxy-phenyl]-acryloyl]-1,2-dihydro-phthalazin-1-yl]-benzonitril.

75. The compound of claim 26, (E)-(RS)-4-[2-[3-[5-(2,4-Diamino-pyrimidin-5-ylmethyl)-2,3-dimethoxy-phenyl]-acryloyl]-1,2-dihydro-phthalazin-1-yl]-N,N-dimethyl-benzenesulfonamid.

76. The compound of claim 26, (E)-(RS)-2-(2-{3-[5-(2,4-Diamino-pyrimidin-5-ylmethyl)-2,3-dimethoxy-phenyl]- acryloyl}-1,2-dihydro-phthalazin-1-yl)-N,N-dimethyl-benzene-suphonamide.

77. The compound of claim 26, (E)-(RS)-3-[5-(2,4-Diamino-pyrimidin-5-ylmethyl)-2,3-dimethoxy-phenyl]-1-[1-(4-methylsulfanyl-phenyl)-1H-phthalazin-2-yl]-propenone.

78. The compound of claim 26, (E)-(R)-3-[5-(2,4-Diamino-pyrimidin-5-ylmethyl)-2,3-dimethoxy-phenyl]-1-[1-(4-methylsulfanyl-phenyl)-1H-phthalazin-2-yl]-propenone.

79. The compound of claim 26, (E)-(S)-3-[5-(2,4-Diamino-pyrimidin-5-ylmethyl)-2,3-dimethoxy-phenyl]-1-[1-(4-methylsulfanyl-phenyl)-1H-phthalazin-2-yl]-propenone.

80. The compound of claim 26, (E)-(RS)-4-[2-[3-[5-(2,4-Diamino-pyrimidin-5-ylmethyl)-2,3-dimethoxy-phenyl]-acryloyl]-1,2-dihydro-phthalazin-1-yl]-benzoic acid tert-butyl ester.

81. The compound of claim 26, (E)-(RS)-3-[5-(2,4-Diamino-pyrimidin-5-ylmethyl)-2,3-dimethoxy-phenyl]-1-[1-(4-dimethylamino-phenyl)-1H-phthalazin-2-yl]-propenone.

82. The compound of claim 26, (E)-(RS)-1-(1-Biphenyl-4-yl-1H-phthalazin-2-yl)-3-[5-(2,4-diamino-pyrimidin-5-ylmethyl)-2,3-dimethoxy-phenyl]-propenone.

83. The compound of claim 26, (E)-(RS)-3-[5-(2,4-Diamino-pyrimidin-5-ylmethyl)-2,3-dimethoxy-phenyl]-1-[1-(4-pyrrol-1-yl-phenyl)-1H-phthalazin-2-yl]-propenone.

84. The compound of claim 26, (E)-(RS)-3-[5-(2,4-Diamino-pyrimidin-5-ylmethyl)-2,3-dimethoxy-phenyl]-1-[1-[4-(4-methyl-piperazin-1-ylmethyl)-phenyl]-1H-phthalazin-2-yl]-propenone.

85. The compound of claim 26, (E)-(RS)-3-[5-(2,4-Diamino-pyrimidin-5-ylmethyl)-2,3-dimethoxy-phenyl]-1-[1-(4-morpholin-4-ylmethyl-phenyl)-1H-phthalazin-2-yl]-propenone.

86. The compound of claim 25, wherein $R^3$ is hydrogen, that is, (E)-3-[5-(2,4-Diamino-pyrimidin-5-ylmethyl)-2,3-dimethoxy-phenyl]-1-(1H-phthalazin-2-yl)-propenone.

87. The compound of claim 25, wherein $R^3$ is cycloalkyl which is unsubstituted or substituted.

88. The compound of claim 87, wherein Ra is cycloalkyl which is unsubstituted.

89. The compound of claim 88, (E)-(RS)-1-(1-Cyclopropyl-1H-phthalazin-2-yl)-3-[5-(2,4-diamino-pyrimidin-5-ylmethyl)-2,3-dimethoxy-phenyl]-propenone.

90. The compound of claim 88, (E)-(R)-1-(1-Cyclopropyl-1H-phthalazin-2-yl)-3-[5-(2,4-diamino-pyrimidin-5-ylmethyl)-2,3-dimethoxy-phenyl]-propenone.

91. The compound of claim 88, (E)-(S)-1-(1-Cyclopropyl-1H-phthalazin-2-yl)-3-[5-(2,4-diamino-pyrimidin-5-ylmethyl)-2,3-dimethoxy-phenyl]-propenone.

92. The compound of claim 88, (E)-(RS)-1-(1-Cyclobutyl-1H-phthalazin-2-yl)-3-[5-(2,4-diamino-pyrimidin-5-ylmethyl)-2,3-dimethoxy-phenyl]-propenone.

93. The compound of claim 88, (E)-(RS)-1-(1-Cyclopentyl-1H-phthalazin-2-yl)-3-[5-(2,4-diamino-pyrimidin-5-ylmethyl)-2,3-dimethoxy-phenyl]-propenone.

94. The compound of claim 88, (E)-(RS)-1-(1-Cyclohexyl-1H-phthalazin-2-yl)-3-[5-(2,4-diamino-pyrimidin-5-ylmethyl)-2,3-dimethoxy-phenyl]-propenone.

95. The compound of claim 87, wherein $R^3$ is cycloalkyl which is substituted by oxo.

96. The compound of claim 95, which is a mixture of diastereomers of (E)-(RS)-2-(2-{3-[5-(2,4-Diamino-pyrimidin-5-ylmethyl)-2,3-dimethoxy-phenyl]-acryloyl}-1,2-dihydro-phthalazin-1-yl)-cyclopentanone.

97. The compound of claim 95, which is a mixture of diastereomers of (E)-(RS)-2-(2-{3-[5-(2,4-Diamino-pyrimidin-5-ylmethyl)-2,3-dimethoxy-phenyl]-acryloyl}-1,2-dihydro-phthalazin-1-yl)-cyclohexanone.

98. The compound of claim 25, wherein $R^3$ is lower alkyl which is unsubstituted or substituted.

99. The compound of claim 98, wherein $R^3$ is lower alkyl which is unsubstituted.

100. The compound of claim 99, (E)-(RS)-1-(1-Butyl-1H-phthalazin-2-yl)-3-[5-(2,4-diamino-pyrimidin-5-ylmethyl)-2,3-dimethoxy-phenyl]-propenone.

101. The compound of claim 99, (E)-(RS)-1-(1-tert-Butyl-1H-phthalazin-2-yl)-3-[5-(2,4-diamino-pyrimidin-5-ylmethyl)-2,3-dimethoxy-phenyl]-propenone.

102. The compound of claim 99, (E)-R-(−)-3-[5-(2,4-Diamino-pyrimidin-5-ylmetlyl)-2,3-dimelhoxy-phenyl]-1-(1-methyl-1H-phthalazin-2-yl)-propenone.

103. The compound of claim 99, (E)-R-(−)-3-[5-(2,4-Diamino-pyrimidin-5-ylmethyl)-2,3-dimethoxy-phenyl]-1-(1-methyl-1H-phthalazin-2-yl)-propenone.

104. The compound of claim 99, (E)-R-(−)-3-[5-(2,4-Diamino-pyrimidin-5-ylmethyl)-2,3-dimethoxy-phenyl]-1-(1-propyl-1H-phthalazin-2-yl)-propenone.

105. The compound of claim 99, (E)-S-(+)-3-[5-(2,4-Diamino-pyrimidin-5-ylmethyl)-2,3-dimethoxy-phenyl]-1-(1-methyl-1H-phthalazin-2-yl)-propenone.

106. The compound of claim 99, (E)-(RS)-3-{5-(2,4-Diamino-pyrimidin-5-ylmethyl)-2,3-dimethoxy-phenyl}-1-(1-methyl-1H-phthalazin-2-yl)-propenone.

107. The compound of claim 99, (E)-(RS)-3-{5-(2,4-Diamino-pyrimidin-5-ylmethyl)-2,3-dimethoxy-phenyl}-1-(1-ethyl-1H-phthalazin-2-yl)-propenone.

108. The compound of claim 99, (E)-(RS)-3-{5-(2,4-Diamino-pyrimidin-5-ylmethyl)-2,3-dimethoxy-phenyl}-1-(1-propyl-1H-phthalazin-2-yl)-propenone.

109. The compound of claim 99, (E)-(RS)-3-{5-(2,4-Diamino-pyrimidin-5-ylmethyl)-2,3-dimethoxy-phenyl}-1-(1-prop-2-yl-1H-phthalazin-2-yl)-propenone.

110. The compound of claim 99, (E)-(RS)-3-{5-(2,4-Diamino-pyrimidin-5-ylmethyl)-2,3-dimethoxy-phenyl}-1-{1-(3-methyl-butyl)-1H-phthalazin-2-yl}-propenone.

111. The compound of claim 98, wherein $R^3$ is lower alkyl which is substituted by one or more groups selected from hydroxy which is optionally esterified by an amino acid or sulfuric acid, lower-alkylsulphanoyl, halide, sulfato, thiocyanato, carbamoyloxy, oxo, heterocyclyl which is unsubstituted or substituted by one or more lower alkyl groups, and, and cycloalkyl which is unsubstituted.

112. The compound of claim 111, (E)-(RS)-3-{5-(2,4-Diamino-pyrimidin-5-ylmethyl)-2,3-dimethoxy-phenyl}-1-(3-hydroxy-prop-1-yl-1H-phthalazin-2-yl)-propenone.

113. The compound of claim 111, (E)-(RS)-3-{5-(2,4-Diamino-pyrimidin-5-ylmethyl)-2,3-dimethoxy-phenyl}-1-{(4-hydroxy-but-1-yl)-1H-phthalazin-2-yl}-propenone.

114. The compound of claim 111, (E)-(RS)-Carbamic acid 4-(2-{3-[5-(2,4-diamino-pyrimidin-5-ylmethyl)-2,3-dimethoxy-phenyl]-acryloyl}-1,2-dihydro-phthalazin-1-yl)-butyl ester.

115. The compound of claim 111, (E)-(RS)-Carbamic acid 4-(2-{3-[5-(2,4-diamino-pyrimidin-5-ylmethyl)-2,3-dimethoxy-phenyl]-acryloyl}-1,2-dihydro-phthalazin-1-yl)-propyl ester.

116. The compound of claim 111, (E)-(RS)-3-[5-(2,4-Diamino-pyrimidin-5-ylmethyl)-2,3-dimethoxy-phenyl]-1-(1-tridecafluorohexyl-1H-phthalazin-2-yl)-propenone.

117. The compound of claim 111, (E)-(RS)-3-[5-(2,4-Diamino-pyrimidin-5-ylmethyl)-2,3-dimethoxy-phenyl]-1-(1-methylsulfanylmethyl-1H-phthalazin-2-yl)-propenone.

118. The compound of claim 111, Sulphuric acid (E)-(RS)-mono-[4-[2-[3-[5-(2,4-diamino-pyrimidin-5-ylmethyl)-2,3-dimethoxy-phenyl]-acryloyl]-1,2-dihydro-phthalazin-1-yl]-butyl ester].

119. The compound of claim 111, (E)-(RS)-3-{5-(2,4-diamino-pyrimidin-5-ylmethyl)-2,3-dimethoxy-phenyl}-1-{1-(4-thiocyanato-butyl)-1H-phthalazin-2-yl}-propenone.

120. (E)-(RS)-3-[5-(2,4-Diamino-pyrimidin-5-ylmethyl)-2,3-dimethoxy-phenyl]-1-[1-(2-[1,3]dioxolan-2-yl-ethyl)-1H-phthalazin-2-yl]-propenone.

121. The compound of claim 111, (E)-(RS)-3-{5-(2,4-diamino-pyrimidin-5-ylmethyl)-2,3-dimethoxy-phenyl}-1-{1[2-(2,2-dimethyl-[1,3]-dioxolan-4-yl)-ethyl]-1H-phthalazin-2-yl}-propenone.

122. (E)-(RS)-Morpholine-4-carboxylic acid 4-(2-{3-[5-(2,4-diamino-pyrimidin-5-ylmethyl)-2,3-dimethoxy-phenyl]-acryloyl}-1,2-dihydro-phthalazin-1-yl)-butyl ester.

123. The compound of claim 111, (E)-(RS)-1-Cyclohexylmethyl-1H-phthalazin-2-yl)-3-[5-(2,4-diamino-pyrimidin-5-ylmethyl)-2,3-dimethoxy-phenylpropenone.

124. The compound of claim 111, (E)-(RS)-3-{5-(2,4-diamino-pyrimidin-5-ylmethyl)-2,3-dimethoxy-phenyl}-acryloyl-1,2-dihydrophthalazin-1-yl-propionaldehyde.

125. The compound of claim 111, (E)-(RS)-3-{5-(2,4-diamino-pyrimidin-5-ylmethyl)-2,3-dimethoxy-phenyl}-1-{1(3,4-dihydroxy-butyl)-1H-phthalazin-2-yl}-propenone.

126. The compound of claim 25, wherein $R^3$ is bicyclyl.

127. The compound of claim 120, (E)-1-[(RS)-1-Bicyclo[2.2.1]hept-2endo-and/or 2exo-yl-1H-phthalazin-2-yl]-3-[5-(2,4-diamino-pyrimidin-5-ylmethyl)-2,3-dimethoxy-phenyl]-propenone.

128. (E)-(RS)-1-(1-Adamantan-2-yl-1H-phthalazin-2-yl)-3-[5-(2,4-diamino-pyrimidin-5-ylmethyl)-2,3-dimethoxy-phenyl]-propenone.

129. The compound of claim 25, wherein $R^3$ is alkenyl which is unsubstituted or substituted by one or more groups selected from cyano, acryloyl, and heterocyclyl which is unsubstituted or substituted by one or more groups selected from hydroxy and oxo.

130. The compound of claim 129, which is present as a mixture of (E) and (Z)-(RS)-5[2-[(E)-3-[5-(2,4-diamino-pyrimidin-5-ylmethyl)-2,3-dimethoxy-phenyl]-acryloyl]-1,2-dihydrophthalazin-1-yl]-pent-2-enenitrile.

131. (E)-(RS)-1-(1-Benzo[1,3]dioxol-5-yl-1H-phthalazin-2-yl)-3-[5-(2,4-diamino-pyrimidin-5-ylmethyl)-2,3-dimethoxy-phenyl]-propenone.

132. (E)-(RS)-3-[5-(2,4-Diamino-pyrimidin-5-ylmethyl)-2,3-dimethoxy-phenyl]-1-(1-[1,3]dioxclo[4,5-b]pyridin-6-yl-1H-phthalazin-2-yl)-propenone.

133. Allyl (E)-(RS)-5 [2-[(E)-3-[5-(2,4-diamino-pyrimidin-5-ylmethyl)-2,3-dimethoxy-phenyl]-acryloyl]-1,2-dihydrophthalazin-1-yl]-pent-2-enoate.

134. The compound of claim 25, wherein $R^3$ is heterocyclyl which is unsubstituted or substituted by oxo.

135. The compound of claim 134, (E)-(RS)-3-[5-(2,4-Diamino-pyrimidin-5-ylmethyl)-2,3-dimethoxy-phenyl]-1-(1-[1,3]dithian-2-yl-1H-phthalazin-2-yl)-propenone.

136. The compound of claim 134, (E)-(RS)-3-(2-{3-[5-(2,4-Diamino-pyrimidin-5-ylmethyl)-2,3-dimethoxy-phenyl]-acryloyl}-1,2-dihydro-phthalazin-1-yl)-tetrahydro-pyran-2-one, which is present as a mixture of diastereomers.

137. The compound of claim 25, wherein $R^3$ is aryl-Q-alkyl and each of alkyl and aryl are unsubstituted.

138. The compound of claim 137, wherein Q is —SO—.

139. The compound of claim 138, (E)-(RS)-1-(1-Phenylsulphinylmethyl-1H-phthalazin-2-yl)-3-[5-(2,4-diamino-pyrimidin-5-ylmethyl)-2,3-dimethoxy-phenyl]-propenone.

140. The compound of claim 137, wherein Q is —SO$_2$—.

141. The compound of claim 140, (E)-(RS)-1-(1-Benzenesulfonylmethyl-1H-phthalazin-2-yl)-3-[5-(2,4-diamino-pyrimidin-5-ylmethyl)-2,3-dimethoxy-phenyl]-propenone.

142. The compound of claim 25, wherein $R^3$ is —CR$^4$R$^{4"}$COR$^5$.

143. The compound of claim 142, wherein $R^4$ and $R^{4"}$ are both hydrogen.

144. The compound of claim 143, wherein $R^5$ is alkyl, aryl, or heteroaryl.

145. The compound of claim 144, (E)-(RS)-3-[5-(2,4-Diamino-pyrimidin-5-ylmethyl)-2,3-dimethoxy-phenyl]-1-[1-(2-oxo-propyl)-1H-phthalazin-2-yl]-propenone.

146. The compound of claim 144, (E)-(RS)-3-[5-(2,4-Diamino-pyrimidin-5-ylmethyl)-2,3-dimethoxy-phenyl]-1-[1-(2-oxo-2-phenyl-ethyl)-1H-phthalazin-2-yl]-propenone.

147. The compound of claim 144, (E)-(RS)-3-[5-(2,4-Diamino-pyrimidin-5-ylmethyl)-2,3-dimethoxy-phenyl]-1-[1-(2-furan-2-yl-2-oxo-ethyl)-1H-phthalazin-2-yl]-propenone.

148. The compound of claim 142, wherein $R^4$ and $R^{4"}$ are both alkyl.

149. The compound of claim 148, wherein $R^5$ is alkoxy or hydroxy.

150. The compound of claim 149, Methyl (E)-(RS)-2-(2-{3-[5-(2,4-Diamino-pyrimidin-5-ylmethyl)-2,3-dimethoxy-phenyl]-acryloyl}-1,2-dihydro-phthalazin-1-yl)-2-methyl-propionate.

151. The compound of claim 149, (E)-(RS)-2-(2-{3-[5-(2,4-diamino-pyrimidin-5-ylmethyl)-2,3-dimethoxy-phenyl]-acryloyl}-1,2-dihydro-phthalazin-1-yl)-2-methyl-propionic acid.

152. The compound of claim 142, wherein $R^4$ is alkyl and $R^{4"}$ is hydrogen.

153. The compound of claim 152, wherein $R^5$ is aryl.

154. The compound of claim 153, (E)-(RS)-3-[5-(2,4-Diamino-pyrimidin-5-ylmethyl)-2,3-dimethoxy-phenyl]-1-[1-(1-methyl-2-oxo-2-phenyl-ethyl)-1H-phthalazin-2-yl]-propenone which is present as a mixture of diastereomers.

155. The compound of claim 25, wherein $R^3$ is heteroaryl which is unsubstituted or substituted.

156. The compound of claim 155, wherein the heteroaryl is unsubstituted.

157. The compound of claim 156, (E)-(RS)-3-[5-(2,4-Diamino-pyrimidin-5-ylmethyl)-2,3-dimethoxy-phenyl]1-(1-pyridin-2-yl-1H-phthalazin-2-yl)-propenone.

158. The compound of claim 156, (E)-(RS)-3-[5-(2,4-Diamino-pyrimidin-5-ylmethyl)-2,3-dimethoxy-phenyl]-1-(1-furan-2-yl-1H-phthalazin-2-yl)-propenone.

159. The compound of claim 156, (E)-(RS)-3-[5-(2,4-Diamino-pyrimidin-5-ylmethyl)-2,3-dimethoxy-phenyl]-1-(1-thiazol-2-yl-1H-phthalazin-2-yl)-propenone.

160. The compound of claim 25, (E)-(RS)-3-[5-(2,4-Diamino-pyrimidin-5-ylmethyl)-2,3-dimethoxy-phenyl]-1-[1-(5,6-dihydro-4H-pyran-2-yl)-1H-phthalazin-2-yl]-propenone.

161. The compound of claim 156, (E)-S-(−)-3-[5-(2,4-Diamino-pyrimidin-5-ylmethyl)-2,3-dimethoxy-phenyl]-1-(1-furan-2-yl-1H-phthalazin-2-yl)-propenone.

162. The compound of claim 156, (E)-R-(+)-3-[5-(2,4-Diamino-pyrimidin-5-ylmethyl)-2,3-dimethoxy-phenyl]-1-(1-furan-2-yl-1H-phthalazin-2-yl)-propenone.

163. The compound of claim 156, (E)-(RS)-3-[5-(2,4-Diamino-pyrimidin-5-ylmethyl)-2,3-dimethoxy-phenyl]-1-(1-pyridin-3-yl-1H-phthalazin-2-yl)-propenone.

164. The compound of claim 156, (E)-(RS)-3-[5-(2,4-Diamino-pyrimidin-5-ylmethyl)-2,3-dimethoxy-phenyl]-1-(1-thiophen-2-yl-1H-phthalazin-2-yl)-propenone.

165. The compound of claim 156, (E)-(RS)-3-[5-(2,4-Diamino-pyrimidin-5-ylmethyl)-2,3-dimethoxy-phenyl]-1-(1-pyridin-4-yl-1H-phthalazin-2-yl)-propenone.

166. The compound of claim 155, wherein heteroaryl is substituted by one or more groups selected from lower alkyl which is unsubstituted or substituted, lower alkoxy which is unsubstituted or substituted, di(lower alkyl) amino, carbamoyl, mono-lower-alkyl carbamoyl, heterocyclyl, and halide.

167. The compound of claim 166, wherein heteroaryl is substituted by lower alkyl which is unsubstituted or substituted.

168. The compound of claim 167, wherein heteroaryl is substituted by lower alkyl which is unsubstituted.

169. The compound of claim 168, (E)-(RS)-3-[5-(2,4-Diamino-pyrimidin-5-ylmethyl)-2,3-dimethoxy-phenyl]-1-[1-(6-methyl-pyridin-2-yl)-1H-phthalazin-2-yl]-propenone.

170. The compound of claim 168, (E)-(R)-3-[5-(2,4-Diamino-pyrimidin-5-ylmethyl)-2,3-dimethoxy-phenyl]-1-[1-(6-methyl-pyridin-3-yl)-1H-phthalazin-2-yl]-propenone.

171. The compound of claim 168, (E)-(S)-3-[5-(2,4-Diamino-pyrimidin-5-ylmethyl)-2,3-dimethoxy-phenyl]-1-[1-(6-methyl-pyridin-3-yl)-1H-phthalazin-2-yl]-propenone.

172. The compound of claim 168, (E)-(RS)-3-[5-(2,4-Diamino-pyrimidin-5-ylmethyl)-2,3-dimethoxy-phenyl]-1-[1-(6-methyl-pyridin-3-yl)-1H-phthalazin-2-yl]-propenone.

173. The compound of claim 168, (E)-(RS)-1-[1-(5-Butyl-thiophen-2-yl)-1H-phthalazin-2-yl]-3-[5-(2,4-diamino-pyrimidin-5-ylmethyl)-2,3-dimethoxy-phenyl]-propenone.

174. The compound of claim 168, (E)-(RS)-3-[5-(2,4-Diamino-pyrimidin-5-ylmethyl)-2,3-dimethoxy-phenyl]-1-[1-(5-methyl-pyridin-2-yl)-1H-phthalazin-2-yl]-propenone.

175. The compound of claim 168, (E)-(RS)-3-[5-(2,4-Diamino-pyrimidin-5-ylmethyl)-2,3-dimethoxy-phenyl]-1-[1-(2-methyl-pyridin-3-yl)-1H-phthalazin-2-yl]-propenone.

176. The compound of claim 168, (E)-(RS)-3-[5-(2,4-Diamino-pyrimidin-5-ylmethyl)-2,3-dimethoxy-phenyl]-1-[1-(4-methyl-pyridin-2-yl)-1H-phthalazin-2-yl]-propenone.

177. The compound of claim 168, (E)-(RS)-3-[5-(2,4-Diamino-pyrimidin-5-ylmethyl)-2,3-dimethoxy-phenyl]-1-[1-(2-methyl-pyridin-4-yl)-1H-phthalazin-2-yl]-propenone.

178. The compound of claim 168, (E)-(RS)-3-[5-(2,4-Diamino-pyrimidin-5-ylmethyl)-2,3-dimethoxy-phenyl]-1-[1-(2-methyl-pyrimidin-5-yl)-1H-phthalazin-2-yl]-propenone.

179. The compound of claim 168, (E)-(RS)-3-[5-(2,4-Diamino-pyrimidin-5-ylmethyl)-2,3-dimethoxy-phenyl]-1-[1-(6-ethyl-pyridin-3-yl)-1H-phthalazin-2-yl]-propenone.

180. The compound of claim 167, wherein heteroaryl is substituted by lower alkyl which is substituted by hydroxy.

181. The compound of claim 180, (E)-(RS)-3-[5-(2,4-Diamino-pyrimidin-5-ylmethyl)-2,3-dimethoxy-phenyl]-1-{1-[6-(1-hydroxy-1-methyl-ethyl)-pyridin-3-yl]-1H-phthalazin-2-yl}-propenone.

182. The compound of claim 180, (E)-(RS)-3-[5-(2,4-Diamino-pyrimidin-5-ylmethyl)-2,3-dimethoxy-phenyl]-1-[1-(6-hydroxymethyl-pyridin-3-yl)-1H-phthalazin-2-yl]-propenone.

183. The compound of claim 166, wherein the heteroaryl is substituted by halide.

184. The compound of claim 183, (E)-(RS)-1-[1-(5-Chloro-pyridin-2-yl)-1H-phthalazin-2-yl]-3-[5-(2,4-diamino-pyrimidin-5-ylmethyl)-2,3-dimethoxy-phenyl]-propenone.

185. The compound of claim 183, (E)-(RS)-1-[1-(6-Bromo-pyridin-3-yl)-1H-phthalazin-2-yl]-3-[5-(2,4-diamino-pyrimidin-5-ylmethyl)-2,3-dimethoxy-phenyl]-propenone.

186. The compound of claim 183, (E)-(RS)-1-[1-(6-Chloro-pyridin-3-yl)-1H-phthalazin-2-yl]-3-[5-(2,4-diamino-pyrimidin-5-ylmethyl)-2,3-dimethoxy-phenyl]-propenone.

187. The compound of claim 166, wherein the heteroaryl is substituted by lower alkoxy which is unsubstituted or substituted.

188. The compound of claim 187, wherein the heteroaryl is substituted by lower alkoxy which is unsubstituted.

189. The compound of claim 188, (E)-(RS)-3-[5-(2,4-Diamino-pyrimidin-5-ylmethyl)-2,3-dimethoxy-phenyl]-1-[1-(2,4-dimethoxy-pyrimidin-5-yl)-1H-phthalazin-2-yl]-propenone.

190. The compound of claim 188, (E)-(RS)-3-[5-(2,4-Diamino-pyrimidin-5-ylmethyl)-2,3-dimethoxy-phenyl]-1-[1-(4-methoxy-pyridin-2-yl)-1H-phthalazin-2-yl]-propenone.

191. The compound of claim 188, (E)-(RS)-3-[5-(2,4-Diamino-pyrimidin-5-ylmethyl)-2,3-dimethoxy-phenyl]-1-[1-(6-methoxy-pyridin-3-yl)-1H-phthalazin-2-yl]-propenone.

192. The compound of claim 187, wherein the heteroaryl is substituted by lower alkoxy which is substituted by one or more groups selected from the group consisting of hydroxy, alkoxy, aryl, heterocyclyl, and dialkyl amino.

193. The compound of claim 192, (E)-(RS)-3-[5-(2,4-Diamino-pyrimidin-5-ylmethyl)-2,3-dimethoxy-phenyl]-1-[1-[6-(2-hydroxy-ethoxy)-pyridin-3-yl]-1H-phthalazin-2-yl]-propenone.

194. The compound of claim 192, (E)-(RS)-3-[5-(2,4-Diamino-pyrimidin-5-ylmethyl)-2,3-dimethoxy-phenyl]-1-[1-[6-(2-methoxy-ethoxy)-pyridin-3-yl]-1H-phthalazin-2-yl]-propenone.

195. The compound of claim 192, (E)-(RS)-3-[5-(2,4-Diamino-pyrimidin-5-ylmethyl)-2,3-dimethoxy-phenyl]-1-[1-[6-[2-(2-methoxy-ethoxy)-ethoxy]-pyridin -3-yl]-1H-phthalazin-2-yl]-propenone.

196. The compound of claim 192, (E)-(RS)-3-[5-(2,4-Diamino-pyrimidin-5-ylmethyl)-2,3-dimethoxy-phenyl]-1-[1-[6-(3-hydroxy-propoxy)-pyridin-3-yl] 1H-phthalazin-2-yl]-propenone.

197. The compound of claim 192, 3-[5-(2,4-Diamino-pyrimidin-5-ylmethyl)-2,3-dimethoxy-phenyl]-1-{1-[6-(2-morpholin-4-yl-ethoxy)-pyridin-3-yl]-1H-phthalazin-2-yl}-propenone.

198. The compound of claim 192, 3-[5-(2,4-Diamino-pyrimidin-5-ylmethyl)-2,3-dimethoxy-phenyl]-1-{1-[6-(2-dimethylamino-ethoxy)-pyridin-3-yl]-1H-phthalazin-2-yl}-propenone.

199. The compound of claim 192, (E)-(RS)-3-[5-(2,4-Diamino-pyrimidin-5-ylmethyl)-2,3-dimethoxy-phenyl]-1-(1-[1,3]dioxolo[4,5-b]pyridin-6-yl-1H-phthalazin-2-yl)-propenone.

200. 1-[1-(6-Benzyloxy-pyridin-3-yl)-1H-phthalazin-2-yl]-3-[5-(2,4-diamino-pyrimidin-5-ylmethyl)-2,3-dimethoxy-phenyl]-propenone.

201. The compound of claim 166, (E)-(RS)-5-(2-{3-[5-(2,4-Diamino-pyrimidin-5-ylmethyl)-2,3-dimethoxy-phenyl]-acryloyl}-1,2-dihydro-phthalazin-1-yl)-pyridin-2-carboxylic acid tert-butylamide.

202. The compound of claim 166, (E)-(RS)-5-(2-{3-[5-(2,4-Diamino-pyrimidin-5-ylmethyl)-2,3-dimethoxy-phenyl]-acryloyl}-1,2-dihydro-phthalazin-1-yl)-pyridin-2-carboxylic acid amide.

203. The compound of claim 166, (E)-(RS)-3-[5-(2,4-Diamino-pyrimidin-5-ylmethyl)-2,3-dimethoxy-phenyl]-1-[1-(6-dimethylamino-pyridin-3-yl)-1H-phthalazin-2-yl]-propenone.

204. The compound of claim 166, (E)-(RS)-3-[5-(2,4-Diamino-pyrimidin-5-ylmethyl)-2,3-dimethoxy-phenyl]-1-[1-(6-morpholin-4-yl-pyridin-3-yl)-1H-phthalazin-2-yl]-propenone.

205. A pharmaceutical composition comprising a therapeutically effective amount of a compound of the formula

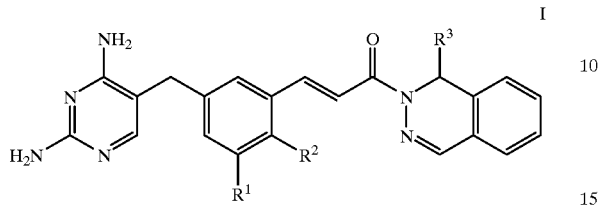

wherein

R¹ is lower alkoxy;

R² is hydroxy or lower alkoxy;

R³ is hydrogen, cyano, lower alkyl, alkenyl, cycloalkyl, bicyclyl selected from the groups consisting of 2-endo-bicyclo[2,2,1]heptyl and 2-exo-bicyclo[2,2,1]heptyl, aryl, a 4 to 6 membered heterocyclic ring having 1 to 3 hetero atoms taken from the group consisting of N, O and S, heteroaryl, aryl-Q-alkyl, or a group of the formula —CR⁴R⁴'COR⁵;

Q is —SO— or —SO₂—;

R⁴ and R⁴' are each independently hydrogen, alkyl, aryl or a 4 to 6 remembered heterocyclic ring having 1 to 3 hetero atoms selected from the group consisting of N, O and S;

R⁵ is hydrogen, alkyl, alkoxy, hydroxy, aryl or a 4 to 6 membered heterocyclic ring having 1 to 3 hetero atoms selected from the group consisting of N, O and S; or R⁴ and R⁵ together form —(CH₂)ₙ—, and n is a whole number between 2 to 5 inclusive, wherein lower alkoxy, lower alkyl, alkyl, and cycloalkyl are unsubstituted or substituted by one or more groups R, wherein R is selected from the group consisting of amino, dialkylamino, morpholino, piperidino, piperazino, hydroxy, hydroxy which is esterified by a naturally occurring amino acid, hydroxy which is esterified by sulfuric acid, halide, nitrile, thiocyanato, sulfato, lower-alkylsulphanoyl, oxo, carboxy, alkoxycarbonyl, carbamoyloxy, alkoxy, morpholinoalkoxy, piperidinoalkoxy, and cycloalkyl;

aryl, heterocyclyl and heteroaryl are unsubstituted or substituted by one or more groups selected from phenyl, lower alkyl, lower alkyl which is substituted by one or more groups R, cycloalkyl, cycloalkyl which is substituted by one or more groups R, hydroxy, cyano, thiocyanato, amino, halide, oxo, lower alkoxy, lower alkoxy which is substituted by one or more groups R, lower alkoxycarbonyl, di(lower alkyl)amino, carbamoyl, mono- or di-lower alkylcarbamoyl, lower alkylsulfamoyl, lower alkylsulfonyl, sulfamoyl, N-mono- or di-lower alkylsulfamoyl, a 4 to 6 membered heterocyclic ring having 1 to 3 hetero atoms selected from the group consisting of N, O and S, a 4 to 6 membered heterocyclic ring having 1 to 3 hetero atoms taken from the group consisting of N, O and S and which is substituted by one or more groups R, lower alkyl substituted by a 4 to 6 membered heterocyclic ring having 1 to 3 hetero atoms taken from the group consisting of N, O and S, lower all substituted by a 4 to 6 membered heterocyclic ring having 1 to 3 hetero atoms taken from the group consisting of N, O and S and which is substituted by one or more groups R, a lower alkyl substituted by one or more groups R and substituted by a 4 to 6; membered heterocyclic ring having 1 to 3 hetero atoms taken from the group consisting of N, O and S, and a lower alkyl substituted by one or more groups R and substituted by a 4 to 6 membered heterocyclic ring having 1 to 3 hetero atoms taken from the group consisting of N, O and S and substituted by one or more groups R;

alkenyl is unsubstituted or substituted by one or more substitutents selected from the group consisting of cyano, acryloyl, heteroaryl and heteroaryl which is substituted by one or more groups R, and the enantiomers and diastereomers thereof, as well as the pharmaccutically acceptable salts thereof, and a pharmaceutically acceptable carrier.

206. The composition of claim 205, wherein the compound is selected from the group (E)-(RS)-3-[5-(2,4-Diamino-pyrimidin-5-ylmethyl)-2,3-dimethoxy-phenyl]-1-(1-phenyl-1H-phthalazin-2-yl)-propenone;

(E)-(RS)-3-[5-(2,4-Diamino-pyrimidin-5-ylmethyl)-2,3-dimethoxy-phenyl]-1-(1-furan-2-yl-1H-phthalazin-2-yl)-propenone;

(E)-(RS)-3-[5-(2,4-Diamino-pyrimidin-5-ylmethyl)-2,3-dimethoxy-phenyl]-1-[1-(4-hydroxymethyl-phenyl)-1H-phthalazin-2-yl]-propenone;

(E)-(RS)-3-[5-(2,4-Diamino-pyrimidin-5-ylmethyl)-2,3-dimethoxy-phenyl]-1-[1-(4-hydroxy-phenyl)-1H-phthalazin-2-yl]-propenone;

(E)-(RS)-3-[5-(2,4-Diamino-pyrimidin-5-ylmethyl)-2,3-dimethoxy-phenyl]-1-(1-ethyl-1H-phthalazin-2-yl)-propenone;

(E)-(RS)-3-[5-(2,4-Diamino-pyrimidin-5-ylmethyl)-2,3-dimethoxy-phenyl]-1-[1-(4-hydroxy-butyl)-1H-phthalazin-2-yl]-propenone;

(E)-(RS)-3-{5-(2,4-Diamino-pyrimidin-5-ylmethyl)-2,3-dimethoxy-phenyl}-1-(1-propyl-1H-phthalazin-2-yl)-propenone;

(E)-(R)-3-[5-(2,4-Diamino-pyrimidin-5-ylmethyl)-2,3-dimethoxy-phenyl]-1-[1-(6-methyl-pyridin-3-yl)-1H-phthalazin-2-yl]-propenone;

(E)-(RS)-3-[5-(2,4-Diamino-pyrimidin-5-ylmethyl)-2,3-dimethoxy-phenyl]-1-L 1-(6-methyl-pyridin-3-yl)-1H-phthalazin-2-yl]-propenone;

(E)-(RS)-3-[5-(2,4-Diamino-pyrimidin-5-ylmethyl)-2,3-dimethoxy-phenyl]-1-[1-(6-ethyl-pyridin-3-yl)-1H-phthalazin-2-yl]-propenone; and (E)-(RS)-3-[5-(2,4-Diamino-pyrimidin-5-ylmethyl)-2,3-dimethoxy-phenyl]-1-[1-(2-methyl-pyrimidin-5-yl)-1H-phthalazin-2-yl]-propenone, as well as pharmaceutically acceptable salts of these compounds.

207. A compound of the formula

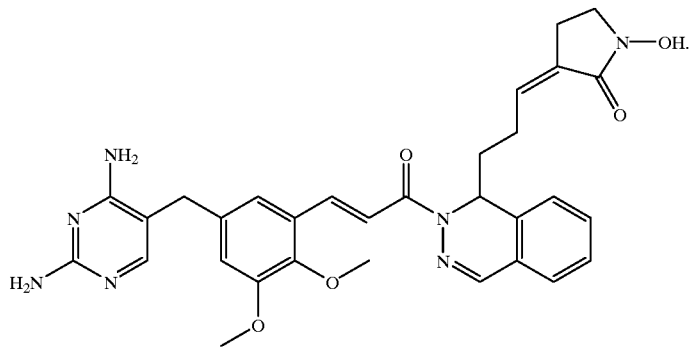

208. The compound according to claim 207, wherein said compound is the (EE)-(RS) enantiomer.

209. A method of treating bacterial infections in a mammal comprising administering to said mammal a compound of the formula

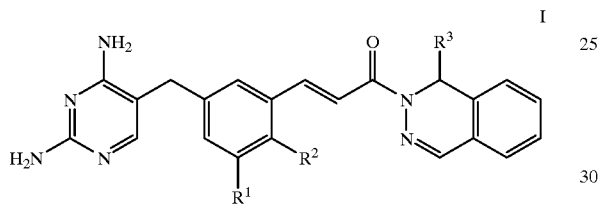

wherein
- $R^1$ is lower alkoxy;
- $R^2$ is hydroxy or lower alkoxy;
- $R^3$ is hydrogen, cyano, lower alkyl, alkenyl, cycloalkyl, bicyclyl selected from the group consisting of 2-endo-bicyclo[2.2.1]heptyl and 2-exo-bicyclo[2,2,1]heptyl, aryl, a 4 to 6 membered heterocyclic ring having 1 to 3 hetero atoms taken from the group consisting of N, O and S, heteroaryl, aryl-Q-alkyl, or a group of the formula —$CR^4R^{4'}COR^5$;
- Q is —SO— or —$SO_2$—;
- $R^4$ and $R^{4'}$ are each independently hydrogen, alkyl, aryl or a 4 to 6 membered heterocyclic ring having 1 to 3 hetero atoms selected from the group consisting of N, O and S;
- $R^5$ is hydrogen, alkyl, alkoxy, hydroxy, aryl or a 4 to 6 membered heterocyclic ring having 1 to 3 hetero atoms selected from the group consisting of N, O and S; or
- $R^4$ and $R^5$ together form —$(CH_2)_n$—, and
- n is a whole number between 2 to 5 inclusive, wherein
- lower alkoxy, lower alkyl, alkyl, and cycloalkyl are unsubstituted or substituted by one or more groups R, wherein R is selected from the group consisting of amino, dialkylamino, morpholino, piperidino, piperazino, hydroxy, hydroxy which is esterified by a naturally occurring amino acid, hydroxy which is esterified by sulfuric acid, halide, nitrile, thiocyanato, sulfato, lower-alkylsulphanoyl, oxo, carboxy, alkoxycarbonyl, carbamoyloxy, alkoxy, morpholinoalkoxy, piperidinoalkoxy, and cycloalkyl;
- aryl, heterocyclyl and heteroaryl are unsubstituted or substituted by one or more groups selected from phenyl, lower alkyl, lower alkyl which is substituted by one or more groups R, cycloalkyl, cycloalkyl which is substituted by one or more groups R, hydroxy, cyano, thiocyanato, amino, halide, oxo, lower alkoxy, lower alkoxy which is substituted by one or more groups R, lower alkoxycarbonyl, di (lower alkyl)amino, carbamoyl, mono- or di-lower alkylcarbamoyl, lower alkylsulfamoyl, lower alkylsulfonyl, sulfamoyl, N-mono- or di-lower alkylsulfamoyl, a 4 to 6 membered heterocyclic ring having 1 to 3 hetero atoms selected from the group consisting of N, O and S, a 4 to 6 membered heterocyclic ring having 1 to 3 hetero atoms taken from the group consisting of N, O and S and which is substituted by one or more groups R, lower alkyl substituted by a 4 to 6 membered heterocyclic ring having 1 to 3 hetero atoms taken from the group consisting of N, O and S, lower alkyl substituted by a 4 to 6 membered heterocyclic ring having 1 to 3 hetero atoms taken from the group consisting of N, O and S and which is substituted by one or more groups R, a lower alkyl substituted by one or more groups R and substituted by a 4 to 6 membered heterocyclic ring having 1 to 3 hetero atoms taken from the group consisting of N, O and S, and a lower alkyl substituted by one or more groups R and substituted by a 4 to 6 membered heterocyclic ring having 1 to 3 hetero atoms taken from the group consisting of N, O and S and substituted by one or more groups R;
- alkenyl is unsubstituted or substituted by one or more substitutents selected from the group consisting of cyano, acryloyl, heteroaryl and heteroaryl which is substituted by one or more groups R, and the enantiomers and diastereomers thereof, as well as the pharmaceutically acceptable salts thereof, and a pharmaceutically acceptable carrier in an amount which is effective in treating bacterial infections.

210. The method of claim 209, wherein the compound is selected from the group
- (E)-(RS)-3-[5-(2,4-Diamino-pyrimidin-5-ylmethyl)-2,3-dimethoxy-phenyl]-1-(1-phenyl-1H-phthalazin-2-yl)-propenone;
- (E)-(RS)-3-[5-(2,4-Diamino-pyrimidin-5-ylmethyl)-2,3-dimethoxy-phenyl]-1-(1-furan-2-yl-1H-phthalazin-2-yl)-propenone;
- (E)-(RS)-3-[5-(2,4-Diamino-pyrimidin-5-ylmethyl)-2,3-dimethoxy-phenyl]-1-[1-(4-hydroxymethyl-phenyl)-1H-phthalazin-2-yl]-propenone;
- (E)-(RS)-3-[5-(2,4-Diamino-pyrimidin-5-ylmethyl)-2,3-dimethoxy-phenyl]-1-[1-(4-hydroxy-phenyl)-1H-phthalazin-2-yl]-propenone;

(E)-(RS)-3-[5-(2,4-Diamino-pyrimidin-5-ylmethyl)-2,3-dimethoxy-phenyl]-1-(1-ethyl-1H-phthalazin-2-yl)-propenone;

(E)-(RS)-3-[5-(2,4-Diamino-pyrimidin-5-ylmethyl)-2,3-dimethoxy-phenyl]-1-[1-(4-hydroxy-butyl)-1H-phthalazin-2-yl]-propenone;

(E)-(RS)-3-{5-(2,4-Diamino-pyrimidin-5-ylmethyl)-2,3-dimethoxy-phennyl}-1-(1-propyl-1H-phthalazin-2-yl)-propenone;

(E)-(R)-3-[5-(2,4-Diamino-pyrimidin-5-ylmethyl)-2,3-dimethoxy-phenyl]-1-[1-(6-methyl-pyridin-3-yl)-1H-phthalazin-2-yl]-propenone;

(E)-(RS)-3-[5-(2,4-Diamino-pyrimidin-5-ylmethyl)-2,3-dimethoxy-phenyl]-1-[1-(6-methyl-pyridin-3-yl)-1H-phthalazin-2-yl]-propenone;

(E)-(RS)-3-[5-(2,4-Diamino-pyrimidin-5-ylmethyl)-2,3-dimethoxy-phenyl]-1-[1-(6-ethyl-pyridin-3-yl)-1H-phthalazin-2-yl]-propenone; and (E)-(RS)-3-[5-(2,4-Diamino-pyrimidin-5-ylmethyl)-2,3-dimethoxy-phenyl]-1-[1-(2-methyl-pyrimidin-5-yl)-1H-phthalazin-2-yl]-propenone, as well as pharmaceutically acceptable salts of these compounds.

* * * * *

UNITED STATES PATENT AND TRADEMARK OFFICE
CERTIFICATE OF CORRECTION

PATENT NO. : 6,114,330
DATED : September 5, 2000
INVENTOR(S) : Guerry et al.

Page 1 of 2

It is certified that error appears in the above-identified patent and that said Letters Patent is hereby corrected as shown below:

Column 42, claim 26,
Line 34, delete "an" and add -- a naturally occurring --.

Column 43, claim 41,
Line 10, delete "an" and add -- a naturally occurring --.

Column 46, claim 111,
Line 43, delete "an" and add -- a naturally occurring --.

Column 50, claim 199,
Line 49, delete "192" and add -- 215 --.

Column 50, claim 200,
Line 53, please add "The compound of claim 192," before the compound.

Column 51, claim 205,
Line 30, delete "remembered" and add -- membered --;

Column 52,
Line 4, delete "all" and add -- alkyl --;
Line 9, delete "6;" and add -- 6 --;
Line 22, delete "pharmaccutically" and add -- pharmaceutically --.

Column 53, claim 209,
Line 39, delete "[2,2,1]" and add -- [2.2.1] --.

UNITED STATES PATENT AND TRADEMARK OFFICE
CERTIFICATE OF CORRECTION

PATENT NO. : 6,114,330
DATED : September 5, 2000
INVENTOR(S) : Guerry et al.

It is certified that error appears in the above-identified patent and that said Letters Patent is hereby corrected as shown below:

Column 55, claim 210,
Line 8, delete "phennyl" and add -- phenyl --.

Signed and Sealed this

Twenty-third Day of October, 2001

Attest:

*Nicholas P. Godici*

NICHOLAS P. GODICI
*Acting Director of the United States Patent and Trademark Office*

*Attesting Officer*